US006057371A

United States Patent [19]
Glennon

[11] Patent Number: 6,057,371
[45] Date of Patent: May 2, 2000

[54] SIGMA RECEPTOR LIGANDS AND THE USE THEREOF

[75] Inventor: Richard A. Glennon, Richmond, Va.

[73] Assignee: Virginia Commonwealth University, Richmond, Va.

[21] Appl. No.: 07/894,771

[22] Filed: Jun. 10, 1992

Related U.S. Application Data

[63] Continuation-in-part of application No. 07/720,173, filed as application No. PCT/US90/07653, Dec. 28, 1990, abandoned, and a continuation-in-part of application No. 07/495,061, Dec. 28, 1990, Pat. No. 4,981,974.

[51] Int. Cl.[7] .................... A01N 33/02; C07C 213/00; C07C 211/00
[52] U.S. Cl. .................... 514/649; 514/651; 514/652; 514/653; 514/654; 514/655; 564/342; 564/344; 564/345; 564/347; 564/348; 564/352; 564/353; 564/354; 564/355; 564/360; 564/361; 564/366; 564/373; 564/378; 564/381; 564/382; 564/383
[58] Field of Search .................... 564/342, 344, 564/345, 347, 348, 352, 353, 354, 355, 360, 361, 366, 373, 374, 378, 381, 382, 383; 514/649, 651, 652, 653, 654, 655

[56] References Cited

U.S. PATENT DOCUMENTS

| | | | |
|---|---|---|---|
| 3,256,278 | 6/1966 | Petracek et al. | 260/247.5 |
| 4,866,062 | 9/1989 | Tóth et al. | 514/255 |
| 4,866,076 | 9/1989 | Gribble | 514/307 |
| 4,873,262 | 10/1989 | Junge et al. | 514/510 |
| 4,962,107 | 10/1990 | Nakamura et al. | 514/237.5 |
| 4,962,115 | 10/1990 | Van Daele | 514/326 |

FOREIGN PATENT DOCUMENTS

| | | |
|---|---|---|
| 0064964 | 11/1982 | European Pat. Off. |
| 0286278 | 10/1988 | European Pat. Off. |
| 0296560 | 12/1988 | European Pat. Off. |
| 0372776 | 6/1990 | European Pat. Off. |
| 0386997 | 9/1990 | European Pat. Off. |
| 1421208 | 12/1965 | France . |
| M-4274 | 8/1966 | France . |
| 966943 | 8/1964 | United Kingdom . |
| 1184023 | 3/1970 | United Kingdom . |
| 88/03756 | 6/1988 | WIPO . |

OTHER PUBLICATIONS

R. Glennon, *J. Medicinal Chemistry*, 30(1):1–12 (1987).
Samant et al., *J. Indian Chemical Society*, 56(10):1002–1005 (1979).
"Merck Index", pp. 218 and 725 (1987).
Chemical Abstracts 56, Abstract No. 1324f "Mechanism of chemical reactions" (1962).
Chemical Abstracts 54, Abstract No. 22430h (1960).
Chemical Abstracts 60, Abstract No. 12028d (1964).
Anderson et al., *J. Medicinal Chemistry*, 19(11):1270–1275 (1976).
Sharkey et al., *Eur. J. Pharmacol.* 149:171–174 (1988).
Manallack, D.T. et al., *Eur. J. Pharmacol.* 144:231–235 (1987).

Fuller, R.W. et al., *J. Med. Chem.* 14:322–325 (1971).
Foye, W.O. and Tovivich, S., *J. Pharm. Sci.* 68:591:595 (1979).
Boissier, J.R. et al., *Chem. Abstr.* 66:46195h (1967).
Boissier, J.R. et al., *Chem. Abstr.* 67:21527a (1967).
Osbond, J.M. et al., *Chem. Abstr.* 69:51816c (1968).
Gosztonyi, T. et al., *J. Label. Comp. Radiopharm.* 13(3):293–303 (1977).
Coutts, R.T. et al., *Can. J. Microbiol.* 26:844–849 (1980).
Aldous, F.A.B., *J. Med. Chem.* 17(10):1100–1111 (1974).
Fuller, R.W. et al., *J. Pharm. Pharmacol.* 25:828–829 (1973).
Fuller, R.W. et al., *Neuropharmacology* 14:739–746 (1975).
Conde, S. and Madroñero, R., *J. Med. Chem.* 21(9):978–981 (1978).
Lukovits, I., *Int. J. Quantum Chem.* 20:429–438 (1981).
Law, B., *J. Chromatog.* 407:1–18 (1987).
Johansson, A.M. et al., *J. Med. Chem.* 30:602–611 (1987).
Hacksell, U. et al., *J. Med. Chem.* 22(12):1469–1475 (1979).
McDermed, J.D. et al., *J. Med. Chem.* 18(4):362–367 (1975).
Glennon, R.A. et al., *Chem. Abstr.* 102:105731s (1985).
Beaulieu, M. et al., *Eur. J. Pharmacol.* 105:15–21 (1984).
Naiman, N. et al., *J. Med. Chem.* 32:253–256 (1989).
Largent, B.L. et al., *Mol. Pharmacol.* 32:772–784 (1987).
Beecroft, R.A. et al., *Tetrahedron* 41(18):3853–3865 (1985).
Fuller, R.W. et al., *J. Pharmacol. Exp. Therapeut.* 218(3):636–641 (1981).
Fuller, R.W. and Snoddy, H.D., *Res. Commun. Chem. Pathol. Pharmacol.* 29(1):201–204 (1980).
Boissier, J. et al., *Chem. Abstr.* 61:10691c (1961).
Roessler, *Chem. Abstr.* 61:13328g (1961).
Ruschig, H. et al., *Chem. Abstr.* 53:3253e (1959).
Shvedov, V.I. et al., *Chem. Abstr.* 73:119806q (1970).
Popov, D., *Chem. Abstr.* 67:54102m (1967).
Glennon, R.A. et al., *J. Med. Chem.* 31:1968–1971 (1988).
Prasad, R.N. et al., *J. Med. Chem.* 11:1144–1150 (1968).
Largent, B.L. et al., *Eur. J. Pharmacol.* 155:345–347 (1988).
Glennon, R.A. and Young, R., *Pharmacol. Biochem. Behav.* 17:603–607 (1982).
Glennon, R.A. et al., *J. Med. Chem.* 25:68–70 (1982).
Glennon, R.A. et al., *Eur. J. Pharmacol.* 154:339–341 (1988).

(List continued on next page.)

*Primary Examiner*—John Kight
*Assistant Examiner*—Raymond Covington
*Attorney, Agent, or Firm*—David G. Conlin; Peter F. Corless; Christine C. O'Day

[57] ABSTRACT

The invention relates to methods for the treatment of central nervous system disorders, gastrointestinal disorders, drug abuse, angina, migraine, hypertension and depression by administering a pharmaceutical composition comprising an effective amount of certain sigma receptor ligands to a patient in need of such treatment. The invention further relates to novel sigma receptor ligands having high binding to the sigma receptor and pharmaceutical compositions thereof. Unexpectedly, certain of the sigma receptor ligands of the present invention have selectivity for the sigma receptor over the DA, PCP and 5-HT$_{1A}$ receptors.

72 Claims, No Drawings

OTHER PUBLICATIONS

Arvidsson, L.-E. et al., *Prog. Drug. Res. 30*:365–471 (1986).
Glennon, R.A. and Salley, Jr., J.J., *J. Med. Chem. 24*:678–683 (1981).
Glennon, R.A. et al., *Life Sciences 35*:1475–1480 (1984).
Young, R. and Glennon, R.A., *Med. Res. Rev. 6*(1):99–130 (1986).
Glennon, R.A. et al., *Pharmacol. Biochem. Behav. 21*:895–901 (1984).
Glennon, R.A. et al., *Psychopharmacol. Bull. 22*(3):953–958 (1986).
Peroutka, S.J., *J. Neurochem. 47*(2):529–540 (1986).
Faraj, B.A. et al., *J. Med. Chem. 19*(1):20–25 (1976).
Lyon, R.A. et al., *J. Med. Chem. 29*:630–634 (1986).
Klosa, J. and Starke, H., *Chem. Abstr. 63*:11579b (1965).
Glennon, R.A. et al., *J. Med. Chem. 34*:3360–3365 (1991).
Vitolinya, M.A., *Chem. Abstr. 72*:65176t (1970).
Prasad, R.N. et al., *Chem. Abstr. 70*:11676w (1969).
Su, T.-P., *Neurosci. Lett. 71*:224–228 (1986).
Beaton, J.M. et al., *Nature 220*:800–801 (1968).
Fuller, R.W. et al., *J. Pharmacol Exp. Therapeut. 184*(1):278–284 (1973).
Fuller, R.W. et al., *Neuropharmacol. 13*:609–614 (1974).
Smith, H.E. et al., *J. Org. Chem. 40*(11):1562–1567 (1975).
Sloviter, R.S. et al., *Pharmacol. Biochem. Behav. 13*:283–286 (1980).
Pala, G. et al., *J. Med. Chem. 13*(4):668–671 (1970).
Van de Waterbeemd, H. et al., *J. Med. Chem. 30*:2175–2181 (1987).
Freifelder, M. et al., *Chem. Abstr. 61*:14559g (1964).
Tazelaar, A.P. and Veldkamp, W., *Chem. Abstr. 39*:11322b (1962).
Busch, N. and Vacher, J., *Chem. Abstr. 70*:20085e (1969).
Nauvernay, R.Y., *Chem. Abstr. 66*:55520n (1967).
Krotowska, A. et al., *Chem. Abstr. 108*:87584p (1988).
International Search Report for PCT Application No. PCT/US90/07653.
Raghupathi, R.K. et al. *J. Med. Chem. 34*:2633–2638 (1991).
Glennon, R.A. and Malgorzata, D., *Pharmacol. Biochem. Behav. 40*:1009–1017 (1991).
Glennon, R.A. et al., *J. Med. Chem. 34*:1855–1859 (1991).
Glennon, R.A. et al., *J. Med. Chem. 34*:1094–1098 (1991).
Glennon, R.A. et al., *Pharmacol. Biochem. Behav. 37*:557–559 (1990).
Glennon, R.A., *NIOA Res. Monogr. 94*:Pharmacol. Toxicol. Amphetamine Relat. Des. Drugs, pp. 43–67 (1989).
Glennon, R.A. and Seggel, M.R., *ACS Symp. Ser. 413*:264–280 (1989).
Glennon, R.A. and Misenheimer, B.R., *Pharmacol. Biochem. Behav. 33*:909–912 (1989).
Glennon, R.A. et al., *J. Med. Chem. 32*:1921–1926 (1989).
Glennon, R.A. et al., *Drug Dev. Res. 16*:335–343 (1989).
Glennon, R.A. et al., *J. Med. Chem. 31*:867–870 (1988).
Glennon, R.A. et al., *Pharmacol. Biochem. Behav. 29*:197–199 (1988).

SIGMA RECEPTOR LIGANDS AND THE USE THEREOF

CROSS REFERENCE TO RELATED APPLICATIONS

The present application is a continuation-in-part of U.S. application Ser. No. 07/720,173, filed Jun. 27, 1991, now abn, which is a continuation-in-part of PCT Application No. PCT/US90/07653, filed Dec. 28, 1990, which is a continuation-in-part of U.S. application Ser. No. 07/495,061, filed Dec. 28, 1990 now U.S. Pat. No. 4,981,974, the contents of which are fully incorporated by reference in their entirety.

FIELD OF THE INVENTION

The invention is in the field of medicinal chemistry. In particular, the invention relates to new compounds having high binding to the sigma receptor and pharmaceutical compositions thereof. These compounds are useful for the treatment of central nervous system disorders and other conditions.

BACKGROUND OF THE INVENTION

Brain sigma receptors are the subject of intense investigation in light of the fact that sigma receptors bind many psychotropic drugs (Sonders et al., *Trends Neurosci.* 11: 37–40 (1988)). Moreover, certain sigma receptor ligands have antipsychotic activity which suggests that sigma receptor active compounds may be used for the treatment of schizophrenia (Largent et al., *Eur. J. Pharmacol.* 11: 345–347 (1988).

Certain neuroleptic (i.e. antipsychotic) agents bind with very high affinity at sigma sites. Su, T., *J. Pharmacol. Exp Ther.* 223: 284 (1982); Tam, S. W., *Proc. Nat. Acad. Sci (USA)* 80: 6703 (1983). One agent with very high affinity for sigma sites (Ki ca 1 nM; i.e., approximately 100-fold higher affinity than N-allyl normetrazocine (NANM)) is the neuroleptic agent haloperidol. Tam, S. W. et al., *Proc. Nat. Acad. Sci (USA)* 81: 5618 (1984). Sigma-opiates, such as NANM, bind with low affinity at typical opiate receptors but bind with significant affinity at PCP receptors.

Current neuroleptic agents are thought to produce their effects via a dopaminergic (DA) mechanism; they display very high affinities for DA binding sites. However, not all of the potent neuroleptic agents bind at [³H]NANM-labelled sigma sites, nor do the sigma-opiates bind at DA sites. This has led to the suggestion that the sites labelled by [³H] NANM be termed sigma-sites and not sigma-opiate sites (i.e., it may simply be coincidental that the sigma opiates possess an opiate-like chemical structure). In addition, there has been speculation that agents with high affinity for sigma sites may either (a) produce psychotic effects (if they behave as agonists), or (b) produce antipsychotic effects (if they behave as antagonists). It has further been speculated that certain neuroleptic agents, such as haloperidol, produce their antipsychotic effects by both a sigma and DA mechanism. Tam, S. W. and Cook, L., *Proc. Nat. Acad. Sci. (USA)* 81: 5618 (1984). In fact, [³H]haloperidol, in combination with spiperone (an agent with high affinity for DA sites and essentially no affinity for sigma sites) is now commonly used to label sigma sites in radioligand binding studies.

A number of researchers have studied the structure-activity relationship of sigma ligands. For example, Manallack, D. T. et al., *Eur. J. Pharmacol.* 144: 231–235 (1987), disclose a receptor model for the phencyclidine and sigma binding sites. Manallack et al. disclose that in a recent SAR study (Largent et al., in press), sigma site affinity was shown to be enhanced by large N-alkyl substituents, e.g., benzyl or phenethyl.

Largent, B. L. et al., *Mol. Pharmacol.* 32: 772–784 (1987), disclose a study of the structural determinants of sigma receptor affinity. In particular, Largent et al. teach that several piperidine and piperazine derivatives have sigma receptor activity. Largent et al. also disclose that affinity for the sigma receptor is markedly influenced by the N-alkyl substituents, with more lipophilic substituents affording greater affinity for the sigma receptor binding sites.

Sharkey, J. et al., *Eur. J. Pharmacol.* 149: 171–174 (1988), studied the sigma receptor binding activity of cocaine-related compounds.

The literature contains a number of suggestions that the sigma receptor is not a single, homogeneous binding site. Bowen, W. D. et al., *Eur. J. Pharm.* 163: 309–318 (1989), disclose that the effect of U.V. radiation on sigma receptor binding depended on the radioligand used to assay for it. It was also demonstrated that the binding characteristics of several sigma ligands were different in membranes from certain cell lines than in guinea pig brain membranes. (Hellewell, S. B. and Bowen, W. D., *Brain Res.* 527: 224–253 (1990); Wu, X.-Z. et al., *J. Pharmacol. Exp. Ther.* 257: 351–359 (1991)). At least two groups have reported significantly different pharmacology for "sigma receptors" when using different radioligands to label these sites. (Itzhak, Y. et al., *J. Pharmacol. Exp. Ther.* 257: 141–148 (1991); Karbon, E. W. et al., *Eur. J. Pharm.* 93: 21–27 (1991)). In addition, [³H]DTG binding was found to have two components in guinea pig membranes (Rothman, R. B. et al., *Mol. Pharm.* 39: 222–232 (1991)). An overlap of sigma sites with some of the multiple sites labeled by [³H]dextromethorphan has also been described (Musacchio, J. M. et al., *Life Sci.* 45: 1721–1732 (1989)).

Hellewell and Bowen, *Brain Res.* 527: 224–253 (1990), were the first to define the characteristics of the two putative sigma receptor subtypes, named sigma-1 and sigma-2. The primary pharmacological distinction between these tow sites is the affinity of the (+) isomers of the benzomorphan opiates for the binding sites. These compounds, such as (+)SKF 10,047 and (+)pentazocine show nearly two orders of magnitude higher affinity for the sigma-1 site compared to the sigma-2 site. The (–) isomers of the benzomethorphans show little selectivity between these two sites. Other distinctions noted between the two sites are a preponderance of the sigma-2 sites in cell lines such as NCB-20, PC12 and NG108-15 cells (Hellewell, S. B. and Bowen, W. D., *Brain Res.* 527: 224–253 (1990); Wu, X.-Z. et al., *J. Pharmacol. Exp. Ther.* 257: 351–359 (1991); Georg, A. and Friedl, A., *J. Pharmacol. Exp. Ther.* 259: 479–483 (1991); Quirion, R. et al., *Trends in Pharmacological Sciences* 13: 85–86 (1992)).

There has been considerable research on amphetamine and amphetamine derivatives. For example, Aldous, F. A. B., *J. Med. Chem.* 17: 1100–1111 (1974), discloses a structure-activity study of psychotomimetic phenylalkylamines. Aldous et al. also disclose a number of halo, methyl, and methoxy substituted amphetamines.

Fuller, R. W. et al., *J. Med. Chem.* 14: 322–325 (1971), disclose amphetamine derivatives substituted on the 3- and 4-positions of the aromatic ring with one or more chloro, fluoro, alkyl, phenoxy, alkoxy and hydroxy substituents.

Foye, W. O. et al., *J. Pharm. Sci.* 68: 591–595 (1979), disclose heterocyclic analogues of amphetamine having 2-furyl, 2-thienyl, 3-methyl-2-phenol, 3-pyridyl, 6-methyl-2-pyridyl, 4-chlorophenyl, and 1-naphthyl rings.

Boissier, J. R. et al., *Chem. Abstr.* 66: 46195h (1967), disclose N-benzyl amphetamine derivatives of the Formula (I):

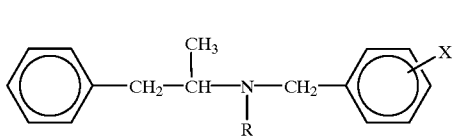

(I)

wherein X is methyl, $CF_3$, methoxy, or a halogen and R is hydrogen or methyl. These compounds reportedly have anoretic activity and low toxicity. Particular compounds disclosed by Boissier et al. include N-(1-phenyl-2-propyl)-4-chlorobenzylamine, N-(1-phenyl-2-propyl)-4-methylbenzyl-amine, and N-(1-phenyl-2-propyl)-4-methoxybenzylamine.

Boissier, J. R. et al., *Chem. Abstr.* 67: 21527a (1967), disclose amphetamine derivatives of the Formula (II):

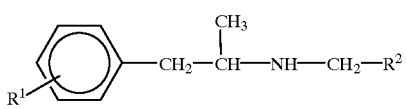

(II)

wherein $R^1$ is hydrogen, 4-Cl, 3-Cl, or 3-$CF_3$ and $R^2$ is 2-chlorophenyl, 4-chlorophenyl, 4-bromophenyl, 3-$CF_3$-phenyl, 4-tolyl, 4-methoxyphenyl, phenyl, 2-furyl, 2-tetrahydrofuryl, 2-thienyl, or 3-thienyl. Reportedly, these compounds were tested for anorexigenic activity in rats and dogs.

Osbond, J. M. et al., *Chem. Abstr.* 69: 51816c (1968), disclose N,N-bis-(omega-phenylalkyl)amines having the Formula (III):

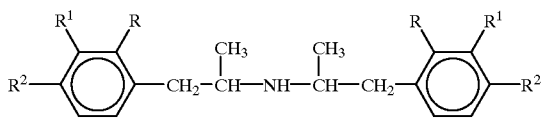

(III)

wherein $R^1$, $R^2$, and $R^3$ are hydrogen, chloro, $CF_3$, or methoxy.

Gosztonyi, T. et al., *J. Label. Comp. Radiopharm.* 8: 293–303 (1977), disclose the preparation of N-substituted omega-haloalkyl derivatives of p-chloro amphetamine. Also disclosed, is the corresponding omega-hydroxyalkyl amine.

Coutts, R. T. et al., *Can. J. Microbiol.* 26: 844–848 (1980), disclose N-substituted p-chloro amphetamines having the following Formula (IV):

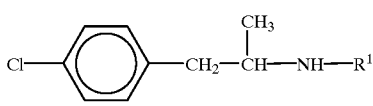

(IV)

wherein $R^1$ is 2-butanone-3-yl, 2-hydroxybutane-3-yl, 1-hydroxybutane-3-yl, or acetate.

Fuller, R. W. et al., *J. Pharm. Pharmacol.* 5: 828–829 (1973), disclose lipid-soluble derivatives of amphetamine comprising 2-chloro, 3-chloro, 4-chloro, and beta, beta-difluoro-amphetamine, and the effect thereof on amphetamine levels in the brain.

Fuller, R. W. et al., *Neuropharmacology* 14: 739–746 (1975), disclose 4-chloroamphetamine, 4-bromoamphetamine, and 4-fluoroamphetamine and the effect thereof on serotonin metabolism.

Conde, S. et al., *J. Med. Chem.* 21: 978–981 (1978), disclose thiophene analogues of chloroamphetamine having the following Formula (V):

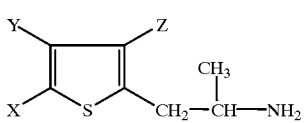

(V)

wherein X, Y, and Z are chloro or hydrogen, and the effect thereof on serotonin levels in the brain.

Lukovits, I., *Int. J. Quantum. Chem.* 20: 429–438 (1981), discloses various halo, methyl, and methoxy ring-substituted amphetamines, and the inhibitory potencies thereof on phenylethanolamine-N-methyl transferase.

Law, B., *J. Chromatog.* 407: 1–18 (1987), discloses amphetamine analogues comprising 1-methyl-2-(2'-naphthyl)ethylamine, N-isopropyl-2-(2'-naphthyl)ethylamine, and N-isopropyl-2-phenylethylamine.

Johansson, A. M. et al., *J. Med. Chem.* 30: 602–611 (1987), disclose N-substituted 2-aminotetralins of the Formula (VI):

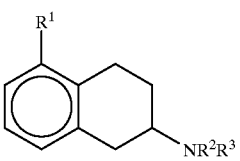

(VI)

wherein $R^1$ is OH or OMe and $R^2$ and $R^3$ are H or $C_1$–$C_4$ lower alkyl. These compounds were tested for dopamine receptor agonist and antagonist activities.

Hacksell, U. et al., *J. Med. Chem.* 22: 1469–1475 (1979), disclose N-alkylated-2-aminotetralins of the Formula (VII):

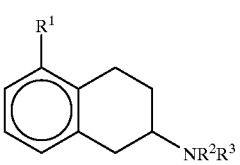

(VII)

wherein $R^1$ is OH or OMe, $R^2$ is lower alkyl, and $R^3$ is lower alkyl or phenethyl. In particular, Hacksell et al., disclose two aminotetralins of the Formulae (VIII) and (IX):

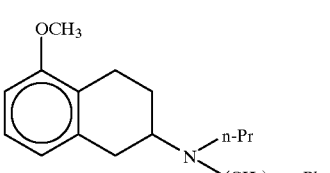

(VIII)

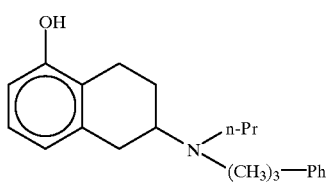

These compounds reportedly have dopamine-receptor stimulating activity.

McDermed, J. D. et al., *J. Med. Chem.* 18: 362–367 (1975), disclose N-alkyl aminotetralins of the Formula (X):

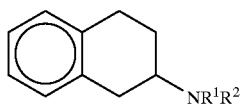

wherein $R^1$ and $R^2$ is one of a large number or alkyl, heteroalkyl, and alkaryl groups. In particular, McDermed et al. disclose two compounds of the Formula (XI) and (XII):

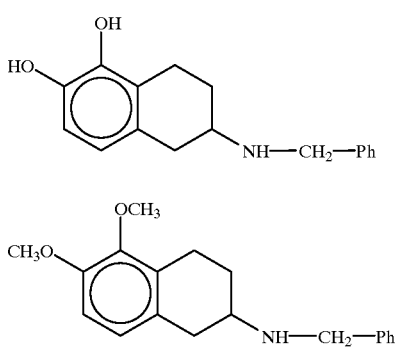

These compounds are reportedly dopamine receptor agonists.

Glennon, R. A. et al., *Pharmacol. Biochem. Behav.* 21: 895–901 (1984), disclose that 2-aminotetralin is a conformationally restricted analog of amphetamine which is about one-half as effective as racemic amphetamine.

Beaulieu, M. et al., *Eur. J. Pharmacol.* 105: 15–21 (1984), disclose N,N,-disubstituted 2-aminotetralins of the Formula (XIII):

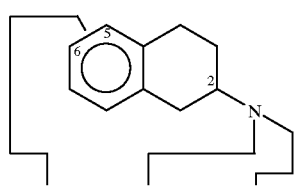

| 5-OH | H | H |
| 5-OH | H | $C_3H_7$ |
| 5-OH | $C_3H_7$ | $C_3H_7$ |

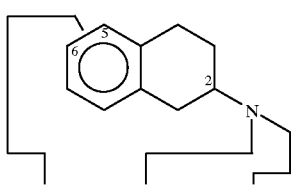

| 5-OH | $C_3H_7$ | 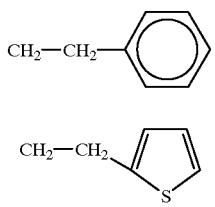 |
| 5-OH | $C_3H_7$ | 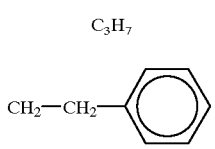 |
| 5-H | $C_3H_7$ | $C_3H_7$ |
| 5-H | $C_3H_7$ | 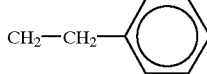 |
| 5,6 OH | H | H |
| 5,6 OH | $C_3H_7$ | $C_3H_7$ |

These compounds are reportedly potent D-2 dopamine receptor agonists.

Naiman, N. et al., *J. Med. Chem.* 32: 253–256 (1989), disclose 2-(alkylamino)tetralin derivatives of the Formula (XIV):

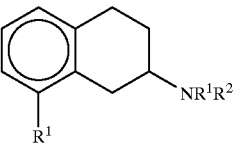

wherein

R is H, OMe, or OBz;

$R^1$ is H, Me, or n-Pr; and $R^2$ is H, n-propyl, benzyl, phenethyl, or phenpropyl.

These compounds reportedly bind to the $5\text{-HT}_{1A}$ receptor site.

Beecroft, R. A. et al., *Tetrahedron* 41: 3853–3865 (1985), disclose N,N-disubstituted piperazines having the Formulae (XV)–(XVIII):

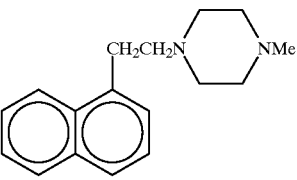

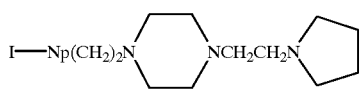
(XVI)

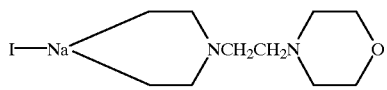
(XVII)

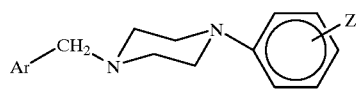
(XVIII)

where Ar = 1,2-Naphthyl or 9-Anthyl
and Z = H,2-OMe or 4-OMe

Fuller, R. W. et al., *J. Pharmacol. Exp. Therapeut.* 218: 636–641 (1981), disclose substituted piperazines having the following Formulae (XIX) and (XX):

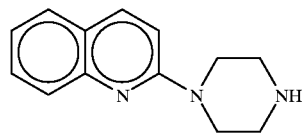
(XIX)

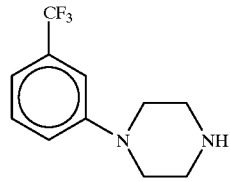
(XX)

which reportedly act as serotonin agonists and inhibit serotonin uptake or serotonin oxidation.

Fuller, R. W. et al., *Res. Commun. Chem. Pathol. Pharmacol.* 29: 201–204 (1980), disclose the comparative effects on 5-hydroxyindole concentration in rat brain by p-chloroamphetamine and 1-(p-chlorophenol)piperazine having the following Formulae (XXI) and (XXII):

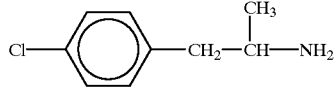
(XXI)

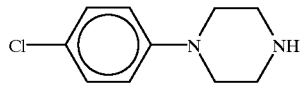
(XXII)

Boissier, J. et al., *Chem. Abstr.* 61: 10691c, disclose disubstituted piperazines having the Formula (XXIII):

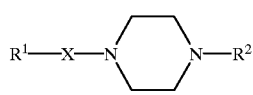
(XXIII)

wherein $R^1$ and $R^2$ are aryl and X is a straight or branched chain alkylene of $C_1$–$C_3$. The compounds are reportedly adrenolytics, hypotensors, potentiators of barbiturates, and depressants of the central nervous system.

Roessler, *Chem Abstr.* 61: 13328g, disclose piperazine derivatives of the Formula (XXIV):

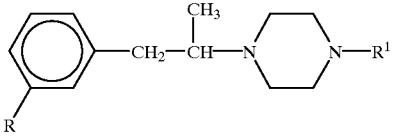
(XXIV)

wherein R=H or methoxy and $R^1$=H, o-ethylphenyl, or p-chlorophenyl.

Ruschig, H et al., *Chem. Abstr.* 53: 3253e, disclose a large series of N,N-disubstituted piperazines including 1-benzyl-4-(3-chloro-4-methylphenyl)piperazine.

Shvedov, V. I. et al., *Chem. Abstr.* 73: 11806q (1970), disclose 4-($R^2CH_2$—$CH_2$ substituted)-1-phenyl-piperazines wherein $R^2$ is phenyl, 2-naphthyloxy, 3-indolyl, 2-methyl-3-indolyl or 2-benzimidazolyl.

Popov, D., *Chem. Abstr.* 67: 54102m (1967), disclose disubstituted piperazines of the Formula (XXV):

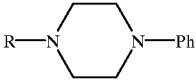
(XXV)

wherein R is tolyl, p-methoxyphenyl, m-ethoxyphenyl, beta-naphthyl, m-or p-carboxylphenyl, 3,4-dimethoxyphenyl, 5-hydrindenyl, p-chloro-phenyl, p-bromophenyl, p-iodophenyl, 3,4-dichlorophenyl, and m- or p-nitrophenyl.

Glennon, R. A et al., *J. Med. Chem.* 31: 1968–1971 (1988), disclose various N,N-disubstituted piperazines having the Formulae (XXVI)–(XXIX):

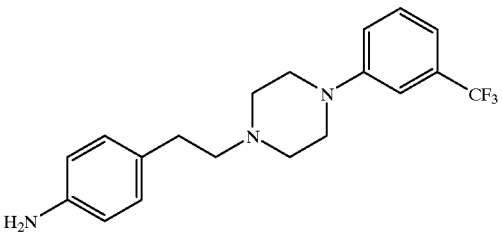
(XXVI)

(XXVII)

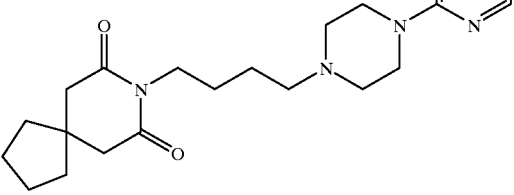

-continued (XXVIII)

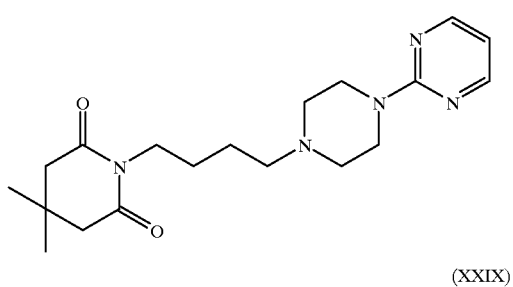

(XXIX)

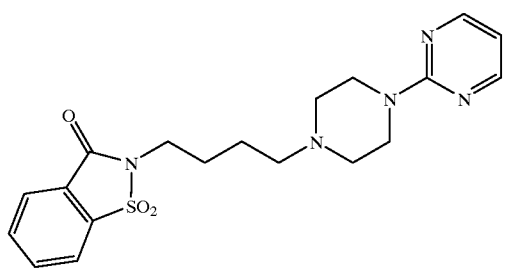

These compounds reportedly have high affinity for the 5-HT$_{1A}$ serotonin binding site.

Prasad, R. N. et al., *J. Med. Chem.* 11: 1144–1150 (1968), disclose N,N-disubstituted piperazines of the Formula (XXX):

(XXX)

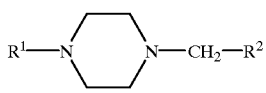

wherein R$^1$ is phenyl or o-methoxyphenyl and R$^2$ is 2,4-dichlorophenyl, o-, m- or p-methoxyphenyl, 3,4-dimethoxyphenyl, or m-tolyl. These compounds are reported to be antihypertensive agents.

Despite the development of the above-mentioned derivatives, a need continues to exist for new sigma receptor ligands and for methods for the treatment of central nervous system disorders.

SUMMARY OF THE INVENTION

The invention relates to the discovery that certain phenylalkyl-amine, aminotetralin, piperazine, piperidine and related derivatives have high binding to the sigma receptor and, unexpectedly, low binding for the PCP, DA and 5-HT$_{1A}$ receptors. Thus, the sigma receptor ligands of the present invention can be used for the treatment of central nervous system disorders and drug abuse without the side effects of traditional neuroleptic agents which also bind to the DA and 5-HT$_{1A}$ receptors.

The invention also relates to the discovery that certain phenylalkyl-amines, aminotetralins, piperazines, piperidines and related derivatives have selective binding for the sigma-1 binding site while others have selective binding to the sigma-2 binding site. Compounds which bind to the sigma-1 binding site are useful in treating gastrointestinal disorders, and are not associated with dystonic effects which are associated with binding to the sigma-2 binding site. In contrast, compounds which selectively bind to the sigma-2 binding site may block calcium channels. Thus, such calcium channel blocking sigma-2 receptor ligands may be used to treat psychosis, angina, migrane and hypertension.

The sigma receptor ligands of the present invention may also be employed in methods of treating or preventing depression.

In particular, the invention relates to methods of treating a human being suffering from central nervous system disorders, drug abuse, gastrointestinal disorders, hypertension, migrane, angina and depression, which comprises administering to said human a therapeutically effective amount of a compound selected from the Formulae (XXXI) and (XXXII):

(XXXI)

(XXXII)

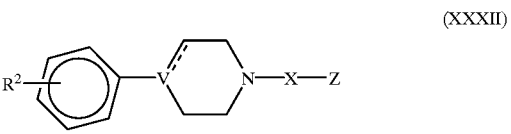

wherein said compound exhibits high binding activity with respect to the sigma receptor.

The invention also relates to certain novel sigma receptor ligands defined by Formulae (XXXI) and (XXXII) as well as pharmaceutical compositions comprising these novel sigma receptor ligands.

Surprisingly, the present inventor has discovered that certain N-substituted phenylalkylamines, although seemingly related to amphetamine, have activities which are, in fact, very much unlike amphetamine. Instead, the N-substituted phenylalkylamines have high affinity to the sigma receptors and low affinity to the DA and PCP receptors. In addition, certain of the sigma receptor ligands of the present invention have unexpectedly low affinity for the 5-HT$_{1A}$ receptor. In addition, certain of the sigma receptor ligands of the present invention are highly selective for the sigma-1 binding site over the sigma-2 binding site. The discovery of such ligands having high affinity for the sigma receptors, in particular the sigma-1 receptor, and low affinity for other such receptors allows for the treatment of psychosis, drug abuse, gastrointestinal disorders, and depression, and other conditions without untoward side effects. In contrast, compounds which are selective for the sigma-2 receptor are useful for the treatment of psychosis, hypertension, migrane and angina.

DESCRIPTION OF THE PREFERRED EMBODIMENTS

The invention relates to a method of treating a human being suffering from central nervous system disorders, drug abuse, gastrointestinal disorders, hypertension, migrane, angina and depression, which comprises administering to said human a therapeutically effective amount of a compound having the Formula (XXXI):

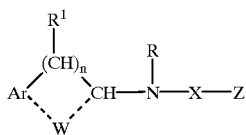

(XXXI)

wherein:
Ar is aryl or heteroaryl wherein aryl or heteroaryl can be substituted by hydrogen, halogen such as chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3$–$C_6$ heterocycloalkyl, a $C_3$–$C_6$ heterocycloalkyl ring fused to a benzene ring, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

R is hydrogen or $C_1$–$C_6$ alkyl;

$R^1$ is independently selected from the group consisting of hydrogen, $C_1$–$C_6$ alkyl, hydroxy, amino, $C_1$–$C_6$ alkylamino or =O (a double bonded oxygen); or R and $R^1$ together form a morpholino ring;

n is 0–5;

W is —$(CH_2)_p$— or —H H—, wherein p is 1–3;

X is —$(CH_2)_q$—, wherein q is 1–6;
—$(CH_2)_r$—C≡C—$(CH_2)_r$—, wherein each r is 0–3 independently;
—$(CH_2)_r$—CH=CH—$(CH_2)_r$—;

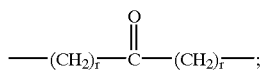

—$(CH_2)_r$—Y—$(CH_2)_r$—, wherein Y is O or S; or
$C_1$–$C_6$ alkyl (wherein Z is hydrogen);

Z is hydrogen, aryl, an aryl-substituted carboxylic acid group, heteroaryl or cycloalkyl, wherein aryl, heteroaryl and cycloalkyl can be substituted by hydrogen, halogen such as chloro, fluoro, bromo, iodo; $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl or an ortho methylene dioxy group;

wherein said compound exhibits high binding activity with respect to the sigma receptors.

The invention also relates to methods of treating central nervous system disorders, drug abuse, gastrointestinal disorders, hypertension, migraine, angina and depression, using compounds having the Formula (XXXIII):

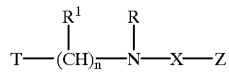

(XXXIII)

wherein T is a cycloalkyl group or Ar as described above, n, R, and $R^1$, X and Z are defined above;

wherein said compound exhibits high binding activity with respect to the sigma receptors.

Especially preferred compounds within the scope of Formula (XXXIII) include N-phenethyl-1-phenyl-isopropylamine, N-phenylpropyl-1-phenylisopropylamine, N-(2-phenoxyethyl)-1-phenylisopropylamine, N-(3-phenyl-3-propanon-1-yl)-1-phenylisopropylamine, N-(4-phenylbutyl)-1-phenylisopropylamine, N-(3-(1-naphthyl)propyl)-1-phenylisopropylamine, N-(3-(2-naphthyl)propyl)-1-phenylisopropylamine, N-(3-phenyl-2-propyn-1-yl)-1-phenylisopropylamine, N-(3-phenylpropyl)-3-(4-hydroxyphenyl)isopropylamine, N-(3-phenylpropyl)-3-(4-methoxyphenyl)isopropylamine, N-(3-phenylpropyl)-3-(3-bromophenyl)isopropylamine, N-(3-phenylpropyl)-3-(4-bromophenyl)isopropylamine, N-(3-phenylpropyl)-3-(3,4-dichlorophenyl)isopropylamine, N-(3-phenylpropyl)-3-(4-iodophenyl)isopropylamine, N-(3-phenylpropyl)-3-(3-trifluoromethyl-phenyl)isopropylamine, N-(2-phenethyl)-N-methyl-1-phenylisopropyl-amine, N-(3-phenylpropyl)-1-phenylpropan-1-one-2-amine, N-(2-indane)-3-phenylisopropylamine, N-(2-indane)-3-phenylpropylamine, N,N-di-((3-phenyl)propyl)amine, N-(2-(1-naphthyl)ethyl)-1-phenylisopropylamine, N-(2-(2-naphthyl)ethyl)-1-phenylisopropylamine, N-(2-(1-naphthyl)propyl)-1-phenylisopropylamine, N-(2-(2-naphthyl)propyl)-1-phenylisopropylamine, N-(3-phenylpropyl)-1-phenyl-2-pentylamine, N-(3-phenylbutyl)-1-phenyl-2-butylamine, N,N-di-(2-ethylphenyl)methylamine, N,N-dibenzylamine, N-(3-phenylpropyl)-N-(6-phenylhexyl)amine, N-(3-phenylpropyl)-N-(5-phenylpentyl)amine, N-propyl-N-methyl-5-phenylpentylamine, N-methyl-N-(3-phenylpropyl)-1-isopropylamine, N-methyl-N-(3-methyl-2-butenyl)-1-isopropylamine, N-methyl-N-(3-methylbutyl)-1-isopropylamine, N-methyl-N-(3-phenylbutyl)-1-phenyl-2-pentylamine, N-propyl-N-(3-phenyl)propyl)-1-phenyl-2-propylamine, N-benzyl-N-(3-phenyl)propyl)-1-phenyl-2-propylamine, N-phenyl-(5-phenyl)pentylamine, N-methyl-N-(3-phenyl)propyl-5-phenylpentylamine, N-(2-(o-methylphenyl)ethyl)-5-phenylpentylamine, N-(2-(m-methylphenyl)ethyl)-5-phenylpentylamine, N-(2-(p-methylphenyl)ethyl)-5-phenylpentylamine, N-benzyl-5-phenylpentylamine, N-benzyl-N-methyl-5-phenylpentylamine, N-(2-(3-hydroxyphenyl)ethyl)-5-phenylpentylamine, N-(2-(2-hydroxyphenyl)ethyl)-5-phenylpentylamine, N,N'-diethyl-2-(diphenylacetoxy)ethylamine, N,N'-diethyl-2-(fluorenecarboxy)ethylamine, N,N-Dimethyl-5-phenylpentylamine, N-Benzyl-N-(3-phenylpropyl)-1-phenyl-2-propylamine, N-Benzyl-N-methyl-5-phenylpentylamine, N-Benzyl-5-phenylpentylamine, and N-(2-phenethyl)-N-methylpentylamine.

The invention also relates to methods of treating central nervous system disorders, drug abuse, gastrointestinal disorders, hypertension, migraine, angina and depression, with compounds related to Formula (XXXII) where W is
—(CH$_2$)$_p$— having the Formula (XXXIV):

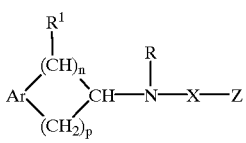

(XXXIV)

wherein Ar, n, p, R, R$^1$, X and Z are as defined above; and wherein said compound exhibits high binding activity with respect to the sigma receptors.

The invention also relates to methods of treating central nervous system disorders, drug abuse, gastrointestinal disorders, hypertension, migrane, angina and depression, with compounds of the Formula (XXXII):

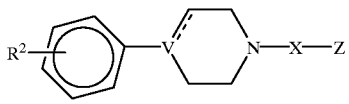

(XXXII)

wherein X and Z are as defined above and V is N or —CM—, wherein M is hydrogen, C$_1$–C$_6$ alkyl, C$_1$–C$_6$ alkoxy, hydroxy, fluoro, chloro, bromo, trifluoromethyl, or represents one half of a double bond (with the neighboring endocyclic carbon);

R$^2$ is independently selected from the group consisting of hydrogen, chloro, fluoro, bromo, iodo, CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, aryl, substituted aryl, heteroaryl, substituted heteroaryl, C$_3$–C$_6$ heterocycloalkyl, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, dialkylamino, hydroxy, carbamoyl, C$_1$–C$_6$ N-alkylcarbamoyl, C$_2$–C$_{15}$ N,N-dialklcarbamoyl, nitro and C$_2$–C$_{15}$ dialkylsulfamoyl; and wherein said compound exhibits high binding activity with respect to the sigma receptors.

Preferably, the invention relates to the treatment of central nervous system disorders, drug abuse, gastrointestinal disorders, hypertension, migrane, angina and depression, with a piperidine derivative having Formula (XXXV):

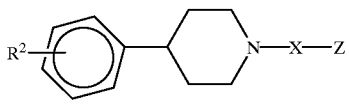

(XXXV)

wherein R$^2$, X and Z are as defined above.

The invention also relates to the treatment of central nervous system disorders, drug abuse, gastrointestinal disorders, hypertension, migrane, angina and depression, with compounds having the Formula (XXXIX):

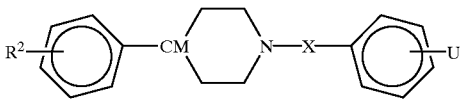

(XXXIX)

wherein

R$^2$, M, X and Z are as defined above;

U is selected from the group consisting of hydrogen, halogen such as chloro, fluoro, bromo, iodo;

CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, C$_3$–C$_6$ heterocycloalkyl, a C$_3$–C$_6$ heterocycloalkyl ring fused to a benzene ring, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, C$_2$–C$_{15}$ dialkylamino, hydroxy, carbamoyl, C$_1$–C$_6$ N-alkylcarbamoyl, C$_2$–C$_{15}$ N,N-dialkylcarbamoyl, nitro and C$_2$–C$_{15}$ dialkylsulfamoyl;

wherein said compound exhibits high binding activity with respect to the sigma receptors.

The invention also relates to a method of treating a human being suffering from central nervous system disorders, drug abuse, gastrointestinal disorders, hypertension, migrane, angina and depression, which comprises administering to said human a therapeutically effective amount of a compound of the Formula (XXXVa):

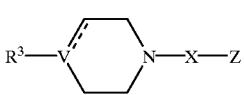

(XXXVa)

wherein:

R$^3$ is selected from the group consisting of C$_1$–C$_6$ alkyl, C$_1$–C$_6$ alkenyl, C$_2$–C$_6$ dialkoxymethyl, C$_3$–C$_{15}$ dialkylaminoalkyl, aralkyl, C$_3$–C$_6$ cycloalkyl, aroyl, C$_2$–C$_6$ acyl, aryl, substituted aryl, heteroaryl, substituted heteroaryl, C$_3$–C$_6$ heterocycloalkyl; and X, Y and Z are defined above, wherein said compound exhibits a high binding activity with respect to the sigma receptors.

Especially preferred compounds within the scope of Formula (XXXVa) include N-methyl-N'-(4-phenyl-3-(E)butenyl)piperazine, N-methyl-N'-(4-phenyl-3-(Z)butenyl)-piperazine, N-methyl-N'-(4-(3-trifluoromethylphenyl)-3-(Z)butenyl)piperazine, N-methyl-N'-(4-phenylbutyl)piperazine, N-benzyl-N'-(4-phthalimidobutyl)piperazine, N-(2-methoxyphenyl)-N'-(4-phthalimidobutyl)piperazine, N-(5-phenylpentyl)-4-benzylpiperidine, N-(5-phenylpentyl)-4-benzyl-4-hydroxy-piperidine, N-benzyl-N'-(5-phenyl)pentylpiperazine and N,N'-di-(5-phenyl)pentylpiperazine.

The invention also relates to a method of treating a human being suffering from central nervous system disorders, drug abuse, gastrointestinal disorders, hypertension, migrane, angina and depression, which comprises administering to said human a therapeutically effective amount of a compound of the Formula (XXXVb):

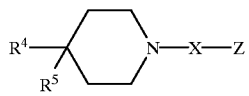

(XXXVb)

wherein:

R$^4$ is hydrogen or an aryl group substituted with a group selected from the group consisting of C$_1$–C$_6$ alkyl, C$_1$–C$_6$ alkenyl, C$_2$–C$_6$ dialkoxymethyl, C$_3$–C$_{15}$ dialkylaminoalkyl, aralkyl, C$_3$–C$_6$ cycloalkyl, aroyl, C$_2$–C$_6$ acyl, aryl, substituted aryl, heteroaryl, substituted heteroaryl, C$_3$–C$_6$ heterocycloalkyl;

R$^5$ is hydrogen or hydroxy; and

X, Y and Z are defined above, wherein said compound exhibits a high binding activity with respect to the sigma receptors.

Examples of compounds having Formula (XXXVb) include but are not limited to N-(5-phenylpentyl)piperidine, N-(8-phenylheptyl)piperidine, N-(5-(4-methoxyphenyl)pentyl)piperidine, N-(3-phenylpropyl)piperidine, N-(5-cyclohexyl)pentylpiperidine N-benzylpiperidine, N-(2-phenethyl)-4-hydroxy-4-phenylpiperidine N-(2-phenethyl)-4-hydroxy-4-t-butylpiperidine, N-(5-(4-chlorophenyl)-5-pentanon-1-yl)piperidine, N-(5-(4-chlorophenyl)-5-pentanon-1-yl)-4-phenylpiperidine, N-(5-(4-methoxyphenyl)-5-pentanon-1-yl)piperidine, N-(5-(4-methoxyphenyl)-5-pentanon-1-yl)-4-phenylpiperidine, N-(5-(4-methoxyphenyl)pentyl)-4-phenylpiperidine, N-(5-phenyl-5-pentanon-1-yl)-4-phenylpiperidine N-(5-(4-chlorophenyl)pentyl)-4-phenylpiperidine, N-(5-(3-methoxyphenyl)-5-pentanon-1-yl)piperidine, N-(5-(3-chlorophenyl)-5-pentanon-1-yl)piperidine, N-(5-(3-chlorophenyl)-5-pentanon-1-yl)-4-phenylpiperidine, N-(5-(3-methoxyphenyl)-5-pentanon-1-yl)-4-phenylpiperidine, N-(4-(4-fluorophenyl)-4-butanon-1-yl)piperidine, N-(5-(4-fluorophenyl)-5-pentanon-1-yl)piperidine N-(5-(4-fluorophenyl)-5-pentanon-1-yl)-4-phenylpiperidine, N-(5-(4-fluorophenyl)-5-pentanon-1-yl)-4-(3-chlorophenyl)-4-hydroxypiperidine, N-(5-(4-chlorophenyl)-5-pentanon-1-yl)-4-(4-fluorophenyl)-1,2,3,6-terahydropyridine, N-(5-(4-chlorophenyl)-5-pentanon-1-yl)-4-(4-fluorophenyl)piperidine, N-(5-(4-chlorophenyl)-5-pentanon-1-yl)-4-(4-fluorophenyl)-1,2,3,6-terahydropyridine, N-(5-(4-chlorophenyl)-5-pentanon-1-yl)-4-(4-fluorophenyl)piperidine, N-(5-(4-chlorophenyl)-5-pentanon-1-yl)-4-(chlorophenyl)-1,2,3,6-terahydropyridine, N-(5-(4-chlorophenyl)-5-pentanon-1-yl)-4-(chlorophenyl)piperidine N-(5-(3,4-dichlorophenyl)-5-pentanon-1-yl)-4-(chlorophenyl)piperidine, N-(5-cyclopentylpentan-5-on-1-yl)piperidine and N-(5-(3,4-methylenedioxyphenyl)penta-2,4-dienyl)piperidine.

The invention also relates to a method of treating a human being suffering from central nervous system disorders, drug abuse, gastrointestinal disorders, hypertension, migrane, angina and depression, which comprises administering to said human a therapeutically effective amount of a compound of the Formula (XXXVc):

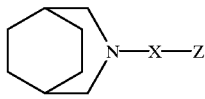

(XXXVc)

wherein X and Z are defined above, wherein said compound exhibits a high binding activity with respect to the sigma receptors.

An example of a compound having Formula XXXVc is N-(5-phenyl)pentyl-3-azabicyclo[3.2.2]nonane.

The invention also relates to a method of treating a human being suffering from central nervous system disorders, drug abuse, gastrointestinal disorders, hypertension, migrane, angina and depression, which comprises administering to said human a therapeutically effective amount of a tropane derivative of the Formula (XXXVd):

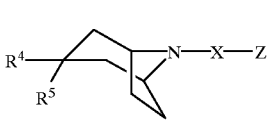

(XXXVd)

wherein R$^4$, R$^5$, X and Z are defined above, and wherein said compound exhibits a high binding activity with respect to the sigma receptors.

An example of compounds having Formula (XXXVd) include N-(5-phenyl)pentyl-4-phenyltropan-4-ol.

The invention also relates to the treatment of central nervous system disorders, drug abuse, gastrointestinal disorders, hypertension, migrane, angina and depression, by administering a compound related to those of Formula XXXIII and having the Formula (XXXVI):

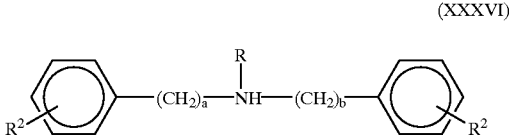

(XXXVI)

wherein a is 1–8;

b is 1–8;

R is as defined above;

wherein said compound exhibits high binding activity with respect to the sigma receptors.

Preferably, compounds which are useful for the treatment of central nervous system disorders, drug abuse, gastrointestinal disorders, hypertension, migrane, angina and depression, and which are within the scope of Formula (XXXI) are naphthyl derivatives having Formula (XXXVII):

(XXXVII)

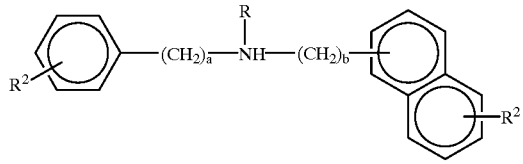

wherein R, $R^2$, a and b, as defined above, may be the same or different;

wherein said compound exhibits high binding activity with respect to the sigma receptors.

Other compounds useful for the treatment of central nervous system disorders, drug abuse, gastrointestinal disorders, hypertension, migrane, angina and depression, include morpholino derivatives having Formula (XXXVIII):

(XXXVIII)

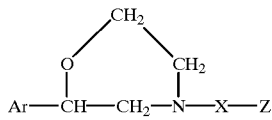

wherein Ar, X and Z are defined above;

wherein said compound exhibits high binding activity with respect to the sigma receptors.

Other compounds useful for the treatment of central nervous system disorders, drug abuse, gastrointestinal disorders, hypertension, migrane, angina and depression, include cycloalkyl derivatives having Formula (LII)

(LII)

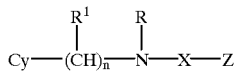

wherein Cy is $C_3$–$C_8$ cycloalkyl and Ar, $R^1$, n, R, X, and Z are defined as above. Examples of compounds having Formula LII include 5-cyclohexylpentylamine, N-methyl-5-cyclohexylpentylamine, N,N-Dimethyl-5-cyclohexylpentylamine, N-cyclohexylmethyl-5-cyclohexyl-n-pentylamine, and N-cyclohexylmethyl-N-methyl-5-cyclohexyl-n-pentyl amine.

Other compounds useful for the treatment of central nervous system disorders, drug abuse, gastrointestinal disorders, hypertension, migrane, angina and depression, includes compounds of the Formula (LIII)

(LIII)

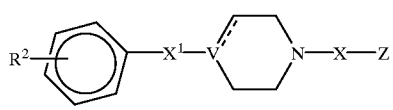

wherein $X^1$ is —$(CH_2)_r$—C≡C—$(CH_2)_r$—, wherein each r is 0–3 independently;

—$(CH_2)_r$—CH═CH—$(CH_2)_r$—;

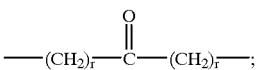

—$(CH_2)_r$—Y—$(CH_2)_r$—, wherein Y is O or S; or
$C_1$–$C_6$ alkyl (wherein Z is hydrogen);
and $R^2$, V, X, and Z are defined as above.

Other compounds useful for the treatment of central nervous system disorders, drug abuse, gastrointestinal disorders, hypertension, migrane, angina and depression, includes compounds of the Formula (LIV):

(LIV)

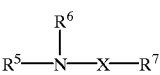

wherein $R^5$ and $R^6$ are independently a $C_{1-8}$ alkyl group, $R^7$ is hydrogen or a $C_{1-8}$ alkyl group substituted by an arylacetoxy group, and X is as defined above. Examples of such compounds include but are not limited to N,N'-diethyl-2-(diphenylacetoxy)ethylamine and N,N'-diethyl-2-(9-fluorenylcarboxy)ethylamine.

The invention is also related to the discovery that the aryl rings of compounds having Formula (LIV) may be missing, and that the compounds still retain high binding to the sigma receptor (Formula (LIV), $R^7$=hydrogen). Such compounds include N,N-dimethyl-n-hexylamine and N-methyl-N-propylhexyl-amine.

The sigma receptor ligands of the present invention may exist in racemic form or in the optically active stereoisomeric form. Most preferably, the compounds exist in the S-(+) form.

The invention also relates to certain novel sigma receptor ligands and pharmaceutical compositions comprising the novel sigma receptor ligands. In particular, the invention relates to compounds having the Formula (XXXI):

(XXXI)

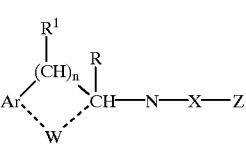

wherein
Ar n, R, $R^1$, W and Z are as defined above and X is
—$(CH_2)_q$—, wherein q is 3–6;
—$(C_2)_r$—C≡C—$(CH_2)_r$—, wherein each r is 0–3 independently;
—$(CH_2)_r$—CH═CH—$(CH_2)_r$—;

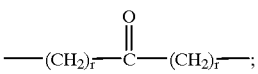

—$(CH_2)_r$—Y—$(CH_2)_r$—, wherein Y is O or S; or
$C_1$–$C_6$ alkyl (wherein Z is hydrogen);
wherein said compound exhibits high binding activity with respect to the sigma receptors.

Sigma receptor ligands having the above Formula (XXXI) wherein q is 3–6 have unexpectedly high binding to the sigma receptors (see Example 2, below). Preferably, q is 5.

The invention also relates to sigma receptor ligands having the Formula (XXXIII):

(XXXIII)
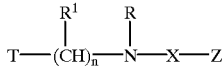

wherein
T, n, R, $R^1$, and Z are defined above, and
X is —$(CH_2)_q$—, wherein q is 3–6;
—$(CH_2)_r$—C≡C—$(CH_2)_r$—, wherein each r is 0–3 independently;

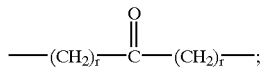

—$(CH_2)_r$—Y—$(CH_2)_r$—, wherein Y is O or S; or
$C_1$–$C_6$ alkyl (wherein Z is hydrogen);
wherein said compound exhibits high binding activity with respect to the sigma receptors.

Sigma receptor ligands having the above Formula (XXXV) wherein q is 3–6 also have unexpectedly high binding to the sigma receptors (see Example 2). Most preferably, q is 5.

The invention also relates to compounds of the Formula (XXXII):

(XXXII)
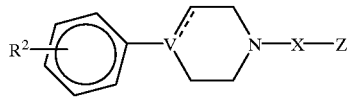

wherein
$R^2$, V and Z are as defined above;
X is —$(CH_2)_r$—C≡C—$(CH_2)_r$—, wherein r is 0–3;
—$(CH_2)_r$—CH=CH—$(CH_2)_r$—;

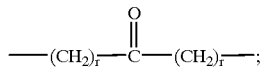

—$(CH_2)_r$—Y—$(CH_2)_r$—, wherein Y is O or S; or
$C_1$–$C_6$ alkyl (wherein Z is hydrogen);
wherein said compound exhibits high binding activity with respect to the sigma receptors.

Sigma receptor ligands having the above Formula (XXXII) wherein q is 3–6 also have unexpectedly high binding to the sigma receptors (see Example 2).

The invention also relates to compounds of the Formula (XXXV):

(XXXV)
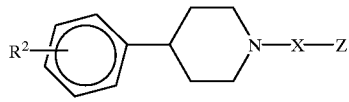

wherein
$R^2$ and Z are as defined above;
X is —$(CH_2)_r$—C≡C—$(CH_2)_r$—, wherein each r is 0–3 independently;

—$(CH_2)_r$—CH=CH—$(CH_2)_r$—;

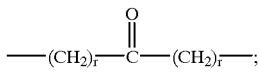

—$(CH_2)_r$—Y—$(CH_2)_r$—, wherein Y is O or S; or
$C_1$–$C_6$ alkyl (wherein Z is hydrogen);
wherein said compound exhibits high binding activity with respect to the sigma receptors.

Sigma receptor ligands having the above Formula (XXXV) also have unexpectedly high binding to the sigma receptors (see Example 2).

The invention also relates to compounds which are related to the Formula XXXII and having the Formula (XXXIX):

(XXXIX)
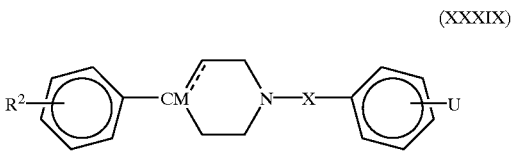

wherein
$R^2$, M, X and Z are as defined above;
U is selected from the group consisting of hydrogen, halogen such as chloro, fluoro, bromo, iodo;
$CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3$–$C_6$ heterocycloalkyl, a $C_3$–$C_6$ heterocycloalkyl ring fused to a benzene ring, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;
wherein said compound exhibits high binding activity with respect to the sigma receptors.

The invention also relates to a compound of the Formula (XXXVa):

(XXXVa)
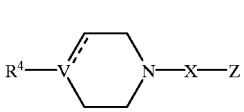

wherein:
$R^3$ is selected from the group consisting of $C_1$–$C_6$ alkyl, $C_1$–$C_6$ alkenyl, $C_2$–$C_6$ dialkoxymethyl, $C_3$–$C_{15}$ dialkylaminoalkyl, aralkyl, $C_3$–$C_6$ cycloalkyl, aroyl, $C_2$–$C_6$ acyl, aryl, substituted aryl, alkaryl, substituted alkaryl, aralkyl, substituted aralkyl, heteroaryl, substituted heteroaryl, $C_3$–$C_6$ heterocycloalkyl; and
X, Y and Z are defined above,
wherein said compound exhibits a high binding activity with respect to the sigma receptors.

The invention also relates to a compound of the Formula (XXXVb):

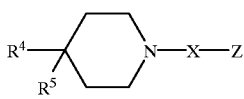

wherein:
R[4] is hydrogen or an aryl group substituted with a group selected from the group consisting of $C_1$–$C_6$ alkyl, $C_1$–$C_6$ alkenyl, $C_2$–$C_6$ dialkoxymethyl, $C_3$–$C_{15}$ dialkylaminoalkyl, aralkyl, $C_3$–$C_6$ cycloalkyl, aroyl, $C_2$–$C_6$ acyl, aryl, substituted aryl, heteroaryl, substituted heteroaryl, $C_3$–$C_6$ heterocycloalkyl;
R[5] is hydrogen or hydroxy; and
X, Y and Z are defined above,
wherein said compound exhibits a high binding activity with respect to the sigma receptors.

The invention also relates to a compound of the Formula (XXXVc):

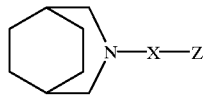

wherein X and Y are defined above,
wherein said compound exhibits a high binding activity with respect to the sigma receptors.

The invention also relates to a tropane derivative of the Formula (XXXVd):

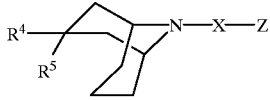

wherein R[4], R[5], X and Z are defined above, and
wherein said compound exhibits a high binding activity with respect to the sigma receptors.

The invention also relates to a compound of the Formula (XXXVI):

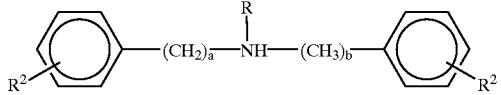

wherein
a is 1–8;
b is 1–8;
R is hydrogen or $C_1$–$C_6$ alkyl;
R[2] is independently selected from the group consisting of hydrogen, chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkyl-amino, dialkylamino, hydroxy, carbamoyl, $C_1$–$C_6$ N-alkylcarbamoyl, $C_2$–$C_{15}$ N,N-dialklcarbamoyl, nitro and $C_2$–$C_{15}$ dialkylsulfamoyl;
wherein said compound exhibits high binding activity with respect to the sigma receptors.

The invention also relates to naphthyl derivatives within the scope of Formula (XXXI) having Formula (XXXVII):

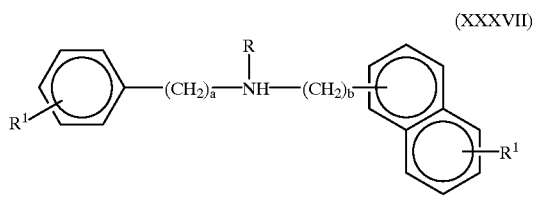

wherein R, R[1], a and b, as defined above, may be the same or different;
wherein said compound exhibits high binding activity with respect to the sigma receptors.

The invention also relates to morpholino derivatives having Formula (XXXVIII):

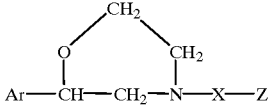

wherein Ar, X and Z are defined above;
wherein said compound exhibits high binding activity with respect to the sigma receptors.

Also as derivatives of compound XXXIII, this invention is concerned with a compound having the Formula (LII)

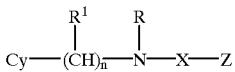

wherein Cy is $C_3$–$C_8$ cycloalkyl and Ar, R[1], n, R, X, and Z are defined as above.

Compounds derived from the Formula XXXII are also an aspect of the present invention. These compounds include a compound of the Formula (LIII)

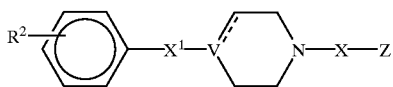

wherein $X^1$ is —$(CH_2)_r$—C≡C—$(CH_2)_r$—, wherein each r is 0–3 independently;
—$(CH_2)_r$—CH=CH—$(CH_2)_r$—;

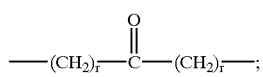

—$(CH_2)_r$—Y—$(CH_2)_r$—, wherein Y is O or S; or
$C_1$–$C_6$ alkyl (wherein Z is hydrogen);
and $R_2$, V, X, and Z are defined as above.

The invention also relates to compounds having the Formula (LIV):

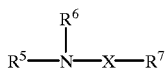

(LIV)

wherein $R^5$ and $R^6$ are independently a $C_{1-8}$ alkyl group, $R^7$ is hydrogen or a $C_{1-8}$ alkyl substituted by an arylacetoxy or arylcarboxy group, and X is as defined above. Examples of compounds having Formula LIV include N,N-dimethyl-n-hexylamine, N-methyl-N-propylhexylamine, N,N'-diethyl-2-(diphenylacetoxy)ethylamine, N,N'-diethyl-2-(fluorenecarboxy)ethylamine, N,N-diethyl-2-(diphenylacetoxy)ethylamine and N,N-diethyl-2-(9-fluorenylcarboxy)ethylamine.

The compounds of the invention have high binding to the sigma receptors. The sigma receptors include both the sigma-1 and sigma-2 subtypes. See Hellewell, S. B. and Bowen, W. D., *Brain Res.* 527: 224–253 (1990); and Wu, X.-Z. et al., *J. Pharmacol. Exp. Ther.* 257: 351–359 (1991). A sigma receptor binding assay which quantitates the binding affinity of a putative ligand for both sigma sites (against $^3$H-DTG, which labels both sites with about equal affinity) is disclosed by Weber et al., *Proc. Natl. Acad. Sci (USA)* 83: 8784–8788 (1986). Alternatively, [$^3$H]pentozocine may be used to selectively label the sigma-1 binding site in a binding assay. A mixture of [$^3$H]DTG and unlabeled (+)pentazocine is used to selectively label the sigma-2 site in a binding assay. The present invention is also directed to certain ligands which are selective for the sigma-1 and sigma-2 receptors. The discovery of such ligands which are selective for one of the two sigma receptor subtypes may be an important factor in identifying compounds which are efficacious in treating central nervous system disorders with minimal side effects.

Typical $C_1$–$C_6$ alkyl groups include methyl, ethyl, n-propyl, i-propyl, n-butyl, t-butyl, i-butyl, pentyl and hexyl groups.

Typical $C_{3-8}$ cycloakyl groups include cyclopropyl, cyclobutyl, cyclopentyl, cyclohexyl, cycloheptyl, and cyclooctyl groups.

Typical $C_2$–$C_6$ carboxylic acyl groups include acetyl, propanoyl, i-propanoyl, butanoyl, s-butanoyl, pentanoyl and hexanoyl groups.

Typical aryl groups include phenyl, naphthyl, phenanthryl, anthracyl and fluorene groups.

Typical aryl-substituted carboxylic acid groups include the above-mentioned carboxylic acyl groups substituted by one or more aryl groups, e.g. diphenylacetoxy and fluorenecarboxy groups.

Typical alkaryl groups include the above-listed aryl groups substituted by one or more $C_1$–$C_6$ alkyl groups.

Typical aralkyl groups include a $C_1$–$C_6$ alkyl group substituted by one of the above-listed aryl groups, e.g. phenethyl, phenylpropyl, phenylbutyl, phenylpentyl and phenylhexyl groups as well as the branched chain isomers thereof.

Typical $C_1$–$C_6$ alkoxycarbonyl groups include carbonyl substituted by methoxy, ethoxy, propanoxy, i-propanoxy, n-butanoxy, t-butanoxy, i-butanoxy, pentanoxy, and hexanoxy groups.

Typical aralkyl groups include the above-listed $C_1$–$C_6$ alkyl groups substituted by phenyl, naphthyl, phenanthryl, and anthracyl groups.

Typical $C_2$–$C_6$ alkenyl groups include vinyl, allyl, 2-butenyl, 2-pentenyl, and 2-hexenyl groups.

Typical $C_2$–$C_6$ alkynyl groups include acetynyl and propargyl groups.

Typical halo groups include fluorine, chlorine, bromine and iodine.

Typical aroyl groups include carbonyl substituted by phenyl, naphthyl, phenanthryl, and anthracyl groups.

Typical aralkanoyl groups include carbonyl substituted by the above-listed aralkyl groups.

Typical aralkoxy groups include the above listed $C_1$–$C_6$ alkoxy groups substituted by phenyl, naphthyl, phenanthyl, and anthracyl groups.

Typical substituted aryl groups include the above-listed aryl groups substituted by halo, hydroxy, $C_1$–$C_6$ alkoxy, amino, and the like.

Typical heteroaryl groups include furyl, thienyl, pyrrolyl, thiazolyl, pyridyl, pyrimidinyl, pyrizinyl, oxazolyl and phthalimido groups which may be fused to a benzene ring.

Typical substituted heteroaryl groups include the above-listed heteroaryl groups substituted by halo, $C_1$–$C_6$ alkyl and the like.

Typical $C_5$–$C_6$ heterocycloalkyl groups include tetrahydrofuranyl, tetrahydropyranyl, piperidinyl, piperazinyl, morpholino and pyrrolidinyl groups.

Under the binding activity studies, an $IC_{50}$ value of at most about 100 nM, preferably at most about 25 nM, more preferably at most 10 nM, most preferably at most 1 nM indicates a high binding affinity with respect to the sigma receptor binding sites. In the present application, the term "high affinity" is intended to mean a compound which exhibits an $IC_{50}$ of less than 100 nM in a sigma receptor binding assay, preferably against $^3$H-DTG as disclosed by Weber et al., *Proc. Natl. Acad. Sci (USA)* 83: 8784–8788 (1986), which measures the binding affinity of compounds toward both the sigma-1 and sigma-2 sites. Especially preferred sigma ligands exhibit $IC_{50}$ values of less than about 25 nM, more preferably less than about 10 nM, most preferably less than about 1 nM against $^3$H-DTG.

The inventor has unexpectedly discovered that certain of the sigma receptor ligand of the present invention exhibit enhanced selectivity to the sigma-1 binding site while other of the sigma receptor ligands exhibit enhanced selectivity to the sigma-2 binding site. Selective binding to the sigma-1 binding site is associated with various gastrointestinal effects, inhibition of contraction of the guinea pig ileum, and inhibition of acetylcholine-induced phosphoinositide response. In contrast, compounds which exhibit selective binding to the sigma-2 receptor are associated with dystonia and may block calcium channels. See Quiron et al., *Trends Pharm. Sci.* 13: 85–86 (1992); Rothman et al., *Mol. Pharmacol.* 39: 222–232 (1991). Thus, the compounds of the present invention which are selective for the sigma-1 receptor may be used for, in addition to the treament of psychosis, the treatment or prevention of gastrointestinal disorders such as emesis, colitis and the like, without any untoward dystonia. In addition, the compounds of the present invention which are selective for the sigma-2 receptor may be used for treating psychosis and conditions which are ameliorated by calcium channel blockers, e.g. hypertension, migrane and angina. Compounds which are selective for the sigma-2 receptor are known to produce dystonia. However, antagonists of the sigma-2 receptor are expected to be effective in treating hypertension, migrane and angina without dystonic side effects.

Preferably, compounds which are selective for the sigma-1 receptor compared to the sigma-2 receptor have an $IC_{50}$ ratio of sigma-1/sigma-2 of less than about 0.1 (see Table 10). Such compounds include, but are not limited to (±) N-(1-phenyl-2-propyl)-4-phenylbutylamine, R(–) N-(1-phenyl-2-propyl)-3-(2-naphthyl)propylamine, (±) N-[1-(1'-Naphthyl)-2-propyl]-3-phenylpropylamine, 4-Hydroxy-4-phenyl-1-(3-phenylpropyl)piperidine, N-(4-phenylbutyl)phenethylamine, Di-N-[3-(2'-naphthyl)propyl-N-methylamine, N-(4-phenylbutyl)benzylamine, N-(5-phenylpentyl)-(4-phenyl)butylamine, N-(5-phenylpentyl)benzylamine, N-(4-phenylbutyl)-N'-benzylpiperazine, N-4 (4-phenylbutyl)-N'-benzoylpiperazine, N-(3-phenylpropyl)-1-(p-ethoxyphenyl)-2-propylamine, N-(5-phenylpentyl)phenethylamine, N-(7-phenylheptyl)benzylamine, N-(7-phenylheptyl)phenethyl amine, N-(5-cyclohexylpentyl)benzylamine, N-(4-phenylbutyl)-1-phenyl-2-butylamine, N-(4-phenyl-3(E)-butenyl)-N'-methylpiperazine, N-(4-phenyl-3(Z)-butenyl)-N'-methylpiperazine, N-(4-(3-trifluoromethyl)-3-(Z)-butenyl)-N-methylpiperazine, N-(4-phenyl)-N'-methylpiperazine, N-(5-phenylpentyl)-3-phenylpropylamine, N-methyl-N-propyl-5-phenylpentylamine, N-Methyl-N-(3-phenylpropyl)-1-phenylisopropylamine, N-(5-phenylpentyl)piperidine, N,N-Dimethyl-5-phenylpentylamine, 5-cyclohexylpentylamine, N-methyl-5-cyclohexylpentylamine, N,N-Dimethyl-5-cyclohexylpentylamine, and N-Benzyl-N-methyl-5-phenylpentylamine.

Preferably, compounds which are selective for the sigma-2 receptor compared to the sigma-1 receptor have a ratio of sigma-1/sigma-2 of greater than about 10 (see Table 10). Such compounds include, but are not limited to N-phenyl-N'-(3-(1-phthalimido)propyl)-piperazine, and N-(4-phthalimido)butyl-N'-phenylpiperazine. N-(5-phthalimido)pentyl-N'-phenylpiperazine is also expected to be highly selective for sigma-2.

Surprisingly, the inventor has also discovered that the sigma receptor ligands of the present invention exhibit low affinity to the DA and PCP receptors. In addition, certain of the sigma receptor ligands of the present invention also exhibit low affinity for the 5-HT$_{1A}$ receptor. Thus, the sigma receptor ligands of the present invention may be used for the treatment of central nervous system disorders without the untoward side effects associated with unwanted binding at the DA, PCP and/or 5-HT$_{1A}$ receptors. By the term "low affinity" is intended a binding affinity of >100 nM, more preferably, >1000 nM in a DA, PCP or 5-HT$_{1A}$ binding assay. Especially preferred sigma receptor ligands have high binding to the sigma receptor and low binding to the DA, PCP and/or 5-HT$_{1A}$ receptors, as defined herein.

By the term "central nervous system disorder" is intended both psychiatric and movement dysfunctions. The selective sigma ligands of the present invention may be used to treat psychiatric disorders including psychoses, such as schizophrenia and related disorders, mania with psychotic features, major depression with psychotic features, organic psychotic disorders and other idiopathic psychotic disorders, in addition to anxiety disorders and depression. The term "schizophrenia" is intended to include any of a group of severe emotional disorders, usually of psychotic proportions, characterized by misinterpretation and retreat from reality, delusions, hallucinations, ambivalence, inappropriate affect, and withdrawn, bizarre, or regressive behavior. See Dorland's Illustrated Medical Dictionary, 26th edition, W. B. Saunders Company, Philadelphia, Pa., pp. 1171 (1981). The sigma receptor ligands of the present invention can also be used in treating movement disorders such as Parkinson's disease, tardive dyskinesia, and dystonias. See J. M. Walker et al., *Pharmacol. Rev.* 42: 355–402 (1990), the disclosure of which is fully incorporated by reference herein.

The sigma receptor ligands of the present invention are also useful for the treatment of drug abuse. In this aspect of the invention, the compounds of the invention are administered to an individual to ameliorate symptoms of drug withdrawal or to reduce craving for the drug, e.g. cocaine, heroin, PCP and hallucinogens.

As discussed above, the sigma receptor ligands of the present invention are highly selective for the sigma receptor and show low affinity for the DA and PCP receptors. Certain specific sigma receptor ligands of the present invention also bind with low affinity to 5-HT$_{1A}$ receptors. Thus, in addition to the treatment of central nervous system disorders, the sigma selective ligands of the present invention may also be used as a pharmacological tool in an animal model for the screening of potential sigma receptor agents.

The sigma receptor ligands of the present invention may also be radiolabelled with, for example, $^3$H, $^{11}$C, $^{14}$C, $^{18}$F, $^{125}$I and $^{131}$I. In their radiolabelled form, the sigma receptor ligands of the present invention may be used for audoradiography studies of the sigma receptor sites in tissue, especially neuronal tissue.

The sigma receptor ligands of the present invention may be prepared by general methods of synthesis as disclosed in Example 1. For example, a sigma receptor ligand having Formula (XXXX) may be prepared by reductive amination of a compound having Formula (XXXXI) with an aldehyde having Formula (XXXXII) according to Scheme I outlined below.

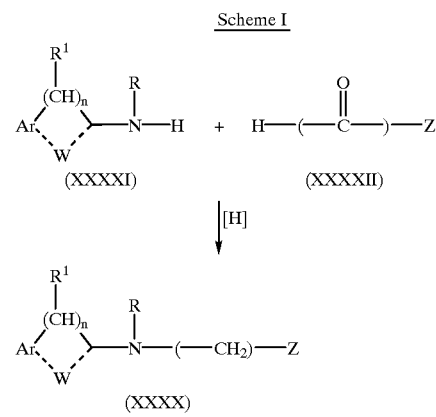

The starting compound having Formula (XXXXI), where W=—H H—, may be prepared by general methods of organic synthesis. For general methods of preparing compounds of Formula (XXXXI), reference is made to Fuller, R. W. et al., *J. Med. Chem.* 14: 322–325 (1971); Foye, W. O. et al., *J. Pharm. Sci* 68: 591–595 (1979); Bossier, J. R. et al., *Chem. Abstr.* 66: 46195h and 67: 21527a (1967); Aldous, F. A. B., *J. Med. Chem.* 17: 1100–1111 (1974); Fuller, R. W. et al., *J. Pharm. Pharmacol.* 25: 828–829 (1973); Fuller, R. W. et al., *Neuropharmacology* 14: 739–746 (1975); Conde, S. et al., *J. Med. Chem.* 21: 978–981 (1978); Lukovits, I. et al., *Int. J. Quantum Chem.* 20: 429–438 (1981); and Law, B., *J. Chromatog.* 407: 1–18 (1987), the disclosures of which are incorporated by reference herein in their entirety. The radio-labelled derivatives having Formula (XXXX) may be prepared by, for example, using a tritiated reducing agent to perform the reductive amination or by utilizing a $^{14}$C-labelled starting material.

Alternatively, where R is H, an N-substituted carboxamide of Formula (XXXXIII) may be reduced, for example, with LiAlH$_4$ to give the N,N-disubstituted sigma receptor ligand having the Formula (XXXX), below (see Scheme II).

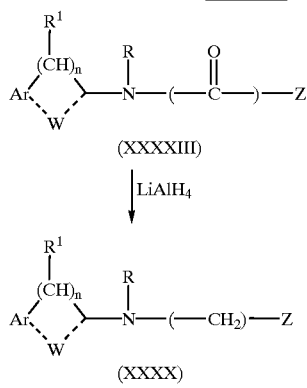

Alternatively, where the starting compound comprises a carbonyl group, the compound having the Formula (XXXXIV) may be reduced with, for example, AlH$_3$, diborane:methyl sulfide or other standard carbonyl reducing reagent to give the sigma receptor ligand having Formula (XXXX) according to Scheme III.

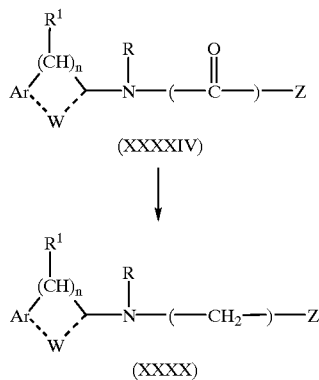

The sigma receptor ligands having Formula (XXXI) may be prepared by nucleophilic displacement of an electrophile (E) by the amino derivative (XXXXV) as outlined in Scheme IV. Examples of electrophiles which may be used for this purpose include halides such as Cl, Br, or I, tosylate or mesylate.

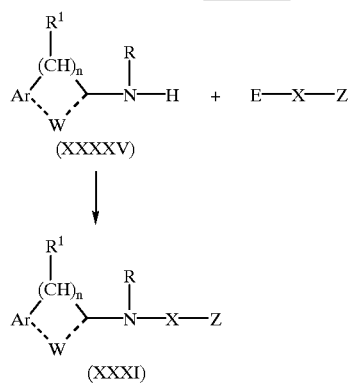

Morpholino derivatives having the Formula (XXXXVI) may be prepared by reduction of a compound of the Formula (XXXXVII) with, for example, sodium borohydride to give the ring-closed morpholino derivative (XXXXVI) according to Scheme V.

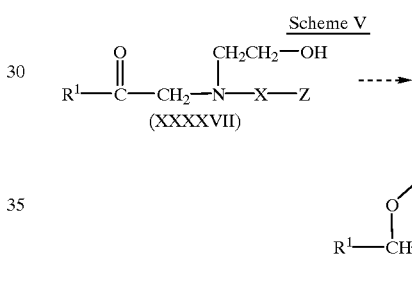

Alternatively, where the sigma receptor ligand comprises a tetrahydropyridine ring (Formula (XXXXVIII)), the tetrahydropyridine ring may be constructed by reaction of a 2-arylpropene derivative (Formula (XXXXIX)) with an alkyl amine (Formula (L)) and para-formaldehyde in the presence of orthophosphoric acid (Scheme VI).

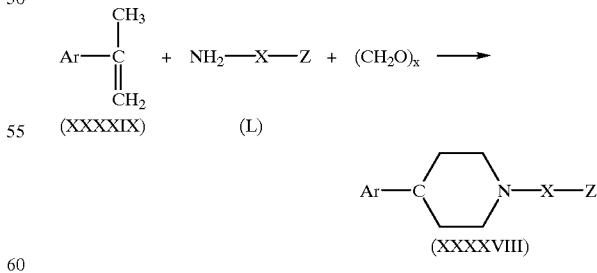

Reduction of the double bond of the compound having Formula (XXXXVIII) with, for example, hydrogen and a hydrogenation catalyst such as Pd/C or Pt gives the corresponding piperidine having Formula (LI):

Scheme VII

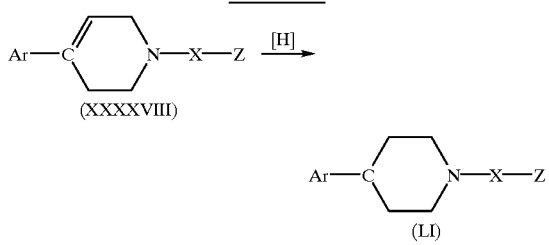

Also included within the scope of the present invention are the optical isomers of the compounds of the invention. The optical isomers may be separated by classical resolution techniques by, for example, formation of a salt of the amino group with an optically active acid. A particularly preferred acid for this purpose is (+)-di-p-toluoyl-D-tartaric acid. The resulting diastereoisomeric salt may then be separated by crystallization, chromatography, or by taking advantage of the differing solubilities of the two diastereoisomeric salts. The free base may then be isolated by treatment with a base such as aqueous ammonia and extraction with an organic solvent. Alternatively, the optical isomers may be prepared by resolution of the starting amine used to prepare the sigma ligand.

Also included within the scope of the present invention are the non-toxic pharmaceutically acceptable salts of the compounds of the invention. Acid addition salts are formed by mixing a solution of the sigma ligand of the invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

In the methods of treatment of the present invention, the pharmaceutical compositions may comprise the sigma receptor ligand at a unit dose level of about 0.01 to about 500 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

In addition to the sigma receptor ligands, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the sigma ligand with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the sigma ligands in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the sigma receptor ligands as well as the variety of conditions and parameters normally encountered in clinical therapy and which are obvious to those skilled in the art are within the spirit and scope of the invention.

EXAMPLES

Example 1

Preparation of Sigma Receptor Ligands

The sigma receptor ligands listed in Tables 1, 2 and 3 were synthesized according to one of twelve synthetic procedures (Methods A–L) disclosed immediately below.

Methods

Method A

R(−)-N-(3-Phenylpropyl)-1-phenyl-2-aminopropane Hydrochloride. A mixture of hydrocinnamaldehyde (1.11 g, 8.2 mmol) and R(−)-amphetamine (0.94 g, 7.0 mmol) in MeOH (20 mL) was hydrogenated over Pt/C 5% (0.2 g) at room temperature until the theoretical amount of hydrogen was absorbed. The methanolic solution of the base was separated from the catalyst by filtration and was treated with 10% HCl until the mixture was strongly acidic. The MeOH and $H_2O$ were removed under reduced pressure with warming to give a crude solid, which was recrystallized several times from MeOH and MEK to give 1.6 g (80%) of colorless crystals, mp 215–217° C.

Method B

R(−)-N-(Cyclopropylmethyl)-1-phenyl-2-aminopropane Maleate. To a suspension of $LiAlH_4$ (1.49 g, 38 mmoL) in anhyd. ether (50 mL) was added a solution of N-(α-methylphenylethyl)-2-cyclopropylcarboxamide (1.5 g, 74 mmol) in anhyd. $Et_2O$ (20 mL). The mixture was heated at reflux overnight, cooled to 0° C. and $H_2O$ (2.5 mL) was added in a drop wise manner. This was followed by the addition of 2N NaOH solution (2.5 mL) and then $H_2O$ (5 mL). After the inorganic precipitate was removed by filtration, the $Et_2O$ solution was dried (anhyd. $Na_2SO_4$) and treated with a solution of maleic acid (1.5 g in absolute EtOH (10 mL). The product was collected by filtration, washed with $Et_2O$ and recrystallized from 2-PrOH/$Et_2O$ (3×) to afford 1.3 g (59%) of fine crystals: mp 162–163° C.

Method C

N-(3-Phenylpropyl)-1-(4-bromophenyl)-2-aminopropane Hydrochloride. $AlH_3$ was prepared by the addition of $AlCl_3$ (0.07 g, 0.5 mmol) to a suspension of $LiAlH_4$ (0.064 g, 1.7 mmol) in $Et_2O$ (50 mL) at 0° C. under a nitrogen atmosphere. A solution of N-hydrocinnamoyl-1-(4-bromophenyl)-2-aminopropane (100 mg, 0.29 mmol) in dry $Et_2O$ (10 mL) was added in a drop wise manner, to the $AlH_3$ solution at 0° C. After the addition was complete, the mixture was allowed to stir for 0.5 h at the same temperature. Excess $AlH_3$ was decomposed by the addition of crushed ice (1 g) followed by 15% NaOH solution (2 mL). The mixture was filtered and the organic portion was separated, washed with $H_2O$ (20, 10, 5 mL), dried (anhyd. $MgSO_4$) and treated with sufficient HCl gas until precipitation was complete. The precipitate was collected by filtration and recrystallized from EtOH/$Et_2O$ (4×) to give 20 mg (19%) of a finely divided powder: mp 176–178° C.

Method D

N-(3-Phenylpropyl)-1-(3-trifluoromethylphenyl)-2-aminopropane Hydrochloride. A mixture of 1-(3-trifluoromethylphenyl)-2-propanone (102 mg, 0.50 mmol), 3-phenyl-1-propylamine (86 mg, 0.64 mmol), glacial acetic acid (8 mg, 0.13 mmol), and MeOH (2 mL) was allowed to stir at room temperature for 0.5 h. To this mixture was added over a 4-h period sodium borohydride (19 mg, 0.50 mmol) and the mixture was allowed to stir at room temperature for 20 h. The solvents were removed by warming under reduced pressure to give a small amount of an oil which was cooled and treated with 10% HCl. The crude product separated as a white solid, 122 mg (68%), mp 135–145° C. The crystals were dissolved in $H_2O$ and the solution was extracted with $Et_2O$. The $H_2O$ portion was separated, the $H_2O$ was evaporated, and the crystals reformed; recrystallization from acetone gave 66 mg (37%) of colorless crystals, mp 167–169° C.

Method E

R(−)-N-Benzyl-1-phenyl-2-aminopropane Hydrochloride. To a mixture of R(−)-amphetamine sulfate (0.633 g, 3.4 mmol), benzaldehyde (0.547 g, 5.2 mmol), MeOH (3 mL), and glacial acetic acid (0.5 g) was added sodium cyanoborohydride (0.263 g, 4.0 mmol) at room temperature over a 1-h period. During this addition, the pH was maintained at pH 5.5–6.0 by the addition of additional glacial acetic acid (0.25 g). After stirring 20 h at room temperature, the MeOH was removed by warming under reduced pressure. The residue was treated with an excess of 10% NaOH and the product extracted into $Et_2O$. The product was then extracted into an excess of 10% HCl solution; the aqueous layer was decanted and the water was removed by warming under reduced pressure to give the crude product, 0.5 g (56%), mp 170–174° C. After several recrystallizations from MeOH-MEK, the colorless crystals weighed 0.46 g (51%), mp 173–175° C.

Method F

R(−)-N-(2-Phenoxyethyl)-1-phenyl-2-aminopropane Hydrochloride. In a 5-mL reaction vial was placed R(−)-amphetamine (0.288 g, 2.1 mmol) and 2-phenoxyethyl chloride (0.335 g, 2.1 mmol). The vial was sealed and heated at 95° C. for 20 h. The reaction mixture was cooled, washed repeatedly with $Et_2O$ to give the crude product which melted at 155–160° C. Recrystallization (3×) using MeOH and MEK gave colorless crystals that weighed 50 mg (8%), mp 178–179° C.

Method G

R(−)-N-(3-Phenyl-3-oxopropyl)-1-phenyl-2-aminopropane Hydrochloride. A mixture of R(−)-amphetamine hydrochloride (0.259 g, 1.5 mmol), acetophenone (0.635 g, 5.3 mmol), paraformaldehyde (87 mg), MeOH (1.2 mL), and conc. HCl (1 drop) was placed in a 5-mL reaction vial, stirred, and heated at 65° C. for 24 h. After removing the solvent using reduced pressure and warming, the reaction mixture (which became partially solid) was dissolved in $H_2O$ (5 mL) and was extracted twice with hexane (10 mL). The aqueous portion was made basic with 10% NaOH and the product extracted into hexane (10 mL). The product was then extracted into a 10% HCl solution and the $H_2O$ and excess HCl were removed with warming under reduced pressure to form the crude solid, mp 135–144° C. Repeated recrystallizations using MEK and acetone gave 50 mg (11% yield) of colorless crystals, mp 146–147° C.

Method H (+)-α-[N-(3-phenylpropyl)amino]propiophenone Hydrochloride. A mixture of hydrocinnamaldehyde (2 g, 15 mmoL) and norephedrine (2.18 g, 14.4 mmol) in EtOH (100 mL) was hydrogenated over a catalytic amount of Pd/C 10%, at room temperature. A hydrogen uptake slightly in excess of theory was obtained. The suspension was filtered and the filtrate was treated with 2N HCl (30 mL). The acid solution was evaporated to give a residual solid, which was recrystallized twice from EtOH/Et$_2$O to give 2.34 g (55%) of needles: mp 211–213° C.

An ice-cooled mixture of CH$_2$Cl$_2$ (20 mL) and pyridine (0.8 g, 10 mmol) was treated with dry CrO$_3$ (0.5 g, 5 mmol), which was added in portions within a 30-min period. The purple-brown mixture was stirred at room temperature for 2 h. A solution of the amino alcohol prepared above (0.23 g, 1.24 mmol) in CH$_2$Cl$_2$ (5 mL) was added to the pyridine-CrO$_3$ mixture all at once with vigorous stirring. After 15 min, the yellow organic layer was decanted from the black, sticky precipitate and extracted with 5% NaOH (100 mL). The organic portion was filtered through a bed of anhyd. Na$_2$SO$_4$ and evaporated to dryness. The oily residue was treated with conc. HCl (5 mL), warmed, and the mixture was evaporated to dryness. The solid residue was recrystallized from 2-PrOH/Et$_2$O (2×) to give 150 mg (40%) of the hydrochloride salt: mp 154–155° C. (solidified and melted again at 170–172° C.).

Method I

N-Benzyl-2-phenylmorpholine Hydrochloride. To a solution of N-(2-hydroxyethyl)-N-(benzoylmethyl)-benzylamine hydrochloride (0.50 g, 1.6 mmol) and MeOH (5 mL) at 5° C. was added with stirring over 4 h sodium borohydride (0.213 g, 5.6 mmol). The reaction was allowed to warm to room temperature over 18 h; an additional amount of sodium borohydride (70 mg, 1.8 mmol) was added, and the reaction was stirred for an additional 24 h. A small amount of H$_2$O (1 ml) was added to the mixture and the solvents removed by warming under reduced pressure. Water (6 mL) and Et$_2$O (12 mL) were added to the reaction mixture; the ether layer was removed and the Et$_2$O evaporated under reduced pressure to give the crude liquid product as the free base (0.42 g). Treatment of the free base with cold conc. HCl (1 mL) followed by warming under reduced pressure to remove the H$_2$O and excess HCl afforded the crude product hydrochloride. Recrystallization from acetone gave colorless crystals of the amine hydrochloride 0.38 g (77%), mp 140–143° C.

A portion of these crystals (35 mg, 0.11 mmol) was heated at 125° C. with conc. HCl (0.17 g) in a sealed reaction vial for 1.25 h. The H$_2$O and excess HCl were removed by warming under reduced pressure to give 40 mg of the crude, tan product, mp 201–205° C. Two recrystallizations from acetone gave 21 mg (66%) of the substituted morpholine hydrochloride as colorless crystals, mp 211–212° C.

Method J 1-(4-Phenylbutyl)-4-(4-chlorophenyl)-1,2,5,6-tetrahydropyridine Maleate. To a stirred mixture of glacial acetic acid (1.9 g, 31.7 mmol) and acetic anhydride (0.4 g, 4 mmol) was added slowly (85%) orthophosphoric acid (0.43 g, 4 mmol). After the exothermic reaction had subsided, 4-phenylaminobutane (0.58 g, 4 mmol), paraformaldehyde (0.36 g) and 4-chloro-α-methylstyrene (0.62 g, 4 mmol) were added. The reaction mixture was stirred at 115° C. for 4 h then allowed to stand at room temperature for 2 days. The mixture was diluted with H$_2$O (10 mL), extracted with hexane and the aqueous layer made basic with Na$_2$CO$_3$. The crude product was extracted into hexane, dried over anhyd. K$_2$CO$_3$, and the solvent removed by evaporation. The crude free base was recrystallized from H$_2$O-MeOH to give the purified free base (mp 87–90° C.) which was dissolved in EtOH and treated with an Et$_2$O solution of maleic acid to give the maleate salt. Recrystallization from EtOH-Et$_2$O gave 0.6 g (35% yield) of fine crystals, mp 162–164° C.

Method K

N-(3-Phenylpropyl)-1-(4-hydroxyphenyl)-2-aminopropane Hydrobromide. A suspension of the free base of N-(3-phenylpropyl)-1-(4-methoxyphenyl)-2-aminopropane (200 mg, 0.63 mmol) in 48% HBr was heated at reflux for 6 h. The mixture was filtered while hot and the filtrate allowed to cool to room temperature to give crystals. The crystals were collected by filtration and recrystallized from EtOH-Et$_2$O to give 200 mg (88% yield) of the hydrobromide salt, mp 159–160° C.

Method L 1-(3-Chlorophenyl)-4-(3-phenylpropyl)piperazine Hydrochloride. To a stirred solution of diborane:dimethyl sulfide complex (2M) in THF (30 mL) was added drop wise a solution of dry THF (25 mL) and 1-(3-chlorophenyl)-4-(3-phenylpropionyl)piperazine (1.28 g, 3.86 mmol). The reaction mixture was stirred at room temperature for 18 h, quenched by the addition of MeOH-HCl (25 mL), and the solvents removed under reduced pressure. Additional MeOH was added and removed under reduced pressure to give a tan solid. This was dried for 18 h under vacuum then recrystallized from MEK to give 0.9 g (67%) of colorless crystals, mp 168–169° C.

TABLE 1

Properties of Some Series I Compounds.

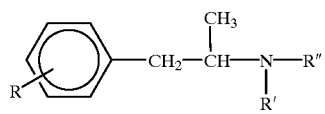

| Code No. | R | R' | R'' | Chiral | Method$^h$ | Salt | mp ° C. | Yield % | RS$^a$ | Formula | Anal$^b$ | Mol. Wt. |
|---|---|---|---|---|---|---|---|---|---|---|---|---|
| AD-51 | H | H | —(CH$_2$)Ph | R (−) | E | HCl | 173–175 | 51 | MK | C$_{16}$H$_{20}$ClN | c | 262 |
| AA-41 | H | H | —(CH$_2$)$_2$Ph | R (−) | A | HCl | 184–186 | 49 | MK | C$_{17}$H$_{22}$ClN | CHN | 276 |
| AA-67 | H | H | —(CH$_2$)$_2$Ph | S (+) | A | HCl | 184–186 | 22 | MK | C$_{17}$H$_{22}$ClN | CHN | 276 |
| AA-46 | H | H | —(CH$_2$)$_3$Ph | R (−) | A | HCl | 215–217 | 80 | MK | C$_{18}$H$_{24}$ClN | CHN | 290 |
| AD-74 | H | H | —(CH$_2$)$_2$—OPh | R (−) | F | HCl | 178–179 | 8 | MK | C$_{17}$H$_{22}$ClNO | CHN | 292 |

TABLE 1-continued

Properties of Some Series I Compounds.

$$\text{R} - \underset{}{\underset{}{\bigcirc}} - CH_2 - \underset{}{\overset{CH_3}{CH}} - \underset{\underset{R'}{|}}{\overset{}{N}} - R''$$

| Code No. | R | R' | R'' | Chiral | Method[h] | Salt | mp °C. | Yield % | RS[a] | Formula | Anal[b] | Mol. Wt. |
|---|---|---|---|---|---|---|---|---|---|---|---|---|
| AD-67 | H | H | —(CH$_2$)$_2$—COPh | R (−) | G | HCl | 146–147 | 11 | A | C$_{18}$H$_{22}$ClNO | CHN | 304 |
| AM-75 | H | H | —(CH$_2$)$_4$Ph | (±) | A | HCl | 158–159 | 30 | EO | C$_{19}$H$_{22}$ClNO | d | 304 |
| AM-134 | H | H | —(CH$_2$)$_3$—(NAPH-1)[e] | R (−) | B | HCl | 165–167 | 29 | I | C$_{22}$H$_{26}$ClN 0.3 H$_2$O | CHN | 345 |
| AM-140 | H | H | —(CH$_2$)$_3$—(NAPH-2)[f] | R (−) | B | Mal[g] | 188–190 | 45 | EO | C$_{26}$H$_{29}$ClN | CHN | 420 |
| AM-74 | H | H | —CH$_2$CH$\underset{CH_2}{\overset{CH_2}{<}}$CH$_2$ | (±) | B | Mal | 162–163 | 59 | 10 | C$_{17}$H$_{23}$NO$_4$ | CHN | 305 |
| AM-87 | H | H | —CH$_2$—C≡C-Ph | R (−) | F | HCl | 223–224 | 14 | C | C$_{17}$H$_{20}$ClN | CHN | 286 |
| AM-159 | 4-HO | H | —(CH$_2$)$_3$-Ph | (±) | K | HBr | 159–160 | 88 | EO | C$_{18}$H$_{24}$BrNO | CHN | 326 |
| AM-156 | 4-CH$_3$O | H | —(CH$_2$)$_3$-Ph | (±) | A | HCl | 192–194 | 67 | EO | C$_{19}$H$_{26}$ClNO | CHN | 320 |
| AM-79 | 3-Br | H | —(CH$_2$)$_3$-Ph | (±) | C | HCl | 184–185 | 35 | 10 | C$_{18}$H$_{23}$BrClN | CHN | 369 |
| AM-72 | 4-Br | H | —(CH$_2$)$_3$-Ph | (±) | C | HCl | 176–178 | 19 | EO | C$_{18}$H$_{23}$BrClN | CHN | 369 |
| JM-152 | 3,4-Cl$_2$ | H | —(CH$_2$)$_3$-Ph | (±) | C | HCl | 159–161 | 8 | N | C$_{18}$H$_{22}$Cl$_3$N | CHN | 359 |
| AM-108 | 4-I | H | —(CH$_2$)$_3$-Ph | R (−) | E | HCl | 154–155 | 28 | EO | C$_{18}$H$_{23}$ClIN | CHN | 416 |
| AA-111 | 3-CF$_3$ | H | —(CH$_2$)$_3$-Ph | (±) | D | HCl | 167–169 | 37 | N | C$_{19}$H$_{23}$ClF$_3$N | CHN | 358 |
| AA-55 | H | CH$_3$ | —(CH$_2$)$_2$-Ph | S (+) | A | HCl | 184–186 | 56 | MK | C$_{18}$H$_{24}$ClN | CHN | 290 |

[a]RS = Recrystallization solvent: ethyl acetate (A), acetonitrile (C), absolute ethanol (E), 2-propanol (I), 2-butanone (K), methanol (M), acetone (N), diethyl ether (O).
[b]ANAL = Microanalysis. All new compounds were submitted for elemental analysis and found values are within 0.4% of theory.
[c]Benzoate Salt (mp 101–103° C.) previously reported: J. Pharm. Sci. 64:1462 (1975). Compound AD-51 was converted to the benzoate salt for purpose of identification: mp 100–101° C.
[d]Literature (J. Pharm. Sci. 64:1462 (1975)) mp 133° C. for p-toluenesulfonate salt. A small sample of AM-75 was converted to this salt for purpose of comparison: mp 132–133° C.
[e]NAPH-1 = 1-Naphthyl.
[f]NAPH-2 = 2-Naphthyl.
[g]Mal = maleate salt.
[h]There are other ways in which the Series I compounds might have been prepared than the method shown.

TABLE 2

Properties of Additional Series I Compounds.

$$\underset{}{\bigcirc} - (CH_2)_{\overline{n}} - \underset{\underset{R}{|}}{\overset{R'}{N}} - R$$

| Code No. | R | R' | n | Chiral | Method[d] | Salt | mp °C. | Yield % | RS[a] | Formula | Anal[b] | Mol. Wt. |
|---|---|---|---|---|---|---|---|---|---|---|---|---|
| AM-80 | (2-aminoindane group) | H | 3 | (±) | H | HCl | 154–155 | 40 | IO | C$_{18}$H$_{22}$ClNO | CHN | 304 |
| AM-133 | (1-naphthylmethyl-CH(CH$_3$)-NH-) | H | 3 | (±) | A | HCl | 246–247 | 62 | EO | C$_{18}$H$_{22}$ClN | CHN | 288 |

TABLE 2-continued

Properties of Additional Series I Compounds.

$$\text{Ph—(CH}_2)_n\text{—N(R')—R}$$

| Code No. | R | R' | n | Chiral | Method[d] | Salt | mp °C. | Yield % | RS[a] | Formula | Anal[b] | Mol. Wt. |
|---|---|---|---|---|---|---|---|---|---|---|---|---|
| AM-113 | (2-amino-2,3,4,5-tetrahydro-1H-benzocycloheptene) | H | 3 | | A | HCl | 202–203 | 50 | E | $C_{18}H_{24}ClN$ | c | 290 |
| AM-114 | (α-methyl-β-oxo-phenethylamine) | H | 3 | (±) | A | HCl | 212–213 | 50 | EO | $C_{22}H_{26}ClN$ | CHN | 340 |
| AM-120 | Ph(CH$_2$)$_3$— | H | 3 | (±) | A | HCl | 188–189 | 50 | EO | $C_{22}H_{26}ClN$ | CHN | 340 |
| MY-10 | (1-(2-naphthyl)propan-2-amine) | H | 3 | (±) | B | HCl | 250–251 | 81 | I | $C_{20}H_{25}ClN$ | CHN | 315 |

[a]See footnote a, Table 1.
[b]See footnote b, Table 1.
[c]Literature (Chem. Abstr. 49:7812 (1955)), mp 201–202° C.
[d]There are other ways in which the Series I compounds might have been prepared than the method shown.

TABLE 3

Properties of Series II Compounds.

⟨phenyl⟩—(CH$_2$)$_n$—R

| Code No. | R | n | Chiral | Method[e] | Salt | mp °C. | Yield % | RS[a] | Formula | Anal[b] | Mol. Wt. |
|---|---|---|---|---|---|---|---|---|---|---|---|
| JLH-166 | 3-CF$_3$-phenyl-piperazinyl | 2 | | L | HCl | 195–200 (DEC) | 50 | K | C$_{19}$H$_{22}$ClF$_3$N$_2$·1/2 H$_2$O | c | 380 |
| JLH-170 | 3-Cl-phenyl-piperazinyl | 2 | | L | HCl | 197–199 | 40 | K | C$_{18}$H$_{22}$Cl$_2$N$_2$·H$_2$O | CHN | 355 |
| JLH-171 | 3-Cl-phenyl-piperazinyl | 3 | | L | HCl | 168–169 | 67 | K | C$_{19}$H$_{24}$Cl$_2$N$_2$·H$_2$O | CHN | 369 |
| AM-128 | phenyl-piperazinyl | 3 | | A | HCl | 217–218 | 70 | EO | C$_{20}$H$_{26}$ClN | d | 316 |
| AM-127 | 4-hydroxy-4-phenyl-piperidinyl | 3 | (±) | A | HCl | 207–209 | 90 | EO | C$_{20}$H$_{26}$ClNO | CHN | 332 |
| AM-129 | 4-(4-chlorophenyl)-1,2,3,6-tetrahydropyridinyl | 4 | | J | Mal | 162–164 | 35 | EO | C$_{25}$H$_{28}$ClNO$_4$ | CHN | 442 |
| AD-34 | 4-methyl-2-phenyl-morpholinyl | 1 | (±) | I | HCl | 211–212 | 49 | N | C$_{17}$H$_{20}$ClNO | CHN | 290 |

[a]See footnote a, Table 1.
[b]See footnote b, Table 1.
[c]Literature (Chem. Abstr. 60:12028), mp 205–207° C.
[d]Literature (J. Med. Chem. 9:555 (1966)), mp 214–216° C.
[e]There are other ways in which the Series II compounds might have been prepared than the method shown.

Example 2

Sigma, PCP and Dopamine Receptor Binding Assays

Methods

Sigma receptor binding assays using guinea pig brain membrane homogenates and the radioligand [$^3$H]DTG were conducted as described by Weber et al.. *P.N.A.S.* (*USA*) 83: 8784–8788 (1986) which indicates binding to both the sigma-1 and sigma-2 sites. Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000× g for 20 minutes at 4° C. The supernatant was centrifuged at 20,000× g for 20 minutes at 4° C. The resulting pellet was resuspended in 10 initial volumes of 50 mM Tris/HCl buffer at pH 7.4 and centrifuged at 20,000× g for 20 minutes at 4°

C. The resulting pellet was resuspended in 5 initial volumes ice-cold 50 mM Tris/Hcl (pH 0.4), and the final volume was adjusted to yield a protein concentration of 3 mg/ml. Aliquots of 20-ml were stored at −70° C. until used, with no detectable loss of binding.

For [$^3$H]DTG binding assays, the frozen membrane suspensions were thawed and diluted 1:3 in 50 mM Tris/HCl (pH 7.4). To 12×75 mm polystyrene test tubes were added 0.8 ml of diluted membrane suspension, 0.1 ml of [$^3$H]DTG (Dupont/NEN) to yield a final concentration of 1.4 nM, and 0.1 ml of unlabelled drugs or buffer. The protein concentration in the 1-ml final incubation volume was 800 ug/ml, corresponding to 32 mg of brain tissue (original wet weight) and to a tissue concentration within the linear range for specific binding. Non-specific binding was defined as that remaining in the presence of 10 uM haloperidol. Incubations were terminated after 90 minutes at room temperature by addition of 4 ml of ice-cold 50 mM Tris/HCl (pH 7.4) and rapid filtration of the membrane suspension through Whatman GF/B glass-fiber filters under vacuum, using a 48-well cell harvester (Brandel). The filters were washed 2 times with 4 ml of 50 mM Tris/HCl (pH 7.4). Each filter was suspended in 10 ml Cytoscint (ICI), and radioactivity was measured by liquid scintillation spectrometry at a counting efficiency of approximately 50%. $IC_{50}$ values were determined by non-linear regression analyis.

PCP receptor binding assays against $^3$H-MK-801 were conducted as described by Keana et al., *Proc. Natl. Acad. Sci (USA)* 86: 5631–5635 (1989); Keana et al., *Life Sciences* 43: 965–973 (1988). For (+) $^3$H-MK-801 binding, 1 nM of radioligand was incubated with about 100 ug of thawed rat brain membrane protein for 4 hr at room temperature. The assays were carried out in 5 mM Tris/acetate and were stopped by rapid filtration through Whatman GF/B or Schleicher & Schuell no. 32 glass fiber filters (presoaked in 0.05% polyethylenamine).

Dopamine D1 and D2 receptor binding assays were performed as described by Billard et al., *Life Sci.* 35: 1885–1893 (1984) using [$^3$H]SCH-23390 for the D1 receptors and [$^3$H]domperidone for the D2 receptors (Baudry et al., *Arch. Pharmacol.* 308: 231–237 (1979).

Rat striatal membranes were prepared from frozen tissue by Poltron homogenization in 25 volumes of ice cold Tris-EDTA buffer (50 mM Tris-HCl, 1 mM EDTA, pH 7.4 at 4° C.). The homogenate was centrifuged at 48,000× g for 10 min. at 4° C., and the pellet was resuspended in 25 volumes of the same buffer. This suspension was then incubated at 37° C. for 15 min., followed by recentrifugation as before. The resulting pellet was resuspended in 267 volumes of assay buffer (50 mM Tris-HCl, 120 mM NaCl, 5 mM KCl, 2 mM $CaCl_2$, 1 mM $MgCl_2$, pH 7.4 at 37° C.).

The binding assays were conducted with 100 uL of [$^3$H]SCH-23390 or [$^3$H]domperidone (to give about 1 nM final), 100 uL of buffer or drug solution, and 800 uL of membrane suspension (to give about 250 ug of striatal membrane protein per assay). The tubes were incubated at 37° C. for 60 min. The assays were stopped by rapid filtration over Schleicher & Schuell #32 or Whatman GF/B glass fiber filters (presoaked in 0.5% polyethyleneimine for [$^3$H]domperidone binding), followed by two 3 mL washes of ice cold buffer using a Brandel cell harvester. After vigorous shaking, the filter disks were counted at 52% efficiency in 5 mL of Cytoscint (ICN).

The results of these binding assays appear in Table 4.

TABLE 4

| # | COMPOUND | ISOMER | SIGMA IC50 (M) | SIGMA S.E.M. | n | D1 IC50 ($\mu$M) (n) | D2 IC50 ($\mu$M) (n) | PCP IC50 (M) |
|---|---|---|---|---|---|---|---|---|
| 1 | (structure: HN-CH(CH$_3$)-CH$_2$-Ph with propyl-phenyl chain) | R− | $2.87 \times 10^{-8}$ | $3.80 \times 10^{-9}$ | 5 | >10 (2) | 4.65 ± .43 (3) | $>10^{-5}$ |
| 2 | (structure: HN-CH(CH$_3$)-CH$_2$-(3,4-dichlorophenyl) with propyl-phenyl chain) | +/− | $1.25 \times 10^{-8}$ | $1.00 \times 10^{-10}$ | 4 | >10 (2) | 1.79 ± .02 (2) | $>10^{-5}$ |

TABLE 4-continued

| # | COMPOUND | ISO-MER | SIGMA IC50 (M) | SIGMA S.E.M. | n | D1 D2 IC50 (μM) (n) | PCP IC50 (M) |
|---|----------|---------|----------------|--------------|---|---------------------|--------------|
| 3 | (R)-N-methyl amphetamine | R– | $8.65 \times 10^{-6}$ | $1.25 \times 10^{-6}$ | 2 | | $>10^{-5}$ |
| 4 | (R)-N-ethyl amphetamine | R– | $6.85 \times 10^{-7}$ | $2.50 \times 10^{-8}$ | 2 | | $>10^{-5}$ |
| 5 | (R)-N-propyl amphetamine | R– | $1.705 \times 10^{-6}$ | $1.65 \times 10^{-8}$ | 2 | | $>10^{-5}$ |
| 6 | (R)-N-benzyl amphetamine | R– | $1.22 \times 10^{-7}$ | $1.65 \times 10^{-8}$ | 2 | | $>10^{-5}$ |
| 7 | (R)-N-phenethyl amphetamine | R– | $6.24 \times 10^{-8}$ | $9.00 \times 10^{-9}$ | 2 | | $9.00 \times 10^{-6}$ |
| 8 | (R)-N-(2-phenoxyethyl) amphetamine | R– | $4.71 \times 10^{-8}$ | $5.75 \times 10^{-9}$ | 2 | | $>10^{-5}$ |

TABLE 4-continued

| # | COMPOUND | ISO-MER | SIGMA IC50 (M) | SIGMA S.E.M. | n | D1 D2 IC50 (μM) (n) | PCP IC50 (M) |
|---|---|---|---|---|---|---|---|
| 9 | | R− | $5.84 \times 10^{-8}$ | $7.45 \times 10^{-9}$ | 2 | | $>10^{-5}$ |
| 10 | | +/− | $9.69 \times 10^{-9}$ | $5.10 \times 10^{-10}$ | 2 | | $>10^{-5}$ |
| 11 | | R− | $9.15 \times 10^{-9}$ | $2.75 \times 10^{-9}$ | 2 | | $>10^{-5}$ |
| 12 | | R− | $2.35 \times 10^{-9}$ | $6.53 \times 10^{-10}$ | 4 | | $>10^{-5}$ |
| 13 | | +/− | $1.22 \times 10^{-7}$ | $2.50 \times 10^{-9}$ | 2 | | $>10^{-5}$ |

TABLE 4-continued

| # | COMPOUND | ISO-MER | SIGMA IC50 (M) | SIGMA S.E.M. | n | D1 IC50 ($\mu$M) (n) | D2 IC50 ($\mu$M) (n) | PCP IC50 (M) |
|---|---|---|---|---|---|---|---|---|
| 14 | | +/- | $2.85 \times 10^{-8}$ | $5.20 \times 10^{-9}$ | 2 | | | $>10^{-5}$ |
| 15 | | | $1.445 \times 10^{-8}$ | $1.21 \times 10^{-9}$ | 4 | >10 (2) | 1.68 ± 3.6 (2) | $>10^{-5}$ |
| 16 | | +/- | $1.83 \times 10^{-8}$ | $2.65 \times 10^{-9}$ | 2 | | | $>10^{-5}$ |
| 17 | | +/- | $6.60 \times 10^{-9}$ | $1.79 \times 10^{-9}$ | 2 | | | $>10^{-5}$ |
| 18 | | +/- | $1.08 \times 10^{-8}$ | 0.00 | 2 | | | $>10^{-5}$ |

TABLE 4-continued

| # | COMPOUND | ISO-MER | SIGMA IC50 (M) | SIGMA S.E.M. | n | D1 IC50 ($\mu$M) (n) | D2 IC50 ($\mu$M) (n) | PCP IC50 (M) |
|---|---|---|---|---|---|---|---|---|
| 19 | [structure: HN-CH(CH3)-CH2-(4-OCH3-C6H4), N-CH2CH2CH2-C6H5] | +/- | $1.493 \times 10^{-8}$ | $2.95 \times 10^{-9}$ | 4 | >10 (2) | 9.32 ± 4.5 (3) | $>10^{-5}$ |
| 20 | [structure: HN-CH(CH3)-CH2-(3-Br-C6H4), N-CH2CH2CH2-C6H5] | +/- | $5.17 \times 10^{-9}$ | $1.02 \times 10^{-9}$ | n = 3. | | | $>10^{-5}$ |
| 21 | [structure: HN-CH(CH3)-CH2-(4-Br-C6H4), N-CH2CH2CH2-C6H5] | +/- | $9.11 \times 10^{-9}$ | $6.15 \times 10^{-10}$ | 2 | | | $>10^{-5}$ |
| 22 | [structure: HN-CH(CH3)-CH2-(4-I-C6H4), N-CH2CH2CH2-C6H5] | R- | $1.597 \times 10^{-8}$ | $4.64 \times 10^{-9}$ | 4 | >10 (2) | 3.81 ± 9.7 (3) | $>10^{-5}$ |
| 23 | [structure: HN-CH(CH3)-CH2-(3-CF3-C6H4), N-CH2CH2CH2-C6H5] | +/- | $4.10 \times 10^{-9}$ | $2.05 \times 10^{-10}$ | 2 | | | $>10^{-5}$ |

TABLE 4-continued

| # | COMPOUND | ISO-MER | SIGMA IC50 (M) | SIGMA S.E.M. | n | D1 D2 IC50 ($\mu$M) (n) | PCP IC50 (M) |
|---|----------|---------|----------------|--------------|---|--------------------------|--------------|
| 24 | *structure* | +/− | $6.91 \times 10^{-7}$ | $1.39 \times 10^{-7}$ | 2 | | $>10^{-5}$ |
| 25 | *structure* | R− | $1.01 \times 10^{-7}$ | $4.43 \times 10^{-8}$ | 2 | | $>10^{-5}$ |
| 26 | *structure* | S,S− | $2.88 \times 10^{-7}$ | $2.00 \times 10^{-9}$ | 2 | | $>10^{-5}$ |
| 27 | *structure* | S+ | $3.26 \times 10^{-8}$ | $2.05 \times 10^{-9}$ | 2 | | $>10^{-5}$ |
| 28 | *structure* | R− | $4.80 \times 10^{-5}$ | 0.00 | 2 | | $>10^{-5}$ |

TABLE 4-continued
| # | COMPOUND | ISO-MER | SIGMA IC50 (M) | SIGMA S.E.M. | n | D1 D2 IC50 (µM) (n) | PCP IC50 (M) |
|---|----------|---------|----------------|--------------|---|---------------------|--------------|
| 29 | 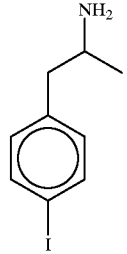 | R− | $4.95 \times 10^{-6}$ | $5.00 \times 10^{-8}$ | 2 | | $>10^{-5}$ |
| 30 | 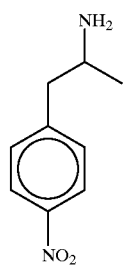 | R− | $2.10 \times 10^{-5}$ | $2.00 \times 10^{-6}$ | 2 | | $>10^{-5}$ |
| 31 | 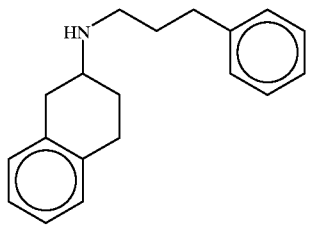 | +/− | $2.08 \times 10^{-8}$ | $6.50 \times 10^{-10}$ | 2 | | $>10^{-5}$ |
| 32 | 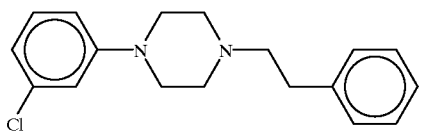 | | $1.09 \times 10^{-8}$ | $2.67 \times 10^{-9}$ | 2 | | $>10^{-5}$ |
| 33 | 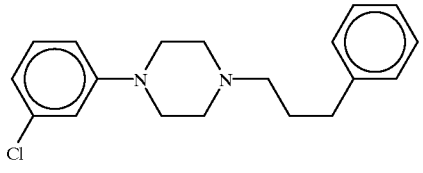 | | $1.95 \times 10^{-8}$ | $5.60 \times 10^{-9}$ | 2 | | $>10^{-5}$ |
| 34 | 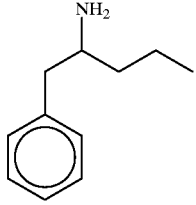 | +/− | $2.56 \times 10^{-6}$ | $4.00 \times 10^{-8}$ | 2 | | $>10^{-5}$ |

TABLE 4-continued

| # | COMPOUND | ISO-MER | SIGMA IC50 (M) | SIGMA S.E.M. | n | D1 IC50 ($\mu$M) (n) | D2 | PCP IC50 (M) |
|---|---|---|---|---|---|---|---|---|
| 35 | (morpholine with N-benzyl and 2-phenyl substituents) | +/− | $2.59 \times 10^{-7}$ | $1.90 \times 10^{-8}$ | 2 | | | $>10^{-5}$ |
| 36 | (CH₃-N(phenethyl)(1-methyl-2-phenylethyl)) | S+ | $6.85 \times 10^{-9}$ | $1.50 \times 10^{-10}$ | 2 | | | $5.00 \times 10^{-6}$ |
| 37 | (3-CF₃-phenyl piperazine N-phenethyl) | | $7.75 \times 10^{-9}$ | $1.45 \times 10^{-9}$ | 2 | | | $>10^{-5}$ |
| 38 | (4-chlorophenyl-tetrahydropyridine N-(3-phenylpropyl)) | | $4.30 \times 10^{-9}$ | $2.10 \times 10^{-9}$ | 2 | | | $>10^{-5}$ |
| 39 | (4-phenylpiperidine N-phenethyl) | | $1.20 \times 10^{-9}$ | $2.00 \times 10^{-10}$ | 2 | | | $>10^{-5}$ |
| 40 | (4-hydroxy-4-phenylpiperidine N-phenethyl) | | $3.06 \times 10^{-9}$<br>$3.18 \times 10^{-9}$ | $3.4 \times 10^{-10}$<br>$3.0 \times 10^{-11}$ | 5<br>$2^1$ | >10 (2) | $1.25 \pm .06$ (3) | $>10^{-5}$ |
| 41 | (naphthalen-2-yl-propyl-NH-phenethyl) | | $4.58 \times 10^{-9}$<br>$5.59 \times 10^{-9}$ | $8.7 \times 10^{-10}$<br>$2.06 \times 10^{-9}$ | 5<br>$2^1$ | >10 (2) | $1.92 \pm .19$ (3) | $>10^{-5}$ |

TABLE 4-continued

| # | COMPOUND | ISO-MER | SIGMA IC50 (M) | SIGMA S.E.M. | n | D1 IC50 ($\mu$M) (n) | D2 | PCP IC50 (M) |
|---|---|---|---|---|---|---|---|---|
| 42 | | S(+) | $5.20 \times 10^{-9}$ | $2.00 \times 10^{-10}$ | 2 | | | $>10^{-5}$ |
| 43 | | S(+) | $2.27 \times 10^{-8}$ | $2.10 \times 10^{-9}$ | 2 | | | $>10^{-5}$ |
| 44 | | S(+) | $6.90 \times 10^{-9}$ | $4.10 \times 10^{-9}$ | 2 | | | $>10^{-5}$ |
| 45 | | S(+) | $5.95 \times 10^{-9}$ | $3.95 \times 10^{-9}$ | 2 | | | $>10^{-5}$ |
| 46 | | | $6.95 \times 10^{-9}$ | $7.50 \times 10^{-10}$ | 2 | | | $>10^{-5}$ |
| 47 | | | $5.65 \times 10^{-9}$ | $1.02 \times 10^{-9}$ | 2 | | | $>10^{-5}$ |
| 48 | | | $2.70 \times 10^{-9}$ | $2.00 \times 10^{-10}$ | 2 | | | $>10^{-5}$ |

TABLE 4-continued

| # | COMPOUND | ISO-MER | SIGMA IC50 (M) | SIGMA S.E.M. | n | D1 IC50 ($\mu$M) (n) | D2 IC50 ($\mu$M) (n) | PCP IC50 (M) |
|---|---|---|---|---|---|---|---|---|
| 49 | [structure] | | $1.038 \times 10^{-8}$ | $2.61 \times 10^{-9}$ | 4 | >10 (2) | 5.77 ± .83 (3) | >$10^{-5}$ |
| 50 | [structure] | | $2.95 \times 10^{-9}$ | $5 \times 10^{-11}$ | 2 | | | >$10^{-5}$ |
| 51 | [structure] | | $4.23 \times 10^{-9}$ | $1.42 \times 10^{-9}$ | 4 | 2.99 ± .04 (3) | .158 ± .028 (2) | >$10^{-5}$ |

Results

As can be seen in Table 4, the sigma receptor ligands of the present invention exhibit very high binding with respect to the sigma receptors and very low binding with respect to the PCP and DA receptors. Therefore, these sigma receptor ligands can be used for the treatment of mental illness without the extrapyramidal side effects of traditional neuroleptic agents caused by binding to the DA receptor.

Example 3

5-HT$_{1A}$ Binding Assays

The sigma receptor ligands listed above (nos. 1–51) were further tested for binding at the 5-HT$_{1A}$ receptor using the method of Peroutka, S. J., *J. Neurochem.* 47: 529–540 (1986). The results appear in Table 5.

TABLE 5

| | 5-HT$_{1A}$ | | |
|---|---|---|---|
| Compound No. | IC$_{50}$ (nM) | ±SEM (n) | Ratio 5-HT$_{1A}$/$\sigma$ |
| 1 | 115.00 | 12.00 (2) | 4 |
| 2 | 90.30 | 28.83 (3) | 12 |
| 3 | 1776.33 | 579.30 (3) | .20 |
| 4 | 4052.50 | 372.50 (2) | 5.9 |
| 5 | 1500.00 | 100.00 (2) | .88 |
| 6 | 3781.50 | 3458.50 (2) | 31 |
| 7 | 2475.00 | 95.00 (2) | 40 |
| 8 | 43.65 | 1.85 (2) | .92 |
| 9 | 122.00 | 6.00 (2) | 2 |
| 10 | 212.00 | 31.00 (2) | 22 |
| 11 | 104.30 | 16.70 (2) | 11 |
| 12 | 131.58 | 39.31 (4) | 56 |
| 13 | 288.00 | 62.00 (2) | 2 |
| 14 | 154.50 | 35.50 (2) | 5.4 |
| 15 | 30.70 | 3.43 (3) | 2 |
| 16 | 44.8 | 2.5 (2) | 2.4 |
| 17 | 87.80 | 12.20 (2) | 13 |
| 18 | 588.50 | 68.50 (2) | 54 |
| 19 | 114.23 | 12.43 (3) | 7.6 |
| 20 | 108.05 | 10.95 (2) | 17 |
| 21 | 195.50 | 14.50 (2) | 21 |
| 22 | 202.00 | 47.00 (2) | 13 |
| 23 | 105.75 | 13.25 (2) | 25 |
| 24 | 955.50 | 33.50 (2) | 1.4 |
| 25 | 753.00 | 135.00 (2) | 7.3 |
| 26 | 10000 | (1) | 3.5 |
| 27 | 6514.00 | 874.00 (2) | 200 |
| 28 | 2442.50 | 342.50 (2) | .05 |
| 29 | 15515.00 | 5515.00 (2) | 3.1 |
| 30 | 54999.50 | 44999.50 (2) | 2.6 |
| 31 | 19.30 | 4.20 (2) | .92 |
| 32 | 8.73 | 0.46 (2) | .80 |
| 33 | 51.60 | 2.30 (2) | 2.6 |
| 34 | 6650.00 | 710.00 (2) | 2.6 |
| 35 | 10360.00 | 360.00 (2) | 40 |
| 36 | 1626.67 | 378.17 (3) | 239 |
| 37 | 20.30 | 4.70 (2) | 2.6 |
| 38 | 107.15 | 27.25 (2) | 25 |
| 39 | 89.60 | 0.10 (2) | 75 |
| 40 | 2965.00 | 585.00 (2) | 970 |
| 41 | 34.67 | 9.09 (3) | 7.6 |
| 42 | 572.50 | 134.50 (2) | 110 |
| 43 | 1112.33 | 162.85 *3) | 50 |
| 44 | 277.67 | 33.52 (3) | 40 |

TABLE 5-continued

| | 5-HT$_{1A}$ | | |
|---|---|---|---|
| Compound No. | IC$_{50}$ (nM) | ±SEM (n) | Ratio 5-HT$_{1A}$/σ |
| 45 | 594.00 | 67.68 (3) | 100 |
| 46 | 21.47 | 3.60 (3) | 3 |
| 47 | 9.23 | 1.58 (2) | 1.6 |
| 48 | 6.30 | 0.74 (2) | 2.3 |
| 49 | 312.67 | 27.38 (3) | 30 |
| 50 | 281.67 | 69.00 (3) | 94 |

Example 4

Further [$^3$H]DTG and 5HT-1A Binding Assays

Further sigma receptor binding assays against [$^3$H]DTG and 5HT-1A binding assays were conducted according to the procedure outlined in the previous examples. The results of these further studies are listed in Table 6.

TABLE 6

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 52 | 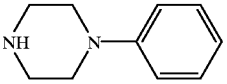 | 11891.00 | 399.00 | (2) | — | | |
| 53 | 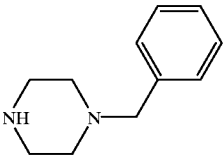 | 10901.50 | 1198.50 | (2) | — | | |
| 54 | 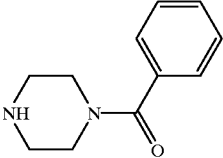 | 11815.00 | 1815.00 | (2) | — | | |
| 55 | 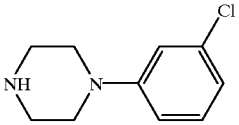 | 6393.67 | 4426.77 | (3) | — | | |
| 56 | 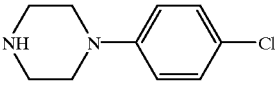 | 1190.50 | 159.50 | (2) | — | | |
| 57 | 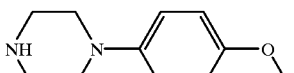 | 6069.00 | 251.00 | (2) | — | | |
| 58 | 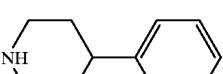 | 2054.50 | 14.50 | (2) | — | | |

TABLE 6-continued
| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 59 | 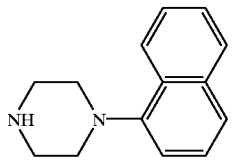 | 2830.00 | 470.00 | (2) | — | | |
| 60 | 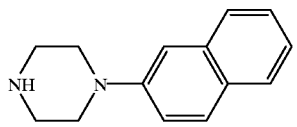 | 575.50 | 98.50 | (2) | — | | |
| 61 | 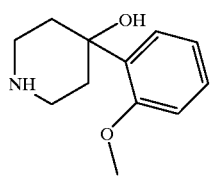 | 14850.00 | 4850.00 | (2) | — | | |
| 62 | 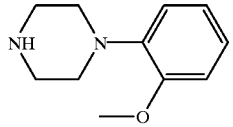 | 11625.00 | 1625.00 | (2) | — | | |
| 63 | 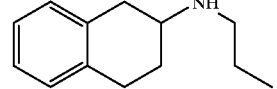 | 763.33 | 352.86 | (3) | — | | |
| 64 | 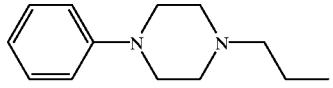 | 77.40 | 4.29 | (3) | 784.00 | 17.00 | (2) |
| 65 | 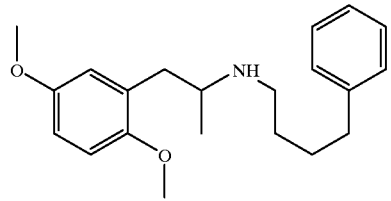 | 72.87 | 3.46 | (3) | 182.00 | 30.00 | (2) |
| 66 | 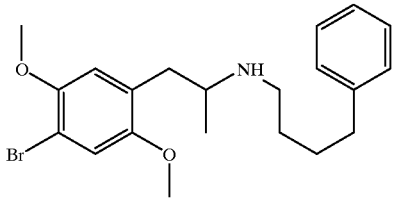 | 45.10 | 6.85 | (3) | 272.00 | 44.00 | (2) |
| 67 | 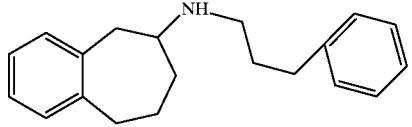 | 59.60 | 1.12 | (3) | 19.35 | 4.95 | (2) |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 68 | | 3.25 | 0.85 | (4) | 1320.00 | 158.46 | (3) |
| 69 | | 2.25 | 1.00 | (4) | 891.00 | 181.56 | (3) |
| 70 | | 116.20 | 62.80 | (2) | 3885.75 | 1466.82 | (4) |
| 71 | | 5.68 | 2.19 | (2) | 225.33 | 57.50 | (3) |
| 72 | | 7.23 | 1.92 | (2) | 11.30 | 3.25 | (3) |
| 73 | | 6.98 | 2.16 | (2) | 55.70 | 0.50 | (2) |
| 74 | | 81.87 | 21.83 | (3) | — | | |

TABLE 6-continued

| # | COMPOUND | SIGMA IC$_{50}$ (nM) MEAN | SEM | (n) | 5HT-1A (nM) MEAN | SEM | (n) |
|---|---|---|---|---|---|---|---|
| 75 | | 13.57 | 1.67 | (3) | 255.00 | | (1) |
| 76 | | 2.65 | 0.63 | (2) | 119.00 | | (1) |
| 77 | | 2.07 | 0.50 | (3) | 759.00 | | (1) |
| 78 | | 3.01 | 0.23 | (2) | 98.40 | | (1) |
| 79 | | 2.25 | 1.14 | (3) | 173.00 | | (1) |
| 80 | | 130.10 | 18.16 | (3) | — | | |
| 81 | | 0.88 | 0.18 | (9) | 43.90 | | (1) |
| 82 | | 0.96 | 0.21 | (9) | 136.50 | | (1) |
| 83 | | 7.08 | 3.93 | (2) | 77.70 | | (1) |

TABLE 6-continued
| # | COMPOUND | SIGMA IC$_{50}$ (nM) MEAN | SEM | (n) | 5HT-1A (nM) MEAN | SEM | (n) |
|---|---|---|---|---|---|---|---|
| 84 | 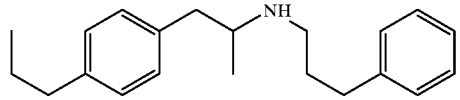 | 6.43 | 0.50 | (2) | 168.00 | | (1) |
| 85 | 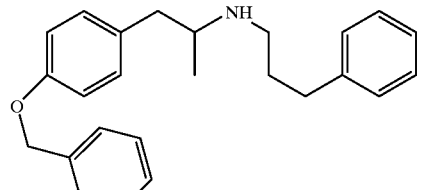 | 28.15 | 4.65 | (2) | 1150.00 | | (1) |
| 86 | 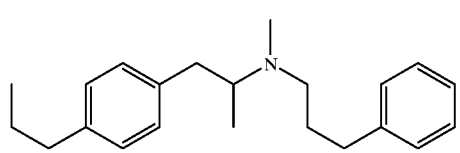 | 2.43 | 1.12 | (2) | 502.00 | | (1) |
| 87 | 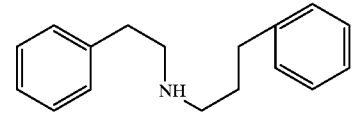 | 21.83 | 2.86 | (3) | 67.40 | | (1) |
| 88 | 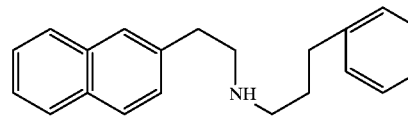 | 53.40 | 9.80 | (3) | — | | |
| 89 | 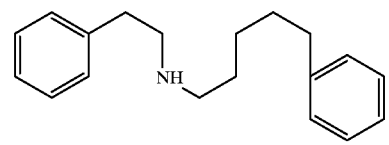 | 2.74 | 0.40 | (4) | 106.00 | 7.00 | (2) |
| 90 | 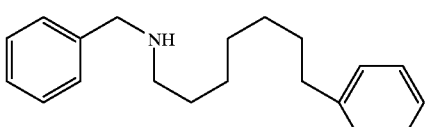 | 3.95 | 0.53 | (4) | 3208.00 | 148.00 | (2) |
| 91 | 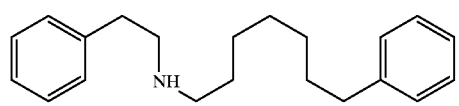 | 4.07 | 0.52 | (4) | 732.50 | 111.50 | (2) |
| 92 | 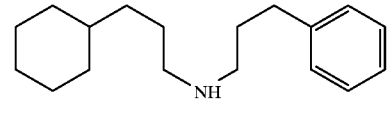 | 2.99 | 0.28 | (4) | 26.30 | 1.10 | (2) |
| 93 | 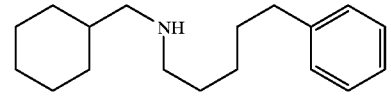 | 1.40 | 0.05 | (4) | 596.50 | 2.50 | (2) |

TABLE 6-continued
| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 94 | 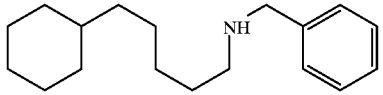 | 4.02 | 0.27 | (4) | 5549.50 | 119.50 | (2) |
| 95 | 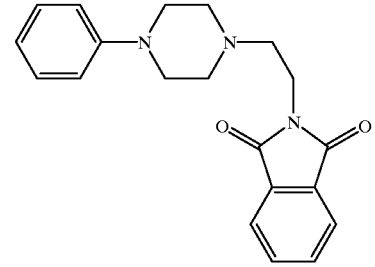 | 16950.00 | | (1) | — | | |
| 96 | 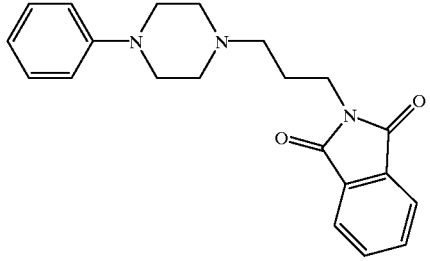 | 141.00 | 29.61 | (3) | — | | |
| 97 | 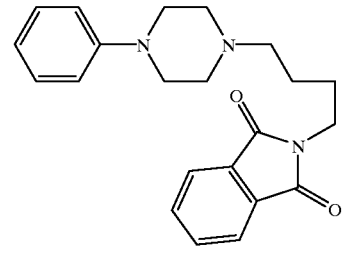 | 20.33 | 4.73 | (3) | — | | |
| 98 | 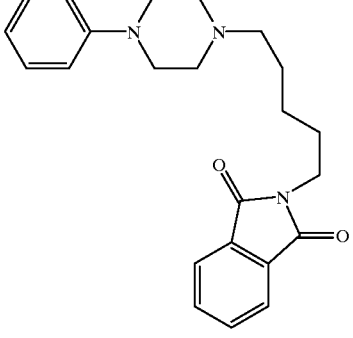 | 6.18 | 1.12 | (4) | 2.23 | 0.84 | (2) |
| 100 | 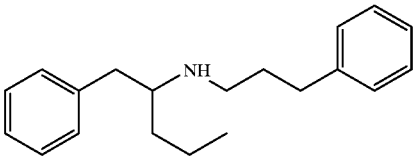 | 25.65 | 0.75 | (2) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 101 | | 15.70 | 1.20 | (2) | — | | |
| 102 | | 6693.50 | 1423.50 | (2) | — | | |
| 103 | | 75.20 | 36.80 | (2) | — | | |
| 104 | | 76.15 | 17.05 | (2) | — | | |
| 105 | | 9.50 | 3.38 | (3) | 4956.50 | 565.50 | (2) |
| 106 | | 49.75 | 8.65 | (2) | — | | |
| 107 | | 10,000.00 | 0.00 | (2) | — | | |
| 108 | | 37.85 | 0.65 | (2) | — | | |
| 109 | | 184.50 | 12.50 | (2) | — | | |
| 110 | | 3.62 | 0.84 | (3) | 116.90 | 22.20 | (2) |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 111 | | 2.73 | 0.58 | (3) | 92.20 | 22.10 | (2) |
| 112 | | 2.65 | 0.41 | (3) | 8243.00 | 685.00 | (2) |
| 113 | | 2.22 | 0.32 | (3) | 2148.00 | 105.00 | (2) |
| 114 | | 6.71 | 1.07 | (3) | 34000 | 24,000 | (2) |
| 115 | | 3.04 | 0.42 | (3) | 20000 | 10000 | (2) |
| 116 | | 10.13 | 8.28 | (2) | — | | |
| 117 | | 2.11 | 0.14 | (3) | 781.50 | 258.50 | (2) |
| 118 | | 2.14 | 0.21 | (3) | 1967.00 | 394.00 | (2) |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 119 | | 21.40 | 4.80 | (2) | — | | |
| 120 | | 64.70 | 2.40 | (2) | — | | |
| 124 | | 2.05 | 0.25 | (3) | — | | |
| 125 | | 38.83 | 9.05 | (2) | — | | |
| 126 | | 219.33 | 7.45 | (3) | — | | |
| 127 | | 10.57 | 1.28 | (3) | — | | |
| 128 | | 2.87 | 0.72 | (3) | — | | |
| 129 | | 2.29 | 1.37 | (3) | — | | |
| 130 | | 4.23 | 0.14 | (3) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 131 | [structure] | 46.90 | 15.45 | (3) | — | | |
| 133 | [structure, S (+)] | 6.44 | 1.77 | (3) | — | | |
| 134 | [structure, S (+)] | 198.77 | 74.48 | (3) | — | | |
| 135 | [structure] | 13.50 | 4.37 | (3) | — | | |
| 136 | [structure] | 1.78 | 1.32 | (3) | — | | |
| 137 | [structure] | 1.11 | 0.52 | (3) | — | | |
| 138 | [structure] | 2.67 | 0.37 | (3) | — | | |
| 140 | [structure] | 69.03 | 13.28 | (4) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 144 | *[structure: phenyl-(CH2)4-NH-CH2CH2-(2-methoxyphenyl)]* | 4.39 | 0.95 | (3) | — | | |
| 145 | *[structure: phenyl-(CH2)4-NH-CH2CH2-(3-methoxyphenyl)]* | 1.63 | 0.39 | (3) | — | | |
| 146 | *[structure: phenyl-(CH2)4-NH-CH2CH2-(4-methoxyphenyl)]* | 2.38 | 0.27 | (3) | — | | |
| 147 | *[structure: benzylpiperidine]* | 117.3 | 63.05 | (3) | — | | |
| 148 | *[structure: 1-(2-phenylethyl)-4-hydroxy-4-phenylpiperidine]* | 6.43 | 0.85 | (3) | — | | |
| 149 | *[structure: 1-(2-phenylethyl)-4-tert-butyl-4-hydroxypiperidine]* | 21.48 | 2.24 | (4) | — | | |
| 150 | *[structure: cyclohexyl-(CH2)4-piperidine]* | 0.96 | 0.24 | (3) | — | | |
| 151 | *[structure: cyclohexyl-CH2-NH-(CH2)3-cyclohexyl]* | 1.39 | 0.10 | (3) | — | | |
| 152 | *[structure: cyclohexyl-CH2-N(CH3)-(CH2)3-cyclohexyl]* | 1.76 | 0.23 | (3) | — | | |

TABLE 6-continued
| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 153 | 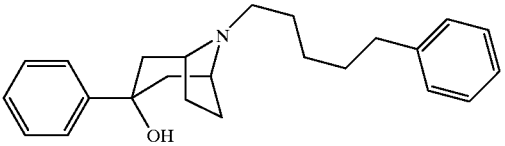 | 2.21 | 0.39 | (3) | — | | |
| 154 | 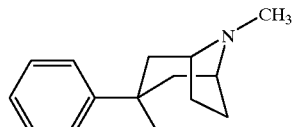 | 3955 | 711 | (3) | — | | |
| 155 | 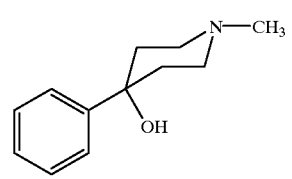 | 1866 | 113 | (3) | — | | |
| 156 | 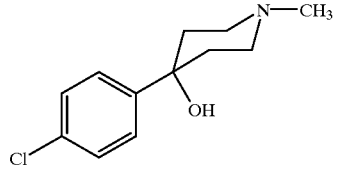 | 130.63 | 21.39 | (3) | — | | |
| 157 | 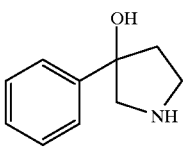 | 6113 | 2790 | (2) | — | | |
| 159 | 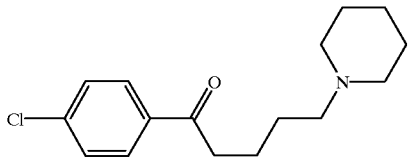 | 1.30 | 0.27 | (3) | — | | |
| 160 | 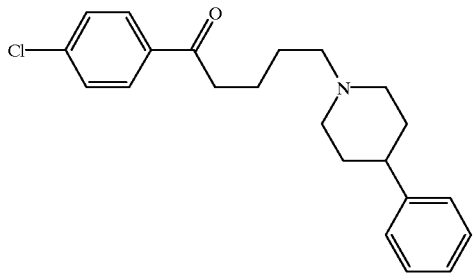 | 0.62 | 0.14 | (3) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 161 | 4-methoxyphenyl ketone with (CH$_2$)$_4$-piperidine | 10.87 | 1.70 | (3) | — | | |
| 162 | 4-methoxyphenyl ketone with (CH$_2$)$_4$-(4-phenylpiperidine) | 0.90 | 0.05 | (3) | — | | |
| 163 | phenyl-(CH$_2$)$_7$-piperidine | 1.74 | 0.06 | (3) | — | | |
| 164 | 4-methoxyphenyl-(CH$_2$)$_5$-piperidine | 5.19 | 1.03 | (2) | — | | |
| 165 | 4-methoxyphenyl-(CH$_2$)$_5$-(4-phenylpiperidine) | 1.27 | 0.05 | (2) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 166 | | 1.03 | 0.01 | (2) | — | | |
| 167 | | 1.96 | 0.52 | (3) | — | | |
| 169 | | 22.80 | 2.30 | (2) | — | | |
| 170 | | 4.18 | 0.56 | (2) | — | | |
| 171 | | 1.19 | 0.24 | (2) | — | | |
| 172 | | 7.46 | 1.03 | (2) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 173 | | 17.20 | 4.60 | (2) | | — | |
| 174 | | 1.10 | 0.35 | (3) | | — | |
| 175 | | 42.90 | 1.64 | (3) | | — | |
| 177 | | 7.37 | 1.57 | (2) | | — | |
| 178 | | 0.896 | 0.077 | (2) | | — | |
| 179 | | 2.82 | 0.02 | (2) | | — | |
| 180 | | 2.24 | 0.62 | (2) | | — | |
| 181 | | 1.08 | 0.06 | (2) | | — | |
| 182 | | 4.68 | 0.14 | (2) | | — | |

TABLE 6-continued
| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 183 |  | 1.97 | 0.05 | (3) | — | | |
| 184 | 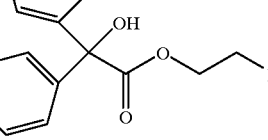 | 1.98 | 0.14 | (2) | — | | |
| 185 | 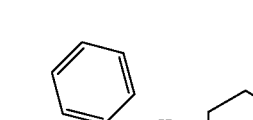 | 1736 | 732 | (2) | — | | |
| 186 | 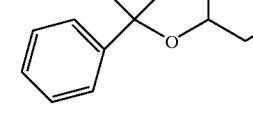 | 656 | 165 | (2) | — | | |
| 187 | 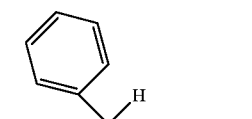 | 50.6 | 11.7 | (2) | — | | |
| 188 | 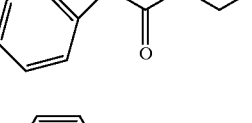 | 174 | 27 | (2) | — | | |
| 189 | 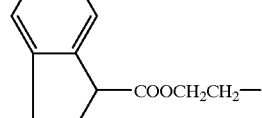 | 13.5 | 3.3 | (2) | — | | |

TABLE 6-continued

| # | COMPOUND | SIGMA IC$_{50}$ (nM) | | | 5HT-1A (nM) | | |
|---|---|---|---|---|---|---|---|
| | | MEAN | SEM | (n) | MEAN | SEM | (n) |
| 190 | | 1.07 | 0.07 | (2) | — | | |
| 191 | | 8.14 | — | (1) | — | | |

Example 5

Structure-Activity Relationship of the Sigma Receptor Ligands

The binding data reproduced in Tables 4–6 allows the identification of groups of compounds having high binding and selectivity for the sigma receptors. For example, it has been determined that the α-methyl group on N-(3-phenylpropyl)isopropylamine (Ki=22 nM) is not required for high binding to the sigma receptor. The corresponding des-methyl compound N-(3-phenylpropyl)-2-phenethylamine binds with comparable affinity (Ki=19 nM). This des-methyl compound possesses two carbon atoms between the phenyl ring and the terminal amine and, on the other side of the molecule, possesses three carbon atoms between the amine and the second phenyl ring (see Table 7; x=2, y=3). A systematic comparison of phenylalkylamine derivatives with varrying x and y values is shown in Table 7.

As shown in Table 7, the increase of x from 2 to 3 resulted in the retention of affinity. Interestingly, the total carbon chain length does not appear to be critical for high binding to the sigma receptor. The highest affinity agents are those where either x or y=5. Thus, a phenylpentylamine is optimal while the length of the chain on the other side of the molecule appears to be inconsequential.

Since a carbon length of five atoms is optimal for high binding, and if the substituents on the other side of the molecule are relatively less important, then the second phenyl ring may not be important. Therefore, N-methyl-N-propyl-5-phenylpentylamine, a des-phenyl analog, was prepared and found to bind with high affinity (Ki=2.2 nM).

Where x and y=3, it has also been found that replacement of one of the phenyl rings with a cyclohexyl ring (Ki=2.5 nM) resulted in a nearly six-fold increase in affinity. Furthermore, the cyclohexyl analog N-benzyl-(5-cyclohexyl)pentylamine, where the cyclohexyl group is separated from the amine by five carbon atoms, also binds with high affinity (Ki=1.3 nM).

Taken together, these data suggest that (a) phenylpentylamines bind with high affinity to the sigma receptor, (b) that the nature of the amine substituent is relatively unimportant, and (c) that the phenyl ring of the phenylpentylamines may be replaced by a cyclohexyl ring with retention (and an increase) of affinity.

TABLE 7

Phenyl-(CH$_2$)$_x$-NH—(CH$_2$)$_y$-Phenyl

| x | y | Ki (nM) |
|---|---|---|
| 1 | 1 | 175 |
| 1 | 4 | 13 |
| 1 | 5 | 2.0 |
| 1 | 7 | 3.6 |
| 2* | 3 | 19 |
| 2 | 4 | 5.5 |
| 2 | 5 | 2.4 |
| 2 | 7 | 4.1 |
| 3 | 3 | 14 |
| 3 | 4 | 7.0 |
| 3 | 5 | 1.8 |
| 3 | 6 | 2.6 |
| 4 | 4 | 6.7 |
| 4 | 5 | 2.5 |
| 5 | 1 | 2.0 |
| 5 | 2 | 2.4 |
| 5 | 3 | 1.8 |
| 5 | 4 | 2.5 |

*= des-methyl N-(3-phenylpropyl)isopropylphenylamine

With regard to sigma selectivity over 5-HT$_{1A}$, the unsubstituted phenyl derivative N-(3-phenylpropyl)-1-isopropylamine (cmp. no. 1) exhibits only a 4-fold selectivity for sigma receptors. Aromatic substitution enhances affinity for sigma receptors whereas 5-HT$_{1A}$ affinity remains relatively constant. Consequently, these aromatic substituted derivatives bind with a relatively low, but constant selectivity. Next, the effect of terminal amine modification was examined where the aromatic portion was held constant as a phenyl group. Replacement of the benzylic methylene group of cmp. #1 by an oxygen atom, carbonyl group, or sp-hybridized carbon atom (cmps. 8, 9 and 25) gave little effect. Removal of the a-methyl group of cmp. #1 (R(-)) seems to enhance 5-HT$_{1A}$ affinity. The optical isomers of cmp. #1 bind at sigma receptors with comparable affinity; however, the S(+) isomer binds at 5-HT$_{1A}$ receptors with only one-tenth the affinity of its antipode resulting in a 48-fold selectivity. Similar results were obtained with the isomers of N-(2-ethylphenyl)isopropylamine (cmp. #7). N-Monomethylation (e.g. cmps. 45 and 69) also seems to enhance sigma affinity and selectivity. To further substantiate this finding, N-methyl-N-(3-propylphenyl)-1-(4-n-propylphenyl)-isopropylamine was prepared and found to have the highest and most selective affinity for the sigma receptor.

Example 6

Further Structure-Activity Studies of 5-Pentylamine Derivatives

With N-substituted 5-phenylpentylamines, the length of alkyl chain that separates the amine from its aromatic (phenyl-B) substituent has little influence on affinity (e.g., compare 76, 77, 89, and 111; Ki=2.0≅2.7 nM). It seems unlikely that the phenylethylamines and phenylpentyl amines bind in exactly the same manner at the sigma receptors due to the difference in chain length. In order to account for the binding of these compounds, the phenylethylamines and the phenylpentylamines may utilize different aromatic binding sites. These results prompted a further investigation of 5-phenylpentylamine derivatives as sigma ligands.

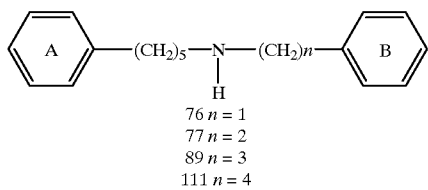

76 n = 1
77 n = 2
89 n = 3
111 n = 4

CHEMISTRY:

The compounds in Table 10 were synthesized by one of the methods described (A-H). Most of the compounds were prepared in two or three steps using either acylation and reduction of the intermediate amide or direct alkylation procedures. The amides were prepared either from the acyl halide and an amine or directly using ethyl chloroformate, an appropriate acid and an amine. Subsequent reduction by lithium aluminum hydride afforded the target amines. Following this procedure, the benzyl protected analog of compound 135 was obtained and subsequent hydrogenolysis produced the desired compound Compounds 136 and 152 were obtained by methylating the corresponding secondary amines using Eschweiler-Clark reductive alkylation procedure. Compounds 173 and 172 were prepared by O-demethylation of 144 and 145 respectively, using concentrated hydrobromic acid solution. Other target compounds prepared either by direct alkylation (method C) or by reductive alkylation (method E), using suitable aldehydes and appropriate amines.

EXPERIMENTAL

Synthesis: Proton magnetic resonance spectra were obtained on JEOL FX90Q or QE 300 (300 MHz) spectrometers with tetramethylsilane as internal standard. All spectra are consistent with the assigned structures. Melting points were determined on a Thomas Hoover apparatus and are uncorrected. Elemental analyses were performed by Atlantic Microlab and determined values are within 0.4% of calculated values.

Method A

H-Cyclohexylmethyl-5-cyclohexylpentylamine Hydrochloride (151). A solution of ethyl chloroformate (1.8 g, 8.2 mmol) in methylene chloride (25 mL) was added in a dropwise manner to a stirred ice-cooled solution of cyclohexanepentanoic acid (3 g, 8.1 mmol) and $Et_3N$ (1.7 g, 8.1 mmol) in dry methylene chloride (50 ml) under $N_2$, over 10 min. Stirring was continued for 30 min. and cyclohexylmethylamine (1.8 g, 8.1 mmol) in methylene chloride (25 ml) was added dropwise over 5 mins. Stirring was allowed to continue for an additional 3 h after which the reaction mixture was washed water (50 mL) and dried ($MgSO_4$). Solvent was removed in vacuo to afford an oil which was crystallized from $FeOH-H_2O$ (4.1 g, 91%); mp 69–72° C. A solution of the amide (3.8 g, 14 mmol) in THF (50 mL) was added dropwise to a suspension of $LiAlH_4$ (2.6 g, 5 eq) in THF (100 mL). The reaction mixture was heated under reflux in a stream of $N_2$ for 20 h. Excess $LiAlH_4$ was decomposed by the gentle addition of $H_2O$ and 10% NaOH solution. Solid matter was removed by filtration and solvent was removed in vacuo to obtain an oily residue. The residue was taken up in $Et_2O$, dried ($MgSO_4$) and solvent was removed under reduced pressure to afford an oil (3.0 g, 80%). The hydrochloride salt, obtained by the addition saturated solution of ethereal HCl to an ethereal solution of 151 (free base), was recrystallized MeOH/EtOAc; mp 223–224° C. (see Table 8).

Method B

N-Methyl-N-hexyl-2-phenylethylamine Hydrogen Oxalate (130). A solution of hexanoyl chloride (1 g, 7.4 mmol) in THF (40 mL) was added in a dropwise manner to a stirred solution of N-methyl-2-phenylethylamine (1 g, 7.4 mmol) and $Et_3N$ (2.3 g, 20 mmol) in THF (100 mL) cooled to 0° C. The reaction mixture was allowed to stir overnight (20 h) after which the triethylamine salt was removed by filtration and washed with THF (2×20 mL). The combined filtrate and washings were evaporated under reduced pressure and the residue taken up in $CHCl_3$ (30 mL). The chloroform solution was washed with $H_2O$ (30 mL) and dried ($Na_2SO_4$). Solvent was removed in vacuo to obtain an oil which was shown by IR (C=O, 1644cm$^{-1}$) to be an amide (1.5 g, 87%). A solution of the amide (0.5 g, 2.1 mmol) in dry THF (60 mL) was added dropwise to a suspension of $LiAlH_4$ (0.41 g, 11 mmol) in THF(40 mL) under a stream of $N_2$. The mixture was stirred overnight, cooled to 0° C. and the reaction mixture was quenched by cautious addition of water and 15% NaOH solution. Solids were removed by filtration. The filtrate was evaporated to dryness under reduced pressure and the residue was taken up in $Et_2O$ (50 mL and dried ($MgSO_4$). Solvent was removed under reduced pressure to obtain an oil (350 mg, 75%). The oil was converted to the oxalate salt (white crystals) and recrystallized from MeOH/$Et_2O$ solution; mp 139–140° C. (see Table 8).

Method C

N-Methyl-N-propylhexylamine Hydrogen Oxalate (131). A stirred mixture of N-methylpropylamine (1.2 g, 13.7 mmol), 1-bromohexane (3.4 g, 20.5 mmol) and potassium carbonate (3.8 g, 27 mmol) in 1,2-dimethoxyethane (DME) (8 mL) was heated under reflux for 24 h and allowed to cool to room temperature. The solid material was removed by filtration and washed several times with $CHCl_3$. The combined filtrates were evaporated to dryness under reduced pressure and the residue partitioned between $Et_2O$ (30 mL) and 10% NaOH solution (20 mL). The ethereal fraction was washed with $H_2O$ (10 mL) and dried ($Na_2SO_4$). A saturated solution of oxalic acid in anhydrous $Et_2O$ was added to obtain a white solid which was recrystallized from iPrOH/$Et_2O$ (0.4 g, 12%); mp 101–102° C. (see Table 8).

Method D

N-Methyl-N-cyclohexylmethyl-5-cyclohexylpentylamine Hydrochloride (152). A mixture of 151 [CNS#?] (0.5 g, 1.9 n-mol), formic acid (1.1 g, 23 mmol) and formaldehyde solution (37%) (1.85 g, 23 mmol) was heated at about 100° C. for 22 h and allowed to cool to room temperature. A 3N HCl solution (10 mL) was added and the solution extracted with $Et_2O$ (3×25 mL). The ethereal solution, which contained the expected product, was washed with 10% NaOH (30 ML), then water (10 mL) and dried ($MgSO_4$). A saturated ethereal HCl solution was added, solvent removed in vacuo, and the residue recrystallized from MeOH-EtOAc (370 mg, 61%); mp 162–163° C. (see Table 8).

Method E

N-(3-Cyclohexylpropyl)-3-phenylpropylamine Hydrochloride (92). A solution of 3-phenyl propylamine (0.65 g, 5 mmol) and 3-cyclohexylpropionaldehyde (0.75 g, 5.4 mmol) in MeOH (40 mL) was hydrogenated in a Parr bottle containing 10% Pd/C (0.3 g) until sufficient $H_2$ was taken up (40 min). The catalyst was removed by filtration; the filtrate was concentrated to about 10 mL under reduced pressure and added to 1N HCl solution (20 mL). The precipitate was collected by filtration and washed thoroughly with anhydrous $Et_2O$ (3×10 mL). Recrystallization from 2-butanone afforded the desired compound as white shiny plates (0.75 g, 53%); mp 203–205° C. (see Table 8).

Method F

N-[2-(3-hydroxyphenyl)ethyl]-5-phenylpentylamine Hydrobromide (172). A mixture of 145 (free base) (0.19 g, 0.65 mmol) and hydrobromic acid solution (48%) (0.22 mL, 1.3 mmol) was heated at reflux for 2 h and solvent was removed in vacuo. The solid residue was recrystallized from MeOH/anhydrous $Et_2O$ to afford the desired compound (100 mg, 42%); mp 151–153° C. (see Table 8).

Method G

N-Phenyl-5-phenyl pentyl amine Hydrogen Oxalate (135). A mixture of N-benzyl-N-phenyl-5-phenylpentylamine (0.89 g, 2.5 mmol) in EtOH (20 mL) and 10% Pd/C (0.19) was hydrogenated at 50 psi for about 3 h. The catalyst was removed by filtration and the filtrate was evaporated to dryness under reduced pressure. The residue was partitioned between 10% HCl solution (20 mL) and $Et_2O$ (20 mL); the aqueous portion was basified with 10% NaOH and extracted with $Et_2O$ (20 mL). The $Et_2O$ portion was dried ($MgSO_4$) and solvent was removed in vacuo to afford an oil (0.3 g, 49%). The oxalate salt was prepared by the addition of a saturated solution of oxalic acid and subsequently recrystallized from EtOAc; mp 133–134° C. (see Table 8).

Method H

5-Cyclohexylpentylamine Hydrogen Oxalate (126). A solution of cyclohexanepentanoic acid (2 g, 10.9 mmol) in $SOCl_2$ (8 mL) was heated on a steam bath for 3 h. The $SOCl_2$ was removed under vacuum. Chloroform (2×10 mL) was added and reevaporated to give the crude acid chloride as a yellow liquid. A saturated solution of ammonia in dry THF (ammonia gas bubbled through 10 mL of THF for 5 min), was slowly added to a solution of the acid chloride in dry THF (50 mL) while cooling in an ice bath. The reaction mixture was allowed to stir at room temperature for 3 h and was then concentrated to half of its volume and poured onto water (100 mL). The solid was removed by filtration, washed with water and dried ($MgSO_4$). Recrystallization from aqueous MeOH gave 5-cyclohexylvaleramide (1.1 g, 55%); mp 121–122° C. (reported mp 122–123° C.) (Katsellson and Dubinin, *Compt. Rend. Acad. Sci. U.R.S.S.* [N.S.] 4:405 (1936); *Chem. Abstr.* 31:3449 (1937)). A suspension of the amide (183 mg, 1 mmol) in anhydrous $Et_2O$ (9 mL) was slowly added to a stirred suspension of $LiAlH_4$ (114 mg, 3 mmol) in $Et_2O$ (15 mL). After addition was complete, the mixture was heated at reflux for 2 h and then allowed to stir overnight at room temperature. The reaction mixture was cooled to 0° C. and excess $LiAlH_4$ was decomposed by successive addition of water (2 mL), 2N NaOH (2 mL) and water (5 mL). After stirring vigorously for 20 min, the mixture was filtered and the inorganic residue was washed with warm $Et_2O$ (3×8 mL). The combined $Et_2O$ solution was dried over anhydrous $K_2CO_3$ and evaporated to dryness. The residue was distilled under reduced pressure to yield a clear oil (99 mg, 59%); bp 30–36° C. (0.35 mm), Lit. bp 108≧113° C. (15 nm) (Skinner, C. G., et al., *J. Am. Chem. Soc.* 79:2844 (1957)). A solution of the free base in anhydrous $Et_2O$ was added to a solution of oxalic acid (52 mg) in anhydrous $Et_2O$ (8 mL) with continuous shaking. The precipitated solid was recrystallized from MeOH/anhydrous $Et_2O$; mp 164° C. (see Table 8).

Radioligand Binding. The a binding assay was conducted using guinea pig (Taconic) brain membranes and [$^3$H]di-o-tolylguanidine (DTG) as radioligand. Briefly, membranes (P2 microsomal fraction) were diluted 1:3 with 50 mM Tris HCl (pH 7.4) and 0.4 mL was combined with 50 µL [$^3$H]DTG (1–2 nM final concentration) and 50 µL of competing drug or buffer. After 90 min at room temperature, incubation was terminated by rapid filtration under vacuum through Whatman GF/B glass fiber filters using a Brandel 48-well cell harvester. Filters were washed three times with 5 mL of cold Tris HCl buffer and each filter was suspended in 5 mL of Cytoscint (ICN Biomedical). Radioactivity was measured by liquid scintillation spectrometry at a counting efficiency of 50%. Non-specific binding was measured in the presence of 10 µM haloperidol.

| | Microanalytical Data Calculated/Found | | |
|---|---|---|---|
| | C | H | N |
| 152 | 70.56 | 7.61 | 3.92 |
| | 70.43 | 7.59 | 3.93 |
| 136 | 71.66 | 8.11 | 3.63 |
| | 71.37 | 8.08 | 3.59 |
| 144 | 71.94 | 8.45 | 4.20 |
| | 71.88 | 8.49 | 4.19 |
| 8 | 67.54 | 7.29 | 3.75 |
| | 67.47 | 7.33 | 3.69 |
| 145 | 71.94 | 8.45 | 4.20 |
| | 71.87 | 8.49 | 4.21 |
| 172 | 62.02 | 7.12 | 3.81 |
| | 62.01 | 7.22 | 3.81 |
| 146 | 71.18 | 8.48 | 4.15 |
| | 71.23 | 8.46 | 4.17 |
| 135 | 68.90 | 7.06 | 4.23 |
| | 68.52 | 7.22 | 4.23 |
| 112 | 65.99 | 8.80 | 4.53 |
| | 65.82 | 8.75 | 4.51 |
| 130 | 65.99 | 8.80 | 4.53 |
| | 65.92 | 8.79 | 4.57 |
| 131 | 58.27 | 10.19 | 5.66 |
| | 58.20 | 10.17 | 5.66 |
| 193 | 73.06 | 10.22 | 4.75 |
| | 72.95 | 10.23 | 4.74 |
| 92 | 73.06 | 10.22 | 4.73 |
| | 72.96 | 10.22 | 4.77 |
| 126 | 58.10 | 9.76 | 5.23 |
| | 58.18 | 9.77 | 5.22 |
| 127 | 61.60 | 9.97 | 5.12 |
| | 61.51 | 9.96 | 5.12 |
| 128 | 62.71 | 10.16 | 4.92 |
| | 62.69 | 10.17 | 4.87 |
| 125 | 63.94 | 8.19 | 5.10 |
| | 64.03 | 8.24 | 4.98 |
| 94 | 73.06 | 10.22 | 4.73 |
| | 73.12 | 10.27 | 4.78 |
| 23 | 70.55 | 12.01 | 4.57 |
| | 70.36 | 12.01 | 4.57 |
| 24 | 71.21 | 12.11 | 4.37 |
| | 71.27 | 12.04 | 4.33 |

TABLE 8

Physicochemical properties of new sigma receptor ligands

| Compd # | Method | Recryst. Solv. | Mp (°C.) | % Yield[a] | Formula |
|---|---|---|---|---|---|
| 152 | A | PrOH/EtOAc | 140–141 | 49 | $C_{19}H_{25}N \cdot C_2H_2O_4$ |
| 135 | D | PrOH | 141–142 | 73 | $C_{21}H_{29}N \cdot C_2H_2O_4$ |
| 144 | A | MEK | 115 | 37 | $C_{20}H_{27}NO \cdot HCl$ |
| 173 | B | MEK | 173–174 | 2 | $C_{19}H_{25}NO \cdot C_2H_2O_4$ |
| 145 | A | MeOH/Et$_2$O | 160 | 40 | $C_{20}H_{27}NO \cdot HCl$ |
| 172 | F | MeOH/Et$_2$O | 151–153 | 39 | $C_{19}H_{25}NO \cdot HBr$[b] |
| 146 | A | MeOH/Et$_2$O | 233–235 | 33 | $C_{20}H_{27}NO \cdot HCl$[b] |
| 135 | G | EtOAc | 133–134 | 35 | $C_{17}H_{21}N \cdot C_2H_2O_4$[c] |
| 112 | E | EtOAc | 130–131 | 24 | $C_{15}H_{25}N \cdot C_2H_2O_4$ |
| 130 | B | MeOH/Et$_2$O | 139–140 | 65 | $C_{15}H_{25}N \cdot C_2H_2O_4$ |
| 131 | C | iPrOH/Et$_2$O | 101–102 | 12 | $C_{10}H_{23}N \cdot C_2H_2O_4$ |
| 93 | A | iPrOH/Et$_2$O | 171–173 | 39 | $C_{18}H_{29}N \cdot HCl$ |
| 92 | E | MEK | 203–205 | 53 | $C_{18}H_{29}N \cdot HCl$ |
| 126 | H | MeOH/Et$_2$O | 164 | 48 | $C_{11}H_{23}N \cdot C_2H_2O_4$[d] |
| 127 | B | MeOH | 191 | 28 | $C_{12}H_{25}N \cdot C_2H_2O_4$ |
| 128 | B | MeOH | 152 | 25 | $C_{13}H_{27}N \cdot C_2H_2O_4$ |
| 125 | B | MeOH | 163 | 43 | $C_{13}H_{21}N \cdot C_2H_2O_4$ |
| 94 | A | iPrOH/Et$_2$O | 184–185 | 34 | $C_{18}H_{29}N \cdot HCl$ |
| 151 | A | MeOH/EtOAc | 223–224 | 73 | $C_{18}H_{35}N \cdot HCl$[e] |
| 152 | D | MeOH/EtOAc | 162–163 | 61 | $C_{19}H_{37}N \cdot HCl$[e] |

[a]No attempt was made to optimize yields. Yields are overall % yields.
[b]Crystallized with 0.2 moles of H$_2$O.
[c]Crystallized with 0.1 moles of H$_2$O.
[d]Crystallized with 0.5 moles of H$_2$O.
[e]Crystallized with 0.25 moles of H$_2$O.

RESULTS AND DISCUSSION

Binding data are shown in Table 9. N-Methylation of N-substituted phenylethylamines typically doubles and aromatic substitution at the 3- and 4-position has essentially no effect on sigma receptor affinity. N-Methylation of 151 and 111 (i.e., 152 and 136, respectively) doubles affinity (Table 9). Incorporation of phenolic or methoxy groups at the 3- and 4-positions (145, 172, and 146) has little effect on affinity, whereas the 2-hydroxy derivative 8 binds with about 7-fold lower affinity than its unsubstituted parent 89 (Ki=2.4 nM). Excision of the N-alkyl chain separating the amine from phenyl-B, to afford the aniline derivative 135 (Ki=12 nM), reduces affinity by only 6-fold; this decrease in affinity may reflect a decrease in the basicity of the amine.

The above results (i.e., lack of influence of chain length and aromatic substitution on sigma affinity) suggest that the aromatic amine substituent plays only a small role in binding, and that it may be possible to replace the phenyl-B ring with a non-aromatic group. Indeed, compound 122, which may be viewed either as either an N-methyl analog of 89 where the phenyl-B group has been replaced by methyl, or as an analog of 136 where the phenyl group has been eliminated, binds with high affinity (Ki=2.4 nM). Interestingly, the phenyl-A ring can also be replaced by a methyl group (130; Ki=3.8 nM) with little reduction in affinity. Replacement of both phenyl groups by methyl (131; Ki=45 nM) results in a significant reduction in affinity. Apparently, either phenyl-A or phenyl-B can be replaced by a methyl group; however, replacement of both results in decreased affinity.

Because both phenyl groups are unnecessary for binding, we examined several additional compounds bearing a single phenyl. Compound 93, the phenyl-B reduced analog of 151, binds with twice the affinity (Ki=1.2 nM) of 151. Compound 92 (Ki=2.4 nM), an analog of 93 where the position of the amine has been shifted, also binds with high affinity.

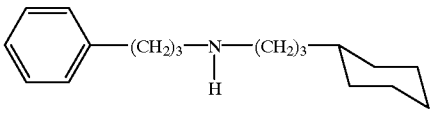

92

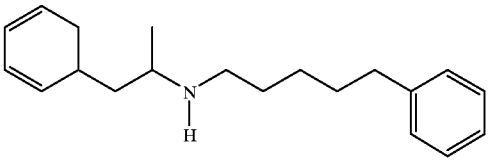

45

Examination of three simple 5-(cyclohexyl)pentylamines, the primary amine 126 (Ki=200 nM), the N-monomethylamine 127 (Ki=10 nM), and the N,N-dimethylamine 128 (Ki=2.6 nM), reveals that tertiary amines are most favorable for binding. The affinity of the latter compound 128, was compared with the aromatic analog 125 (Ki=35 nM), revealing that reduction results in about a 10-fold increase in affinity. However, reduction of the phenyl-A ring of 151 (94; Ki=3.4 nM) results in essentially no change in affinity. This may be related to the fact that 128 and 125 are tertiary amines whereas 94 is a secondary amine; nevertheless, it is apparent from these results that both phenyl-A and phenyl-B can replaced with a cyclohexyl group. The final two compounds examined, 151 and 152, possess two cyclohexyl shortened or lengthened without adverse effect on sigma receptor affinity (e.g., see compounds 151, 89, 111 and 76). That is, affinity is independent of the length of the alkyl chain that separates the phenyl-B ring from the amine. To account for these observations, the sigma receptors may possess at last two distinct aromatic binding sites: one that utilizes the phenyl-B ring of phenylethylamines, and one that utilizes the phenyl-A ring of the phenylpentylamines. The phenyl-B ring of 151, 89, 111 and 76 is unnecessary for binding; it can be replaced by a small alkyl group (e.g. 112) or with a cyclohexyl group (e.g. 131) with retention of affinity. Interestingly, the phenyl-A ring can also be replaced with a methyl or cyclohexyl group (e.g., 130 and 94, respectively) with little change in affinity. Had only one of the phenyl groups been replaceable by methyl (or cyclohexyl) without loss of affinity, this would have provided direct evidence for the two distinct sites on sigma receptors. Nevertheless, in as much as compounds such as 151 and 152 bind with high affinity, it would appear that, independent of mode of binding, an aromatic moiety is not a requirement for high affinity.

TABLE 9

Sigma receptor binding data.*
$X-(CH_2)_5-N(R)-(CH_2)_n-Y$

|  | X | R | n | Y | Ki nM (SEM) |
|---|---|---|---|---|---|
| 77 | Phenyl | H | 1 | Phenyl | 2.0 |
| 89 | Phenyl | H | 2 | Phenyl | 2.4 |
| 111 | Phenyl | H | 3 | Phenyl | 2.7 |
| 76 | Phenyl | H | 4 | Phenyl | 2.5 |
| 137 | Phenyl | Me | 1 | Phenyl | 1.0 (±0.4) |
| 136 | Phenyl | Me | 3 | Phenyl | 1.6 (±1.2) |
| 144 | Phenyl | H | 2 | 2-OMe Phenyl | 4.0 (±0.9) |
| 173 | Phenyl | H | 2 | 2-OH Phenyl | 15.6 (±4.1) |
| 145 | Phenyl | H | 2 | 3-OMe Phenyl | 1.5 (±0.4) |
| 172 | Phenyl | H | 2 | 3-OH Phenyl | 6.8 (±0.9) |
| 146 | Phenyl | H | 2 | 4-OMe Phenyl | 2.2 (±0.3) |
| 135 | Phenyl | H | 0 | Phenyl | 12.2 (±4.0) |
| 112 | Phenyl | Me | 2 | Methyl | 2.4 (±0.4) |
| 130 | Methyl | Me | 2 | Phenyl | 3.8 (±0.1) |
| 131 | Methyl | Me | 2 | Methyl | 45 (±14) |
| 93 | Phenyl | H | 1 | Cyclohexyl | 1.2 (±0.0) |
| 126 | Cyclohexyl | H | 0 | H | 200 (±7) |
| 127 | Cyclohexyl | H | 0 | Methyl | 10 (±1) |
| 128 | Cyclohexyl | Me | 0 | Methyl | 2.6 (±0.7) |
| 125 | Phenyl | Me | 0 | Methyl | 35 (±8) |
| 94 | Cyclohexyl | H | 1 | Phenyl | 3.4 (±0.3) |
| 151 | Cyclohexyl | H | 1 | Cyclohexyl | 1.2 (±0.1) |
| 152 | Cyclohexyl | Me | 1 | Cyclohexyl | 1.6 (±0.2) |

Example 7

Discrimination between the Sigma-I and Sigma-2 Binding Sites

Materials

[$^3$H](+)pentazocine (35 Ci/mmol) was generously provided by Dr. Steven Hunt of DuPont/NEN. [$^3$H]DTG was purchased from DuPont/NEN. (+)Pentazocine was obtained from the NIDA Research Technology Branch, Division of Research. Guinea pig whole membrane preparations (P2 microsomal fraction) were obtained and used as described by Weber, E. et al., Proc. Natl. Acad. Sci 83:8784–8788 (1986).

Sigma-1 binding assay ([$^3$H](+)pentazocine)

The sigma-i selective binding assay was performed using [$^3$H](+)pentazocine as the radioligand (3–4 nM final concentration unless otherwise specified) and approximately 100 μg of guinea pig membranes in a final volume of 500 μl of 50 mM TRIS-HCl, pH 8.0. Non-specific binding was determined in the presence of 10 μM haloperidol. For the standard equilibrium assay, the mixtures were incubated for 4–5 hours at 37° C., quenched with 4 ml of ice cold incubation buffer and rapidly filtered over Whatman GF/B fiber filters, followed by three 4 ml rinses with additional ice cold incubation buffer. The radioactivity on the filters was determined by scintillation spectrometry at an efficiency of about 50% using Cytoscint (ICN) scintillation fluid.

Sigma-2 binding assay

The sigma-2 selective binding assay was performed using about 2 nM [$^3$H]DTG as the radioligand in the presence of 200 nM (+)pentazocine to block the sigma-1 sites, with 400 μg of guinea pig membranes in a total volume of 0.5 ml of 50 mM TRIS-HCl, pH 7.4. Non-specific binding was determined in the presence of 10 μM haloperidol. For the standard equilibrium assay, the mixtures were incubated for 30 min. at room temperature, then filtered and the radioactivity determined as described above.

Data Analysis

Equilibrium binding data were analyzed by least squares nonlinear regression techniques as described by Fischer, J. B. and Schonbrunn, A., J. Biol. Chem. 263:2808–2816 (1988). Two site binding curves were fit to an equation describing the sum of two independent sites with Hill slopes of 1. Affinity constants ($K_i$) values were calculated from $IC_{50}$ values using the Cheng-Prussoff equation (Cheng, Y.-C. and Prusoff, W. H., Biochem. Pharm. 22:3099–3108 (1973)). The results are reported in Table 10 for DTG, several lots of an N,N'-disubstituted guanidine, haloperidol and BMY-14802, as well as for certain of the compounds of the invention. For comparison, Table 11 shows the sigma-1 and sigma-2 binding data for a number of other known compouds.

TABLE 10

| cmp. # | | SIGMA-1 (NM) KI vs. 3H-PENTAZOCINE | | | SIGMA-2 (NM) KI vs. 3H-DTG + PENTAZOCINE | | | S1/S2 Ratio |
|---|---|---|---|---|---|---|---|---|
| | | MEAN | SEM | n | MEAN | SEM | n | |
| | N,N'-Di-(o-tolyl)guanidine | 40.67 | 1.67 | 3 | 52.39 | 4.14 | 4 | 0.776 |
| | Haloperidol | 0.47 | 0.09 | 3 | 11.50 | 0.55 | 3 | 0.041 |
| | BMY-14802 | 271.00 | 52.00 | 2 | 132.60 | 43.86 | 3 | 2.044 |
| 1 | R(−)N-(1-phenyl-2-propyl)-3-phenylpropylamine | 10.75 | 2.06 | 2 | 60.75 | 1.85 | 2 | 0.177 |
| 10 | (±) N-(1-phenyl-2-propyl)-4-phenylbutylamine | 4.68 | 1.26 | 3 | 53.20 | 6.00 | 2 | 0.088 |

TABLE 10-continued

| cmp. # | | SIGMA-1 (NM) KI vs. 3H-PENTAZOCINE | | | SIGMA-2 (NM) KI vs. 3H-DTG + PENTAZOCINE | | | S1/S2 Ratio |
|---|---|---|---|---|---|---|---|---|
| | | MEAN | SEM | n | MEAN | SEM | n | |
| 11 | R(−) N-(1-phenyl-2-propyl)-3-(1-naphthyl)propylamine | 8.60 | 1.40 | 2 | 280.00 | 31.00 | 2 | 0.31 |
| 12 | R(−) N-(1-phenyl-2-propyl)-3-(2-naphthyl)propylamine | 5.73 | 1.71 | 3 | 258.00 | 48.00 | 2 | 0.022 |
| 15 | Di-(3-phenylpropyl)-amine | 11.37 | 2.00 | 3 | 63.90 | 1.37 | 3 | .178 |
| 16 | (±) N-[1-(1'-Naphthyl)-2-propyl]-3-phenylpropylamine | 9.25 | 0.75 | 2 | 152.00 | 14.00 | 2 | 0.061 |
| 17 | (±) N-[1-(2'-Naphthyl)-2-propyl]-3-phenylpropylamine | 31.00 | 13.00 | 2 | 222.00 | 82.00 | 2 | 0.140 |
| 18 | N-(3-phenylpropyl)-1-(2-naphthyl)-2-propylamine | 25.70 | 6.30 | 2 | 15.13 | 2.61 | 3 | 1.7 |
| 20 | (±) N-[1-(3'-Bromophenyl)-2-propyl]-3-phenylpropylamine | 9.65 | 2.35 | 2 | 26.15 | 10.35 | 2 | 0.369 |
| 21 | (±) N-[1-(4'-Bromophenyl)-2-propyl]-3-phenylpropylamine | 11.97 | 2.85 | 3 | 39.13 | 9.20 | 4 | 0.306 |
| 22 | (±) N-[1-(4'-Iodophenyl)-2-propyl]-3-phenylpropylamine | 17.67 | 3.64 | 3 | 76.03 | 6.29 | 4 | 0.232 |
| 23 | (±) N-[1-(3'-Trifluoromethyl)-2-propyl]-3-phenylpropylamine | 8.75 | 4.05 | 4 | 20.85 | 3.48 | 4 | 0.420 |
| 32 | 1-(3'-Chlorophenyl)-4-(2-phenylethyl)piperazine | 14.95 | 7.40 | 4 | 42.43 | 4.02 | 3 | 0.352 |
| 34 | (±) 1-Phenyl-2-aminopentane | 1177.00 | 415.64 | 3 | 10276.00 | 276.00 | 3 | 0.115 |
| 40 | 4-Hydroxy-4-phenyl-1-(3-phenylpropyl)piperidine | 0.68 | 0.36 | 3 | 9.20 | 2.07 | 3 | 0.074 |
| 40 | 4-Hydroxy-4-phenyl-1-(3-phenylpropyl)piperidine | 0.68 | 0.36 | 3 | 7.03 | 2.87 | 3 | 0.096 |
| 43 | N-(3-phenylpropyl)-1-phenyl-2-propylamine | 51.47 | 11.44 | 3 | 37.50 | 11.02 | 3 | 1.37 |
| 44 | N-(4-phenylbutyl)-1-phenyl-2-propylamine | 19.43 | 4.96 | 3 | 35.80 | 3.34 | 3 | .543 |
| 45 | N-(5-phenylpentyl)-1-phenyl-2-propylamine | 0.88 | 0.21 | 4 | 18.47 | 2.27 | 3 | .048 |
| 60 | N-(2-Naphthyl)piperazine | 219.87 | 60.75 | 3 | 5599.00 | 610.04 | 3 | 0.039 |
| 64 | N-Phenyl-N'-propylpiperazine | 81.60 | 13.29 | 3 | 538.00 | 42.00 | 3 | 0.152 |
| 70 | Di-[3-(2'-Naphthyl)propyl]amine | — | — | 0 | 10000.00 | 0.00 | 2 | — |
| 71 | N-(4-phenylbutyl)phenethylamine | 2.60 | 0.31 | 4 | 118.67 | 14.99 | 3 | 0.022 |
| 74 | Di-N-[3-(2'-naphthyl)propyl-N-methylamine | 29.98 | 11.06 | 3 | 460.75 | 165.40 | 4 | 0.065 |
| 75 | N-(4-phenylbutyl)benzylamine | 9.61 | 2.88 | 5 | 161.63 | 31.37 | 3 | 0.059 |
| 76 | N-(5-phenylpentyl)-(4-phenyl)butylamine | 0.48 | 0.05 | 2 | 68.00 | 5.00 | 2 | 0.007 |
| 77 | N-(5-phenylpentyl)benzylamine | 0.32 | 0.10 | 3 | 34.33 | 6.87 | 3 | 0.009 |
| 79 | N-(4-phenylbutyl)-N'-benzylpiperazine | 0.17 | 0.02 | 4 | 6.99 | 1.14 | 3 | 0.024 |
| 80 | N-4(4-phenylbutyl)-N'-benzoylpiperazine | 71.83 | 2.51 | 3 | 965.00 | 65.00 | 2 | 0.074 |
| 83 | N-(3-phenylpropyl)-1-(p-ethoxyphenyl)-2-propylamine | 3.38 | 0.30 | 2 | 33.50 | 0.50 | 2 | 0.101 |
| 87 | N-(3-phenylpropyl)phenethylamine | 11.27 | 0.97 | 2 | 90.10 | 37.90 | 2 | 0.125 |
| 89 | N-(5-phenylpentyl)phenethylamine | 0.17 | 0.00 | 2 | 14.60 | 5.31 | 2 | 0.012 |
| 90 | N-(7-phenylheptyl)benzylamine | 2.30 | 1.00 | 2 | 38.47 | 9.44 | 3 | 0.060 |
| 91 | N-(7-phenylheptyl)phenethylamine | 1.47 | 0.63 | 4 | 33.23 | 10.16 | 3 | 0.044 |
| 94 | N-(5-cyclohexylpentyl)benzylamine | 0.81 | 0.17 | 3 | 43.57 | 6.76 | 3 | 0.019 |
| 96 | N-phenyl-N'-(3-(1-phthalimido)propyl)piperazine | 3100.33 | 1597.63 | 3 | 149.18 | 18.06 | 4 | 87.819 |
| 97 | N-phenyl-N'-(4-1-phthalimido)butyl)piperazine | 195.33 | 31.78 | 3 | 20.38 | 0.88 | 4 | 9.587 |
| 101 | N-(4-phenylbutyl)-1-phenyl-2-butylamine | 2.70 | 0.60 | 2 | 104.10 | 12.90 | 2 | 0.026 |
| 103 | N-(4-phenyl-3(E)-butenyl)-N'-methylpiperazine | 28.67 | 3.67 | 3 | 2544.67 | 699.93 | 3 | 0.011 |
| 104 | N-(4-phenyl-3(Z)-butenyl)-N'-methylpiperazine | 28.67 | 6.67 | 3 | 1306.00 | 54.00 | 2 | 0.022 |
| 105 | N-(4-(3-trifluoromethyl)-3-(Z)-butenyl)-N-methylpiperazine | 1.50 | 0.26 | 3 | 176.53 | 53.26 | 3 | 0.008 |
| 106 | N-(4-phenyl)-N'-methylpiperazine | 19.33 | 3.93 | 3 | 898.80 | 180.96 | 5 | 0.022 |
| 111 | N-(5-phenylpentyl)-3-phenylpropylamine | 0.28 | 0.03 | 3 | 9.84 | 4.58 | 3 | 0.029 |

TABLE 10-continued

| | cmp. # | SIGMA-1 (NM) KI vs. 3H-PENTAZOCINE | | | SIGMA-2 (NM) KI vs. 3H-DTG + PENTAZOCINE | | | S1/S2 |
|---|---|---|---|---|---|---|---|---|
| | | MEAN | SEM | n | MEAN | SEM | n | Ratio |
| 112 | N-methyl-N-propyl-5-phenylpentylamine | 0.29 | 0.05 | 3 | 40.48 | 10.77 | 5 | 0.007 |
| 113 | N-Methyl-N-(3-phenylpropyl)-1-phenylisopropylamine | 0.51 | — | 1 | 4.87 | 0.72 | 3 | 0.105 |
| 117 | N-(5-phenylpentyl)-4-benzylpiperidine | 0.58 | 0.26 | 3 | 2.78 | 0.33 | 3 | 0.210 |
| 120 | N-(4-(1-phthalimido)butyl)-N'-(o-methoxyphenyl)piperazine | 511.67 | 115.79 | 3 | 76.57 | 24.14 | 3 | 6.683 |
| 124 | N-(5-phenylpentyl)piperidine | 0.48 | 0.01 | 3 | 49.90 | 8.87 | . | 0.010 |
| 125 | N,N-Dimethyl-5-phenylpentylamine | 10.45 | 1.07 | 3 | 965.00 | 55.00 | 2 | 0.011 |
| 126 | 5-cyclohexylpentylamine | 191.33 | 16.76 | 3 | 2554.00 | 64.00 | 2 | 0.075 |
| 127 | N-methyl-5-cyclohexylpentylamine | 6.78 | 0.92 | 4 | 346.00 | 29.00 | 2 | 0.020 |
| 128 | N,N-Dimethyl-5-cyclohexylpentylamine | 0.26 | 0.03 | 3 | 195.33 | 27.82 | 3 | 0.001 |
| 129 | N-Benzyl-N'-(5-phenylpentyl)-piperazine | 0.41 | 0.04 | 2 | 11.32 | 1.70 | 3 | .036 |
| 134 | N-Benzyl-N-(3-phenylpropyl)-1-phenyl-2-propylamine | 127.90 | 25.04 | 5 | 470.75 | 37.40 | 4 | 0.272 |
| 137 | N-Benzyl-N-methyl-5-phenylpentylamine | 0.19 | 0.04 | 2 | 12.55 | 0.15 | 2 | 0.015 |
| 140 | N-(3-phenylpropyl)piperidine | 48.94 | 4.39 | 3 | 146.50 | 3.50 | 2 | |

TABLE 11

| COMPOUND | SIGMA-1 (NM) KI vs. 3H-PENTAZOCINE | | | SIGMA-2 (NM) KI vs. 3H-DTG + PENTAZOCINE | | | S1/S2 |
|---|---|---|---|---|---|---|---|
| | MEAN | SEM | n | MEAN | SEM | n | Ratio |
| (+)3-PPP | 47.67 | 1.45 | 3 | 493.00 | 40.07 | 3 | 0.097 |
| (−)3-PPP | 312.33 | 17.89 | 3 | 1261.00 | 97.32 | 3 | 0.248 |
| (+)Butaclamol | 583.67 | 177.34 | 3 | 1399.67 | 86.15 | 3 | 0.417 |
| (−)Butaclamol | 69.33 | 14.89 | 3 | 3422.67 | 723.43 | 3 | 0.020 |
| Chlorpromazine | 336.00 | 23.58 | 4 | 714.00 | 201.00 | 2 | 0.471 |
| Dextromethorphan | 522.00 | 239.08 | 3 | 14990.00 | 2653.32 | 3 | 0.035 |
| Fluoxetine | 56.75 | 8.8353 | 4 | 10000 | 0 | 3 | |
| Fluphenazine | 31.67 | 7.62 | 3 | 67.33 | 8.50 | 4 | 0.470 |
| Ifenprodil | 5.83 | 0.64 | 3 | 2.39 | 0.39 | 3 | 2.444 |
| (+)Pentazocine | 1.60 | 0.09 | 4 | 906.33 | 27.39 | 3 | 0.002 |
| (−)Pentazocine | 114.00 | 20.30 | 3 | 242.33 | 8.97 | 3 | 0.470 |
| Perphenazine | 25.10 | 7.45 | 3 | 80.35 | 0.05 | 2 | 0.312 |
| Pramiracetam | 10000.00 | 0.00 | 3 | 10000.00 | — | 1 | 1.000 |
| Remoxipride | 312.00 | 36.58 | 4 | 1617.00 | 267.38 | 3 | 0.193 |
| Rimoazole | 1156.00 | 183.06 | 3 | 264.67 | 86.11 | 3 | 4.368 |
| (+)SKF 10047 | 148.00 | 19.09 | 3 | 16173.25 | 3447.26 | 4 | 0.009 |
| (−)SKF 10047 | 3640.00 | 825.19 | 3 | 9131.25 | 1574.11 | 4 | 0.399 |
| Thioridazine | 520.50 | 81.22 | 4 | 334.50 | 82.50 | 2 | 1.556 |
| Trifluperizine | 561.25 | 135.80 | 4 | 160.50 | 47.50 | 2 | 3.497 |
| Spiperone | 10000.00 | — | 1 | — | — | 0 | — |

EXAMPLE 8

Structure-Activity Analysis with Regard to Sigma-1

As shown in Table 12, compound 1 binds with an $IC_{50}$ value of 10.8 nM at sigma-1. Substitution on the phenyl A ring has essentially no effect on binding.

TABLE 12

| Cmp. # | X | Isomer | $IC_{50}$ (nM) |
|---|---|---|---|
| 1 | H | R (−) | 10.8 |
| 43 | H | S (+) | — |

TABLE 12-continued

[Structure: phenyl-CH2CH2-NH-CH(CH3)-CH2-phenyl-X]

| Cmp. # | X | Isomer | $IC_{50}$ (nM) |
|---|---|---|---|
| 20 | 3-Br | (±) | 9.6 |
| 21 | 4-Br | (±) | 12.0 |
| 22 | 4-I | R (−) | 17.7 |
| 23 | 3-CF$_3$ | (±) | 8.8 |
| 83 | 4-OEt | (±) | 3.4 |

Replacement of the phenyl-A with 1-naphthyl has no effect on binding. (Compare compound no. 1 to compound no. 16 (Table 13)). However, replacement of the 1-naphthyl group with a 2-naphthyl group reduces sigma-1 affinity about three fold. (Compare compound no. 16 to compound no. 17 (Table 13)). In addition, replacement of phenyl-B with 1-naphthyl or 2-naphthyl has little effect on binding. (Compare compound no. 1 to compound nos. 11 and 12 (Table 13)).

compound no. 1 to compound nos. 10 and 45 (Table 14)). Removal of the α-methyl group has little effect on sigma-1 binding. (Compare compound no. 1 to compound no. 87 (Table 14)).

TABLE 14

[Structure: phenyl-CH2-CH(R)-NH-(CH)n-phenyl]

| Cmp. # | | n | Isomer | $IC_{50}$ (nM) |
|---|---|---|---|---|
| 1 | R = CH$_3$ | 3 | R (−) | 10.8 |
| 10 | R = CH$_3$ | 4 | (±) | 4.7 |
| 44 | R = CH$_3$ | 4 | S (+) | — |
| 45 | R = CH$_3$ | 5 | S (+) | .88 |
| 87 | R = H | 3 | | 11.3 |

Holding the methylene groups linking the phenyl-B ring constant at four and removing the α-methyl group does not affect substantially the affinity to sigma-1. (Compare cmp. nos. 71 and 10 (N-phenyl-A; n=2), which have binding

TABLE 13

| Cmp. | Structure | Sigma-1 $IC_{50}$ (nM) |
|---|---|---|
| 1 | [phenyl-CH2-CH(CH3)-NH-CH2CH2-phenyl] | 10.8 |
| 16 | [1-naphthyl-CH2-CH(CH3)-NH-CH2CH2-phenyl] | 9.3 |
| 17 | [2-naphthyl-CH2-CH(CH3)-NH-CH2CH2-phenyl] | 31.0 |
| 11 | [phenyl-CH2-CH(CH3)-NH-CH2CH2-1-naphthyl] | 8.6 |
| 12 | [phenyl-CH2-CH(CH3)-NH-CH2CH2-2-naphthyl] | 5.7 |

Increasing the length of the N-phenyl-B alkyl chain of compound No. 1 from 3 to 4 methylene groups doubles affinity to the sigma-1 receptor. A further increase to 5 methylene groups substantially increases affinity. (Compare affinities of 2.6 and 4.7 nM, respectively). Shortening the number of methylene groups linking the phenyl-A substituent to one decreases affinity. (Compare cmp. nos. 71 and 75, which have binding affinities of 2.6 and 9.6, respectively.) In contrast, increasing the number of methylene groups linking the phenyl-A ring to five increases affinity. (Compare cmp. nos. 71 and 76, which have binding affinities of 2.6 and 0.48 nM, respectively.)

Since five methylenes between the phenyl-A ring and the amine is associated with high binding to sigma-1, a homologous series of related analogs were examined (Table 15).

TABLE 15

| cmp. # | n | R | IC$_{50}$ (nM) |
|---|---|---|---|
| 76 | 4 | H | 0.48 |
| 111 | 3 | H | 0.28 |
| 89 | 2 | H | 0.17 |
| 77 | 1 | H | 0.32 |
| 137 | 1 | CH$_3$ | 0.19 |

As is evident from Table 15, the length of the N-phenyl-B chain has little effect on binding to the sigma-1 site. In addition, elimination of the N-phenyl-B ring has little effect on sigma-1 receptor binding. (Cmp. #112, N-methyl-N-propyl-5-phenylpentylamine, IC$_{50}$=0.29 nM). However, an increase in the phenyl-A chain length results in a decrease in affinity to sigma-1 (compare cmp. nos. 90, N-benzyl-7-phenylheptylamine, and cmp. 91, N-phenethyl-7-phenylheptylamine which have binding affinities at sigma-1 of 2.3 and 1.5 nM, respectively).

Reduction of the phenyl-A ring of cmp. no. 77 (N-benzyl-S-phenylpentylamine, IC$_{50}$=0.32) has little effect on sigma-1 binding affinity (cmp. #94, N-benzyl-5-cyclohexylpentylamine, IC$_{50}$, 0.81).

Removal of the aromatic phenyl-B ring of the A-ring cyclohexyl compounds is also well tolerated. However, the tertiary amines appear to have enhanced affinity compared to the primary and secondary amines (Table 16).

TABLE 16

| Cmp. # | Structure | Sigma-1 IC$_{50}$ (nM) |
|---|---|---|
| 94 | 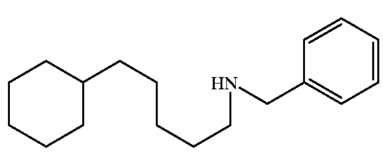 | 0.81 |
| 128 | 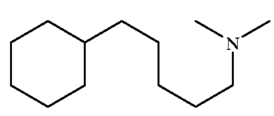 | 0.26 |
| 127 | 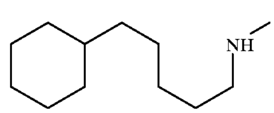 | 6.8 |

TABLE 16-continued

| Cmp. # | Structure | Sigma-1 IC$_{50}$ (nM) |
|---|---|---|
| 126 | 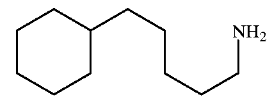 | 190 |

The most selective sigma-i binding compound is N,N-dimethyl-5-cyclohexylpentylamine (cmp. #128, sigma-2/sigma-1 selectivity of 650). Other sigma-1 selective ligands include N-methyl-5-cyclohexylpentylamine (cmp. #127, sigma-2/sigma-1 selectivity of 51), 5-cyclohexylpentylamine (cmp. #126, sigma-2/sigma-1 selectivity of 13), N-methyl-N-propyl-5-phenylpentylamine (cmp. #112, sigma-2/sigma-1 selectivity of 137), N-benzyl-7-phenylheptylamine (cmp. #90, sigma-2/sigma-1 selectivity of 126), N-(5-phenyl)pentylpiperidine (cmp. #124, sigma-2/sigma-1 selectivity of 100), and N,N-dimethyl-5-phenylpentylamine (cmp. #125, sigma-2/sigma-1 selectivity of 96).

Example 9

Structure-Activity Analysis with Regard to Sigma-2

Many alterations in structure do not improve the binding of the compounds of the present invention to the sigma-2 site. Compound #1 binds at the sigma-2 site with modest affinity (60 nM). Aromatic substitution in the phenyl-A ring has little effect on binding at sigma-2 (Table 17).

TABLE 17

| cmp. # | X | Isomer | IC$_{50}$ (nM) |
|---|---|---|---|
| 1 | H | R (−) | 60 |
| 43 | H | S (+) | — |
| 20 | 3-Br | (±) | 26 |
| 21 | 4-Br | (±) | 39 |
| 22 | 4-I | R (−) | 76 |
| 23 | 3-CF$_3$ | (±) | 21 |
| 83 | 4-OEt | (±) | 34 |

However, replacement of phenyl-A with a naphthyl ring decreases affinity to sigma-2 several fold. (Compare cmp. #1, IC$_{50}$=60 with cmp. #16, N-(3-phenylpropyl)-1-(1-naphthyl)-2-isopropylamine, and #17, N-(3-phenylpropyl)-1-(2-naphthyl)-2-isopropylamine, which have binding affinities of 150 and 220 nM, respectively.) In addition, replacement of phenyl-B with a naphthyl ring reduces affinity about 4 fold. (Compare cmp. #1, IC$_{50}$=60 with cmp. #11, N-(3-(1-naphthyl)propyl)-1-phenyl-2-isopropylamine, and #1, N-(3-(2-naphthyl)propyl)-1-phenyl-2-isopropylamine, which have binding affinities of 280 and 260 nM, respectively.) Removal of the a-methyl group of cmp. #1 has essentially no effect (IC$_{50}$ of cmp. no. 87, N-(3-phenylpropyl)-2-phenethylamine, =90 nM). Increasing the phenyl-B chain length from 3 to 4 also has little effect (IC$_{50}$ of cmp. 71, N-(4-phenylobutyl)-2-phenethyl amine =120 nM). Decreasing the phenyl-A alkyl chain length by one methylene slightly decreases affinity ($IC_{50}$ of cmp. #75, N-(4-phenylbutyl)benzylamine, =160 nM).

However, it is possible to improve binding affinity to sigma-2 by keeping the phenyl-B chain at 4 methylenes and increasing the phenyl-A chain to 5 methylenes to give a 3-fold increase in affinity (Table 18). An alkyl chain of n=3 appears to be optimal. In addition, N-methylation triples affinity.

TABLE 18

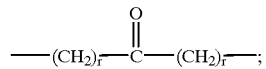

| cmp. # | n | R | $IC_{50}$ (nM) |
|---|---|---|---|
| 76 | 4 | H | 48 |
| 111 | 3 | H | 9.8 |
| 89 | 2 | H | 15 |
| 77 | 1 | H | 34 |
| 37 | 1 | $CH_3$ | 12 |

Removal of the phenyl-B ring results in a reduction in sigma-2 affinity. (Compare cmp. 111, N-(3-phenylpropyl)-5-phenylpentylamine, with N-methyl-N-propyl-5-phenylpentylamine, $IC_{50}$=40 nM).

The most selective sigma-2 ligand of the present invention is N-phenyl-N'-(3-(1-phthalimido)propyl)piperazine (cmp. #96) which has a sigma-1/sigma-2 ratio of 87. Other sigma-2 selective ligands include N-(4-phthalimido)butyl-N'-(o-methoxyphenyl)piperazine (cmp. #120; sigma-1/sigma-2 ratio of 7) and N-(4-phthalimido)butyl-N'-phenylpiperazine (cmp. #97; sigma-1/sigma-2 ratio of 10).

Having now fully described this invention, it will be understood by those of skill in the art that the same can be practiced within a wide range of equivalent conditions, formulations, structural variations and other parameters without affecting the scope of the invention or any embodiment thereof.

What is claimed is:

1. A method of treating a human being suffering from a sigma receptor associated central nervous system disorder, drug abuse, gastrointestinal disorder psychosis, angina, hypertension, migraine or depression, which comprises administering to said human a therapeutically effective amount of a compound of the formula:

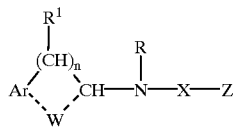

wherein:

Ar is aryl, heteroaryl, substituted aryl or substituted heteroaryl, wherein the substituent is selected from the group consisting of chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl;

R is hydrogen or $C_1$–$C_6$ alkyl;

$R^1$ is selected from the group consisting of hydrogen, $C_1$–$C_6$ alkyl, $C_1$–$C_6$ alkoxy, fluoro, chloro, bromo and =O; or R and $R^1$ together form a morpholino, piperazinyl or piperidinyl ring;

n is 0–5;

W is —$(CH_2)_p$— or —H H—, wherein p is 1–3;

X is —$(CH_2)_q$—, wherein q is 1–6;

—$(CH_2)_r$—C≡C—$(CH_2)_r$—;

—$(CH_2)_r$—CH=CH—$(CH_2)_r$—;

$$—(CH_2)_r—\overset{\overset{O}{\|}}{C}—(CH_2)_r—;$$

—$(CH_2)_r$—Y—$(CH_2)_r$—, wherein each r is independently 0–3 and wherein Y is O or S; or $C_1$–$C_6$ alkyl (wherein Z is hydrogen);

Z is hydrogen, cycloalkyl, aryl, an aryl-substituted carboxylic acid group, or heteroaryl wherein Z may be substituted by chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl or an ortho methylenedioxy group;

wherein said compound exhibits high binding activity with respect to the sigma receptor.

2. A method of treating a human being suffering from a sigma receptor associated central nervous system disorder, drug abuse, gastrointestinal disorder psychosis, angina, hypertension, migraine or depression, which comprises administering to said human a therapeutically effective amount of a compound of the formula:

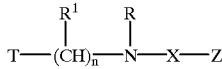

wherein:

R is hydrogen or $C_1$–$C_6$ alkyl;

T is aryl, heteroaryl, substituted aryl, substituted heteroaryl, or cycloalkyl, wherein said substituent is selected from the group consisting of chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, Cl-$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, Cl-$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl, and an ortho methylenedioxy group;

$R^1$ is selected from the group consisting of hydrogen, $C_1$–$C_6$ alkyl, $C_1$–$C_6$ alkoxy, fluoro, bromo, chloro, iodo and =0; or R and $R^1$ together form a morpholino, piperazinyl or piperidinyl ring;

n is 0–5;

X is —$(CH_2)_q$—, wherein q is 1–6;
—$(CH_2)_r$—C≡C—$(CH_2)_r$—, wherein r is 0–3;
—$(CH_2)_r$—CH═CH—$(CH_2)_r$—;

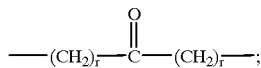

—$(CH_2)_r$—Y—$(CH_2)_r$—, wherein each r is independently 0–3 and wherein Y is O or S; or $C_1$–$C_6$ alkyl (wherein Z is hydrogen);

Z is hydrogen, cycloalkyl, aryl, an aryl-substituted carboxylic acid group, or aryl wherein Z may be substituted by chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl, or an ortho methylenedioxy group;

wherein said compound exhibits high binding activity with respect to the sigma receptor.

3. The method of claim 2, wherein said compound is selected from the group consisting of N-phenethyl-1-phenylisopropylamine, N-(3-phenylpropyl)-1-phenyl-isopropylamine, N-(2-phenoxy)ethyl)-1-phenylisopropylamine, N-(3-phenyl-3-propanon-1-yl)-1-phenylisopropylamine, N-(4-phenylbutyl)-1-phenylisopropylamine, N-(3-(1-naphthyl)propyl)-1-phenylisopropylamine,N-(3-(2-naphthyl)propyl)-1-phenylisopropylamine, N-methyl-N-(3-(2-naphthyl)propyl)-1-phenylisopropylamine, N-(3-phenyl-2-propyn-1-yl)-1-phenyl-isopropylamine, N-(3-phenylpropyl)-1-(4-hydroxyphenyl)isopropylamine,N-(3-phenylpropyl)-1-(4-methoxyphenyl)isopropylamine, N-(3-phenylpropyl)-1-(3-bromophenyl)isopropylamine, N-(3-phenylpropyl)-1-(4-bromophenyl)isopropylamine, N-(3-phenylpropyl)-1-(3,4-dichlorophenyl)isopropylamine, N-(3-phenylpropyl)-1-(4-iodophenylisopropyl)-amine, N-(3-phenylpropyl)-1-(3-trifluoromethylphenyl)isopropylamine, N-(2-phenethyl)-N-methyl-1-phenylisopropylamine, N-(3-phenylpropyl)-1-phenylpropan-1-one-2-amine, N-(2-indanyl)-3-phenylpropylamine,N,N-di-(3-phenylpropyl)amine, N-(2-(1-naphthyl)ethyl)-1-phenylisopropylamine, N-(2-(2-naphthyl)ethyl)-1-phenylisopropylamine, N-(2-(1-naphthyl)propyl)-1-phenylisopropylamine, N-(2-(2-naphthyl)propyl)-1-phenylisopropylamine, N-(4-phenylbutyl)-1-(2,5-dimethoxyphenyl)isopropylamine, N-(4-phenylbutyl)-1-(4-bromo-2,5-dimethoxyphenyl)isopropylamine, N-methyl-N-(4-phenylbutyl)-1-phenylisopropylamine, N-methyl-N-(5-phenylpentyl)-1-phenylisopropylamine, N-(3-phenylpropyl)-1-(4-ethoxyphenyl)isopropyl-amine, N-(3-phenylpropyl)-1-(4-propylphenyl)isopropylamine, N-(3-phenylpropyl)-1-(4-benzoxyphenyl)isopropylamine, N-methyl-N-(3-phenylpropyl)-1-(4-propylphenyl)isopropylamine, N-(3-phenylpropyl)-1-phenyl-2-pentylamine,N-(4-phenylbutyl)-1-phenyl-2-pentylamine,N,N-di-(2-ethylphenyl)methylamine,N,N-dibenzylamine,N-(3-phenylpropyl)-N-(6-phenylhexyl)amine, N-(3-phenylpropyl)-N-(5-phenylpentyl)amine, N-propyl-N-methyl-5-phenylpentylamine, N-methyl-N-(3-phenylpropyl)- 1-phenyl isopropylamine, N-methyl -N-(3-methyl-2-butenyl)-1-phenyliso-propylamine, N-methyl-N-(3-methylbutyl)-1-phenylisopropylamine, N-methyl-N-(3-phenylpropyl)-1-phenyl-2-pentylamine, N-methyl-N-(3-methylbutyl)-1-isopropylamine, N-methyl-N-(3-phenylbutyl)-1-phenyl-2-pentylamine, N-propyl-N-(3-phenyl)propyl)-1-phenyl-2-propylamine, N-benzyl-N-(3-phenyl)-propyl)-1-phenyl-2-propylamine, N-phenyl-(5-phenyl)pentylamine, N-methyl-N-(3-phenyl)propyl-5-phenylpentylamine,N-(2-(o-methylphenyl)ethyl)-5-phenylpentylamine, N-(2-(m-methylphenyl)ethyl)-5-phenylpentylamine, N-(2-(p-methylphenyl)ethyl)-5-phenylpentylamine, N-benzyl-5-phenylpentylamine, N-benzyl-N-methyl-5-phenyl-pentylamine,N-(2-(3-hydroxyphenyl)ethyl)-5-phenylpentylamine,N-(2-(2-hydroxyphenyl)ethyl)-5-phenylpentylamine, N,N'-diethyl-2-(diphenylacetoxy)ethylamine,N,N'-diethyl-2-(9-fluorenecarboxy)-ethylamine, N,N-Dimethyl-5-phenylpentylamine, N-Benzyl-N-(3-phenylpropyl)-1-phenyl-2-propylamine, N-Benzyl-N-methyl-5-phenylpentylamine, N-Benzyl-5-phenylpentylamine, and N-(2-phenethyl)-N-methylpentylamine.

4. A method of treating a human being suffering from a sigma receptor associated central nervous system disorder, drug abuse, gastrointestinal disorder psychosis, angina, hypertension, migraine or depression, which comprises administering to said, human a therapeutically effective amount of a compound of the formula:

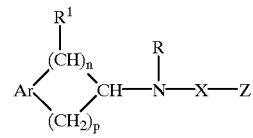

wherein:

R is hydrogen or $C_1$–$C_6$ alkyl;

Ar is aryl, heteroaryl, substituted aryl or substituted heteroaryl, wherein the substituent is selected from the group consisting of chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl; $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$-$C_6$ alkylamino, $C_2$-$C_{15}$ dialkylamino, hydroxy, carbamoyl, $C_1$-$C_6$ N-alkylcarbamoyl, $C_2$-$C_{15}$ N,N-dialkylcarbamoyl, nitro and $C_2$-$C_{15}$ dialkylsulfamoyl;

$R^1$ is selected from the group consisting of hydrogen, $C_1$-$C_6$ alkyl, $C_1$-$C_6$ alkoxy, fluoro, chloro, bromo, iodo and =0; or R and $R^1$ together form a morpholino, piperazinyl or piperidinyl ring;

n is 1–3;

p is 1–3;

X is —$(CH_2)_q$—, wherein q is 1–6; —$(CH_2)_r$—C≡C—$(CH_2)_r$—; —$(CH_2)_r$—CH=CH—$(CH_2)_r$—, —$(CH_2)_r$—C(=O)—$(CH_2)_r$—, —$(CH_2)_r$—Y—$(CH_2)_r$—, wherein each r is independently 0–3 and wherein Y is O or S; or $C_1$-$C_6$ alkyl;

Z is hydrogen, cycloalkyl, aryl or heteroaryl wherein Z may be substituted by chloro, fluoro, bromo, iodo, $CF_3$, $C_1$-$C_6$ alkoxy, $C_2$-$C_6$ dialkoxymethyl, $C_1$-$C_6$ alkyl, cyano, $C_3$-$C_{15}$ dialkylaminoalkyl, carboxy, carboxamido, $C_1$-$C_6$ haloalkyl, $C_1$-$C_6$ haloalkylthio, allyl, aralkyl, $C_3$-$C_6$ cycloalkyl, aroyl, aralkoxy, $C_2$-$C_6$ carboxylic acyl, aryl, substituted aryl, heteroaryl, substituted heteroaryl, $C_3$-$C_6$ heterocycloalkyl, $C_1$-$C_6$ alkylthio, $C_{1-6}$ alkylsulfonyl, $C_1$-$C_6$ haloalkylsulfonyl, $C_1$-$C_6$ alkyl-sulfinyl, $C_1$-$C_6$ haloalkylsulfinyl, arylthio, $C_1$-$C_6$ haloalkoxy, amino, $C_1$-$C_6$ alkylamino, $C_2$-$C_{15}$ dialkylamino, hydroxy, carbamoyl, $C_1$-$C_6$ N-alkylcarbamoyl, $C_2$-$C_{15}$ N,N-dialkylcarbamoyl, nitro, $C_2$-$C_{15}$ dialkylsulfamoyl or methylenedioxy;

wherein said compound exhibits a high binding activity with respect to the sigma receptor.

5. The method of claim 4, wherein said compound is selected from the group consisting of N-(2-indanyl)-1-phenylisopropylamine, N-(2-indanyl)-3-phenylpropylamine, N-(4,5-benzocycloheptyl)-1-phenylisopropylamine, N-(3,4-benzocycloheptyl)-3-(phenyl)propylamine, N-(4,5-benzocycloheptyl)-3-phenylpropylamine, N-(3,4-benzocyclohexyl)-1-phenylisopropylamine and N-3,4-benzocyclohexyl-3-phenylpropylamine.

6. A method of treating a human being suffering from a sigma receptor associated central nervous system disorder, drug abuse, gastrointestinal disorder, psychosis, angina, hypertension, migraine or depression, which comprises administering to said human a therapeutically effective amount of a compound of the formula:

wherein:

$R^4$ is hydrogen or an aryl group substituted with a group selected from the group consisting of $C_1$-$C_6$ alkyl, $C_1$-$C_6$ alkenyl, $C_2$-$C_6$ dialkoxymethyl, $C_3$-$C_{15}$ dialkylaminoalkyl, aralkyl, $C_3$-$C_6$ cycloalkyl, aroyl, $C_2$-$C_6$ acyl, aryl, substituted aryl, heteroaryl, substituted heteroaryl, $C_3$-$C_6$ heterocycloalkyl;

$R^5$ is hydrogen or hydroxy;

X is —$(CH_2)_q$—, wherein q is 1–6; —$(CH_2)_r$—C≡C—$(CH_2)_r$—, —$(CH_2)_r$—CH=CH—$(CH_2)_r$—;

—$(CH_2)_r$—C(=O)—$(CH_2)_r$—,

—$(CH_2)_r$—Y—$(CH_2)_r$—, wherein each r is independently 0–3 and wherein Y is O or S; or $C_1$-$C_6$ alkyl (wherein Z is hydrogen);

Z is cycloalkyl, aryl or heteroaryl wherein Z may be substituted by chloro, fluoro, bromo, iodo, $CF_3$, $C_1$-$C_6$ alkoxy, $C_2$-$C_6$ dialkoxymethyl, $C_1$-$C_6$ alkyl, cyano, $C_3$-$C_{15}$ dialkylaminoalkyl, carboxy, carboxamido, $C_1$-$C_6$ haloalkyl, $C_1$-$C_6$ haloalkylthio, allyl, aralkyl, $C_3$-$C_6$ cycloalkyl, aroyl, aralkoxy, $C_2$-$C_6$ carboxylic acyl, aryl, substituted aryl, heteroaryl, substituted heteroaryl, $C_3$-$C_6$ heterocycloalkyl, $C_1$-$C_6$ alkylthio, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, arylthio, $C_1$-$C_6$ haloalkoxy, amino, $C_1$-$C_6$ alkyl-amino, dialkylamino, hydroxy, carbamoyl, $C_1$-$C_6$ N-alkylcarbamoyl, $C_2$-$C_{15}$ N,N-dialklcarbamoyl, nitro, $C_2$-$C_{15}$ dialkylsulfamoyl or methylenedioxy;

wherein said compound exhibits a high binding activity with respect to the sigma receptors.

7. The method of claim 6, wherein said compound is selected from the group consisting of N-(5-phenylpentyl)-piperidine, N-(8-phenylheptyl)piperidine, N-(5-(4-methoxyphenyl)pentyl)piperidine, N-(3-phenylpropyl)piperidine, N-(5-cyclohexyl)pentylpiperidine, N-benzylpiperidine, N-(2-phenethyl)-4-hydroxy-4-phenylpiperidine, N-(2-phenethyl)-4-hydroxy-4-t-butylpiperidine, N-(5-(4-chlorophenyl)-5-pentanon-1-yl)piperidine, N-(5-(4-chlorophenyl)-5-pentanon-1-yl)-4-phenylpiperidine, N-(5-(4-methoxyphenyl)-5-pentanon-1-yl)piperidine, N-(5-(4-methoxyphenyl)-5-pentanon-1-yl)-4-phenylpiperidine, N-(5-(4-methoxyphenyl)pentyl)-4-phenylpiperidine, N-(5-phenyl-5-pentanon-1-yl)-4-phenylpiperidine, N-(5-(4-chlorophenyl)-pentyl)-4-phenylpiperidine, N-(5-(3-methoxyphenyl)-5-pentanon-1-yl)piperidine, N-(5-(3-chlorophenyl)-5-pentanon-1-yl)piperidine, N-(5-(3-chlorophenyl)-5-pentanon-1-yl)-4-phenylpiperidine, N-(5-(3-methoxyphenyl)-5-pentanon-1-yl)-4-phenylpiperidine, N-(4-(4-fluorophenyl)-4-butanon-1-yl)piperidine, N-(5-(4-fluorophenyl)-5-pentanon-1-yl) piperidine, N-(5-(4-fluorophenyl)-5-pentanon-1-yl)-4-phenylpiperidine, N-(5-(4-fluorophenyl)-5-pentanon-1-yl)-4-(3-chlorophenyl)-4-hydroxypiperidine, N-(5-(4-chlorophenyl)-5-pentanon-1-yl)-4-(4-fluorophenyl)-1,2,3,6-terahydropyridine, N-(5-(4-chlorophenyl)-5-pentanon-1-yl)-4-(4-fluorophenyl)-piperidine, N-(5-(4-chlorophenyl)-5-pentanon-1-yl)-4-(4-fluorophenyl)- 1,2,3,6-terahydropyridine, N-(5-(4-chlorophenyl)-5-pentanon-1-yl)-4-(4-fluorophenyl)-piperidine, N-(S-(4-chlorophenyl)-5-pentanon-1-yl)-4-(chlorophenyl)-1,2,3,6-terahydropyridine, N-(5-(4-chlorophenyl)-5-pentanon-1-yl)-4-(chlorophenyl) piperidine, N-(5-(3,4-dichlorophenyl)-5-pentanon-1-yl)-4-(chlorophenyl)-piperidine, N-(5-cyclopentylpentan-5-on-1-yl)piperidine and N-(5-(3,4-methylenedioxyphenyl)penta-2,4-dienyl)piperidine.

8. A method of treating a human being suffering from a sigma reception associated central nervous system disorder, drug abuse, gastrointestinal disorder, psychosis, angina, hypertension, migraine or depression, which comprises administering to said human a therapeutically effective amount of a compound having the formula:

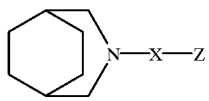

wherein,

X is —(CH$_2$)$_q$—, wherein q is 1–6,

—(CH$_2$)$_r$—C≡C—(CH$_2$)$_r$—;

—(CH$_2$)$_r$—CH═CH—(CH$_2$)$_r$—;

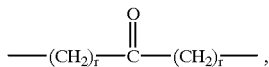

—(CH$_2$)$_r$—Y—(CH$_2$)$_r$—, wherein each r is independently 0–3 and wherein Y is O or S; or C$_1$–C$_6$ alkyl (wherein Z is hydrogen);

Z is cycloalkyl, aryl or heteroaryl wherein Z may be substituted by chloro, fluoro, bromo, iodo, CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, aryl, substituted aryl, heteroaryl, substituted heteroaryl, C$_3$–C$_6$ heterocycloalkyl, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkyl-amino, dialkylamino, hydroxy, carbamoyl, C$_1$–C$_6$ N-alkylcarbamoyl, C$_2$–C$_{15}$ N,N-dialklcarbamoyl, nitro, C$_2$–C$_{15}$ dialkylsulfamoyl or methylenedioxy;

wherein said compound exhibits a high binding activity with respect to the sigma receptors.

9. The method of claim 8, wherein said compound is N-(5-phenyl)pentyl-3-azabicyclo[3.2.2]nonane.

10. A method of treating a human being suffering from a sigma receptor associated central nervous system disorder, drug abuse, gastrointestinal disorder, psychosis, angina, hypertension, migraine or depression, which comprises administering to said human a therapeutically effective amount of a compound of the formula:

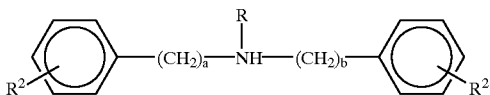

wherein a is 1–8;

b is 1–8;

R is hydrogen or C$_1$–C$_6$ alkyl;

R$^2$ is independently selected from the group consisting of hydrogen, chloro, fluoro, bromo, iodo, CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, aryl, substituted aryl, heteroaryl, substituted heteroaryl, C$_3$–C$_6$ heterocycloalkyl, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, dialkylamino, hydroxy, carbamoyl, C$_1$–C$_6$ N-alkylcarbamoyl, C$_2$–C$_{15}$ N,N-dialklcarbamoyl, nitro and C$_2$–C$_{15}$ dialkylsulfamoyl;

wherein said compound exhibits high binding activity with respect to the sigma receptor.

11. The method of claim 10 wherein said compound is selected from the group consisting of N-(4-phenylbutyl) phenethyl-amine, N-(4-phenylbutyl)-3-phenylpropylamine, N-(4-phenylbutyl)-4-phenylbutylamine, N-(4-phenylbutyl) benzylamine, N-(4-phenylbutyl)-5-phenylpentylamine, N-(5-phenylpentyl)benzylamine, N-(3-phenylpropyl) phenethylamine, N-(5-phenylpentyl)phenethylamine, N-(7-phenylheptyl)benzylamine, N-(7-phenylheptyl)phenethylamine, N-methyl-N-(2-phenethyl)-1-phenylisopropylamine, N-methyl-N-(5-phenylpentyl)-1-phenylisopropylamine, N-methyl-N-(3-phenylpropyl)-1-(4-propylphenyl)isopropylamine, N-phenyl-(5-phenyl) pentylamine, N-methyl-N-(3-phenylpropyl)-5-phenylpentylamine, N-benzyl-N-methyl-5-phenylpentylamine, N-(2-(o-methoxyphenyl)ethyl)-5-phenylpentylamine, N-(2-(m-methoxyphenyl)ethyl)-5-phenylpentylamine, N-(2-(p-methoxyphenyl)ethyl)-5-phenylpentylamine, N-benzyl-5-phenylpentylamine, N-(2-(m-hydroxyphenyl)ethyl)-5-phenylpentylamine, and N-(2-(o-hydroxyphenyl)ethyl)-5-phenylpentylamine.

12. A method of treating a human being suffering from a sigma receptor associated central nervous system disorder, drug abuse, gastrointestinal disorder, psychosis, angina, hypertension, migraine or depression, which comprises administering to said human a therapeutically effective amount of a compound having the Formula:

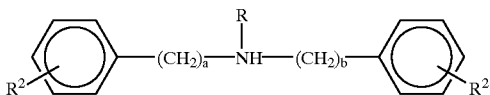

wherein a is 1–8;

b is 1–8;

R is hydrogen or C$_1$–C$_6$ alkyl;

R$^2$ is independently selected from the group consisting of hydrogen, chloro, fluoro, bromo, iodo, CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, aryl, substituted aryl, heteroaryl, substituted heteroaryl, C$_3$–C$_6$ heterocycloalkyl, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkyl-amino, dialkylamino, hydroxy, carbamoyl, C$_1$–C$_6$ N-alkylcarbamoyl, C$_2$–C$_{15}$ N,N-dialklcarbamoyl, nitro and C$_2$–C$_{15}$ dialkylsulfamoyl; and wherein said compound exhibits high binding activity with respect to the sigma receptor.

13. The method of claim 12, wherein said compound is N-(3-phenylpropyl)-2-(2-naphthyl)ethylamine.

14. A method of treating a human being suffering from a sigma receptor associated central nervous system disorder, drug abuse, gastrointestinal disorder psychosis, angina, hypertension, migraine or depression, which comprises administering to said human a therapeutically effective amount of a compound having the formula:

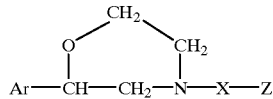

wherein;

Ar is aryl, heteroaryl, substituted aryl or substituted heteroaryl, wherein the substituent is selected from the group consisting of chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

X is —$(CH_2)_q$—, wherein q is 1–6;
—$(CH_2)_r$—CH=C—$(CH_2)_r$—;
—$(CH_2)_r$—CH=CH—$(CH_2)_r$—;

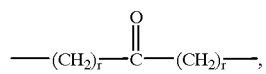

—$(CH_2)_r$—Y—$(CH_2)_r$—, wherein each r is independently 0–3 and wherein Y is O or S; or $C_1$–$C_6$ alkyl;

Z is hydrogen, cycloalkyl, aryl or heteroaryl wherein Z may be substituted by chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl or methylenedioxy;

wherein said compound exhibits high binding activity with respect to the sigma receptor.

15. A method of treating a human being suffering from a sigma receptor associated central nervous system disorder, drug abuse, gastrointestinal disorder, psychosis, angina, hypertension, migraine or depression, which comprises administering to said human a therapeutically effective amount of a compound having the formula:

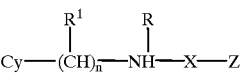

wherein n is 0–5;

Cy is $C_3$–$C_8$ cycloalkyl;

R is hydrogen or $C_1$–$C_6$ alkyl;

$R^1$ is independently selected from the group consisting of hydrogen, $C_1$–$C_6$ alkyl, $C_1$–$C_6$ alkoxy, fluoro, chloro, bromo, iodo and =O;

X is —$(CH_2)_q$—, wherein q is 1–6;
—$(CH_2)_r$—C=C—$(CH_2)_r$—, wherein r is 0–3;
—$(CH_2)_r$—CH=CH—$(CH_2)_r$—;

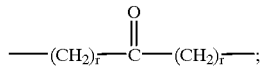

—$(CH_2)_r$—Y—$(CH_2)_r$—, wherein each r is independently 0–3 and wherein Y is O or S; or $C_1$–$C_6$ alkyl (wherein Z is hydrogen); and Z is hydrogen, cycloalkyl, aryl or heteroaryl wherein Z may be substituted by chloro, fluoro, bromo, iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–C6 haloalkyl, $C_1$–$C_6$ haloalkylthio, allyl, aralkyl, $C_3$–$C_6$ cycloalkyl, aroyl, aralkoxy, $C_2$–$C_6$ carboxylic acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl or methylenedioxy;

wherein said compound exhibits high binding activity with respect to the sigma receptor.

16. The method of claim 15, wherein said compound is selected from the group consisting of N-(3-cyclohexylpropyl)-3-phenylpropylamine, N-cyclohexylmethyl-3-phenylpropylamine, N-(5-cyclohexylpentyl)benzylamine, 5-cyclohexylpentylamine, N-methyl-5-cyclohexylpentylamine, N,N-Dimethyl-5-cyclohexylpentylamine, N-cyclohexylmethyl-5-cyclohexyl-n-pentylamine, and N-cyclohexylmethyl-N-methyl-5-cyclohexyl-n-pentylamine.

17. A method of treating a human being suffering from a sigma receptor associated central nervous system disorder, psychosis, angina, hypertension, migraine drug abuse, gastrointestinal disorder or depression, which comprises administering to said human a therapeutically effective amount of a compound having the formula:

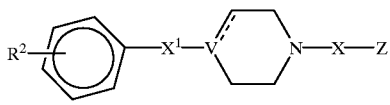

wherein $X^1$ is —$(CH_2)_r$—C=C—$(CH_2)_r$—, wherein each r is 0–3 independently;

$-(CH_2)_r-CH=CH-(CH_2)_r-$;

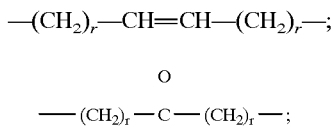

$-(CH_2)_r-Y-(CH_2)_r-$, wherein Y is O or S; or $C_1-C_6$ alkyl (wherein Z is hydrogen);

$R^2$ is independently selected from the group consisting of hydrogen, chloro, fluoro, bromo, iodo, $CF_3$, $C_1-C_6$ alkoxy, $C_2-C_6$ dialkoxymethyl, $C_1-C_6$ alkyl, cyano, $C_3-C_{15}$ dialkylaminoalkyl, carboxy, carboxamido, $C_1-C_6$ haloalkyl, $C_1-C_6$ haloalkylthio, allyl, aralkyl, $C_3-C_6$ cycloalkyl, aroyl, aralkoxy, $C_2-C_6$ carboxylic acyl, aryl, substituted aryl, heteroaryl, substituted heteroaryl, $C_3-C_6$ heterocycloalkyl, $C_1-C_6$ alkylthio, $C_1-C_6$ alkylsulfonyl, $C_1-C_6$ haloalkylsulfonyl, $C_1-C_6$ alkylsulfinyl, $C_1-C_6$ haloalkylsulfinyl, arylthio, $C_1-C_6$ haloalkoxy, amino, $C_1-C_6$ alkyl-amino, dialkylamino, hydroxy, carbamoyl, $C_1-C_6$ N-alkylcarbamoyl, $C_2-C_{15}$ N,N-dialkicarbamoyl, nitro and $C_2-C_{15}$ dialkylsulfamoyl;

V is N or CM, wherein M is hydrogen, $C_1-C_6$ alkyl, $C_1-C_6$ alkoxy, fluoro, chloro, bromo, trifluoromethyl, hydroxy or one half of a double bond with the neighboring endocyclic carbon;

X is $-(CH_2)q$-1 wherein q is 1–6;

$-(CH_2)_r-C\equiv C-(CH_2)_r-$, wherein r is 0–3;

$-(CH_2)_r-CH=CH-(CH_2)_r-$;

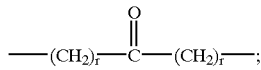

$-(CH_2)_r-Y-(CH_2)_r-$, wherein each r is independently 0–3 and wherein Y is O or S; or $C_1-C_6$ alkyl (wherein Z is hydrogen); and Z is hydrogen, cycloalkyl, aryl or heteroaryl wherein Z may be substituted by chloro, fluoro, bromo, iodo, $CF_3$, $C_1-C_6$ alkoxy, $C_2-C_6$ dialkoxymethyl, $C_1-C_6$ alkyl, cyano, $C_3-C_{15}$ dialkylaminoalkyl, carboxy, carboxamido, $C_1-C_6$ haloalkyl, $C_1-C_6$ haloalkylthio, allyl, aralkyl, $C_3-C_6$ cycloalkyl, aroyl, aralkoxy, $C_2-C_6$ carboxylic acyl, aryl, substituted aryl, heteroaryl, substituted heteroaryl, $C_3-C_6$ heterocycloalkyl, $C_1-C_6$ alkylthio, $C_1-C_6$ alkylsulfonyl, $C_1-C_6$ haloalkylsulfonyl, $C_1-C_6$ alkylsulfinyl, $C_1-C_6$ haloalkylsulfinyl, arylthio, $C_1-C_6$ haloalkoxy, amino, $C_1-C_6$ alkylamino, $C_2-C_{15}$ dialkylamino, hydroxy, carbamoyl, $C_1-C_6$ N-alkylcarbamoyl, $C_2-C_{15}$ N,N-dialkylcarbamoyl, nitro and $C_2-C_{15}$ dialkylsulfamoyl;

wherein said compound exhibits high binding activity with respect to the sigma receptor.

18. A method of treating a human being suffering from a sigma receptor associated central nervous system disorder, drug abuse, gastrointestinal disorder psychosis, angina, hypertension, migraines or depression, which comprises administering to said human a therapeutically effective amount of a compound having the formula:

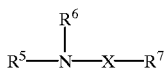

wherein $R^5$ and $R^6$ are independently a $C_{1-8}$ alkyl group;

$R^7$ is hydrogen or a $C_{1-8}$ alkyl group substituted by an arylacetoxy or arylcarboxy group; and X is $-(CH_2)_q-$, wherein q is 1–6;

$-(CH_2)_r-C\equiv C-(CH_2)_r-$, wherein r is 0–3;

$-(CH_2)_r-CH=CH-(CH_2)_r-$;

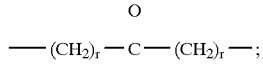

$-(CH_2)_r-Y-(CH_2)_r-$, wherein each r is independently 0–3 and wherein Y is O or S; or $C_1-C_6$ alkyl (wherein $R^7$ is hydrogen);

wherein said compound exhibits a high binding activity with respect to the sigma receptors.

19. The method of claim 18, wherein said compound is selected from the group consisting of N,N-dimethyl-n-hexylamine, N-methyl-N-propylhexylamine, N,N'-diethyl-2-(diphenylacetoxy)ethylamine, and N,N'-diethyl-2-(9-fluorenecarboxy)ethylamine.

20. The method of any one of claims 1, 2, 4, 8, 10, 12, 14, 15, 17 or 18 wherein said compound is administered as part of a pharmaceutical composition comprising a pharmaceutically acceptable carrier.

21. The method of claim 2 where T is phenyl or substituted phenyl, $R^1$ is independently hydrogen or $C_1-C_6$ alkyl, X is $-(CH_2)_q-$ and Z is hydrogen, cycloalkyl or aryl.

22. The method of claim 21 where Z is hydrogen, cycloalkyl or phenyl.

23. The method of claim 21 where T is phenyl, n and q are each 2, R is $C_{1-6}$ alkyl, and Z is phenyl.

24. The method of claim 2, where T is phenyl or substituted phenyl, $R^1$ is independently hydrogen or $C_1-C_6$ alkyl, X is $-(CH_2)_r-CH=CH-(CH_2)_r-$, and Z is hydrogen, cycloalkyl or aryl.

25. The method of claim 24 where Z is hydrogen, cycloalkyl or phenyl.

26. The method of claim 25 where R is $C_1-C_6$ alkyl.

27. The method of claim 2 where T is phenyl, R and $R^1$ are each hydrogen, X is $-(CH_2)_q-$ and cycloalkyl.

28. The method of claim 27 where n is 1 and q is 4.

29. The method of claim 2 where T is phenyl, $R^1$ is hydrogen, R is $C_1-C_6$ alkyl, X is $-(CH_2)_q-$ and Z is hydrogen.

30. The method of claim 29 where n is 5, and q is 3.

31. The method of claim 30 where R is methyl.

32. The method of claim 1 wherein the human being is suffering from a central nervous system disorder.

33. The method of claim 1 wherein the human being is suffering from psychiatric disorders.

34. The method of claim 1 wherein the human being is suffering from Parkinson's disease, tardive dyskinesia or dystonias.

35. The method of claim 1 wherein the human being is suffering from drug abuse.

36. The method of claim 1 wherein the human is suffering from a gastrointestinal disorder.

37. The method of claim 1 wherein the human is suffering from depression.

38. The method of claim 2 wherein the human being is suffering from a central nervous system disorder.

39. The method of claim 2 wherein the human being is suffering from psychiatric disorders.

40. The method of claim 2 wherein the human being is suffering from Parkinson's disease, tardive dyskinesia or dystonias.

41. The method of claim 2 wherein the human being is suffering from drug abuse.

42. The method of claim 2 wherein the human is suffering from a gastrointestinal disorder.

43. The method of claim 2 wherein the human is suffering from depression.

44. The method of claim 21 wherein the human being is suffering from a central nervous system disorder.

45. The method of claim 21 wherein the human being is suffering from psychiatric disorders.

46. The method of claim 21 wherein the human being is suffering from Parkinson's disease, tardive dyskinesia or dystonias.

47. The method of claim 21 wherein the human being is suffering from drug abuse.

48. The method of claim 21 wherein the human is suffering from a gastrointestinal disorder.

49. The method of claim 21 wherein the human is suffering from depression.

50. The method of claim 24 wherein the human being is suffering from a central nervous system disorder.

51. The method of claim 24 wherein the human being is suffering from psychiatric disorders.

52. The method of claim 24 wherein the human being is suffering from Parkinson's disease, tardive dyskinesia or dystonias.

53. The method of claim 24 wherein the human being is suffering from drug abuse.

54. The method of claim 24 wherein the human is suffering from a gastrointestinal disorder.

55. The method of claim 24 wherein the human is suffering from depression.

56. The method of claim 29 wherein the human being is suffering from a central nervous system disorder.

57. The method of claim 29 wherein the human being is suffering from psychiatric disorders.

58. The method of claim 29 wherein the human being is suffering from Parkinson's disease, tardive dyskinesia or dystonias.

59. The method of claim 29 wherein the human being is suffering from drug abuse.

60. The method of claim 29 wherein the human is suffering from a gastrointestinal disorder.

61. The method of claim 29 wherein the human is suffering from depression.

62. The method of claim 1 wherein the compound exhibits low binding affinity to the dopamine receptor.

63. The method of claim 2 wherein the compound exhibits low binding affinity to the dopamine receptor.

64. The method of claim 4 wherein the compound exhibits low binding affinity to the dopamine receptor.

65. The method of claim 6 wherein the compound exhibits low binding affinity to the dopamine receptor.

66. The method of claim 8 wherein the compound exhibits low binding affinity to the dopamine receptor.

67. The method of claim 10 wherein the compound exhibits low binding affinity to the dopamine receptor.

68. The method of claim 12 wherein the compound exhibits low binding affinity to the dopamine receptor.

69. The method of claim 14 wherein the compound exhibits low binding affinity to the dopamine receptor.

70. The method of claim 15 wherein the compound exhibits low binding affinity to the dopamine receptor.

71. The method of claim 17 wherein the compound exhibits low binding affinity to the dopamine receptor.

72. The method of claim 18 wherein the compound exhibits low binding affinity to the dopamine receptor.

* * * * *